(12) United States Patent
Choi et al.

(10) Patent No.: US 10,141,519 B2
(45) Date of Patent: Nov. 27, 2018

(54) COMPOUND, LIGHT EMITTING DEVICE COMPRISING SAME, AND ELECTRONIC DEVICE

(71) Applicant: LMS Co., Ltd., Gyeonggi-do (KR)

(72) Inventors: Jeong Og Choi, Seoul (KR); Joon Ho Jung, Gyeonggi-do (KR); Oh Kwan Kwon, Gyeonggi-do (KR)

(73) Assignee: LMS CO., LTD., Gyeonggi-do (KR)

( * ) Notice: Subject to any disclaimer, the term of this patent is extended or adjusted under 35 U.S.C. 154(b) by 380 days.

(21) Appl. No.: 14/763,836

(22) PCT Filed: Jan. 28, 2014

(86) PCT No.: PCT/KR2014/000775
§ 371 (c)(1),
(2) Date: Oct. 20, 2015

(87) PCT Pub. No.: WO2014/119895
PCT Pub. Date: Aug. 7, 2014

(65) Prior Publication Data
US 2016/0126476 A1    May 5, 2016

(30) Foreign Application Priority Data
Jan. 30, 2013    (KR) .................. 10-2013-0010592

(51) Int. Cl.
*C09K 11/06* (2006.01)
*H01L 51/00* (2006.01)
(Continued)

(52) U.S. Cl.
CPC ........ *H01L 51/0072* (2013.01); *C07D 455/03* (2013.01); *C07D 455/04* (2013.01);
(Continued)

(58) Field of Classification Search
CPC .. C07D 455/03; C07D 455/04; C07D 471/04; H01L 51/0052; H01L 51/0059;
(Continued)

(56) References Cited

U.S. PATENT DOCUMENTS

2008/0220286 A1* 9/2008 Qiu .................. C07C 13/15
428/690
2009/0295275 A1  12/2009 Parham et al.
(Continued)

FOREIGN PATENT DOCUMENTS

EP        2182040        5/2010
WO    WO 2014/119895    8/2014

OTHER PUBLICATIONS

International Search Report dated Jun. 27, 2014 From the Korean Intellectual Property Office Re. Application No. PCT/KR2014/000775 and Its Translation Into English.
(Continued)

*Primary Examiner* — Dawn L Garrett
(74) *Attorney, Agent, or Firm* — Polsinelli PC

(57) ABSTRACT

A novel compound for improving the hole injection and transport properties in a light emitting device, a light emitting device including the compound, and an electronic device including a light emitting device are provided.

9 Claims, 1 Drawing Sheet

(51) Int. Cl.
*H01L 51/50* (2006.01)
*C07D 455/04* (2006.01)
*C07D 471/04* (2006.01)
*C07D 455/03* (2006.01)

(52) U.S. Cl.
CPC ............ *C07D 471/04* (2013.01); *C09K 11/06* (2013.01); *H01L 51/0052* (2013.01); *H01L 51/0059* (2013.01); *H01L 51/0074* (2013.01); H01L 51/506 (2013.01); H01L 51/5056 (2013.01); H01L 51/5064 (2013.01); H01L 51/5088 (2013.01); H01L 51/5096 (2013.01)

(58) Field of Classification Search
CPC ............ H01L 51/0072; H01L 51/0074; H01L 51/5056; H01L 51/506; H01L 51/5064; H01L 51/5088; H01L 51/5096; C09K 11/06
See application file for complete search history.

(56) References Cited

U.S. PATENT DOCUMENTS

| 2012/0292576 | A1 | 11/2012 | Parham et al. | |
|---|---|---|---|---|
| 2015/0349271 | A1* | 12/2015 | Choi | H01L 51/0052 257/40 |
| 2016/0248019 | A1* | 8/2016 | Choi | H01L 51/0059 |

OTHER PUBLICATIONS

Fang et al. "Bridged-Triarylamine Starburst Oligomers as Hole Transporting Materials for Electroluminescent Devices", Journal of Materials Chemistry 22 (2012): 15397-15404.

Field et al. "Bridged Triarylamines: A New Class of Heterohelicenes", Journal of Organic Chemistry, 68.16 (2003): 6071-6078.

* cited by examiner

[Fig. 1]
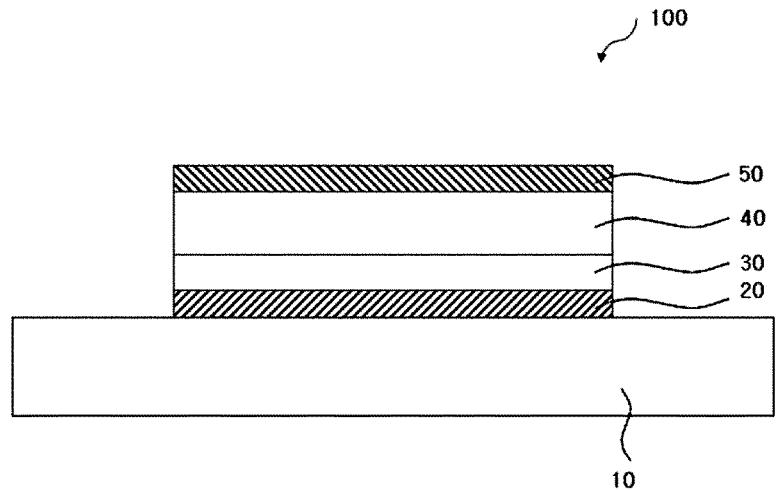
[Fig. 2]
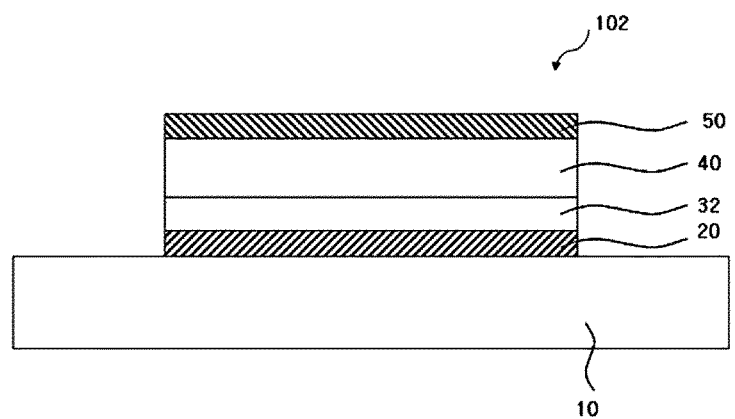
[Fig. 3]
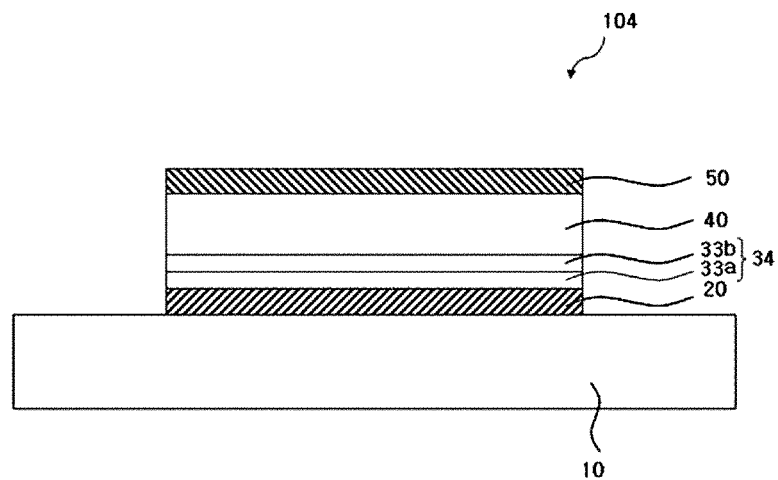

COMPOUND, LIGHT EMITTING DEVICE COMPRISING SAME, AND ELECTRONIC DEVICE

RELATED APPLICATIONS

This application is a National Phase of PCT Patent Application No. PCT/KR2014/000775 having International filing date of Jan. 28, 2014, which claims the benefit of priority of Korean Patent Application No. 10-2013-0010592 filed on Jan. 30, 2013. The contents of the above applications are all incorporated by reference as if fully set forth herein in their entirety.

BACKGROUND

Field of the Invention

The present invention relates to a novel compound, a light emitting device including the same, and an electronic device, and more particularly, to a compound for an organic light emitting device, a light emitting device including the same, and an electronic device.

Background Art

In general, a light emitting device includes two electrodes facing each other and a light emitting layer including a light emitting compound interposed between the electrodes. When current flows between the electrodes, the light emitting compound produces light. A display device using the light emitting device does not need a separate light source device, and thus may decrease the weight, size or thickness of the display device. Further, the display device using the light emitting device has advantages in that the viewing angle, the contrast ratio, the color reproducibility, and the like are excellent and power consumption is low as compared to a display device using a backlight and a liquid crystal.

The light emitting device may further include a hole transporting layer disposed between an anode and a light emitting layer. The hole transporting layer may stabilize the interface between the anode and the light emitting layer, and minimize an energy barrier between the anode and the light emitting layer.

However, the light emitting device still has problems in that the lifespan of light emission is short and the power efficiency is low. In order to solve these problems, various compounds have been developed as a material for the light emitting device, but there is a limitation in manufacturing a light emitting device which satisfies both the lifespan of light emission and the power efficiency.

SUMMARY OF THE INVENTION

Technical Problem

Thus, a technical problem of the present invention has been contrived in view of these circumstances, and an object of the present invention is to provide a novel compound for improving the hole injection and transport properties in a light emitting device.

Another object of the present invention is to provide a light emitting device including the compound.

Still another object of the present invention is to provide an electronic device including the light emitting device.

Technical Solution

A compound according to an exemplary embodiment for realizing the object of the present invention is represented by the following Formula 1.

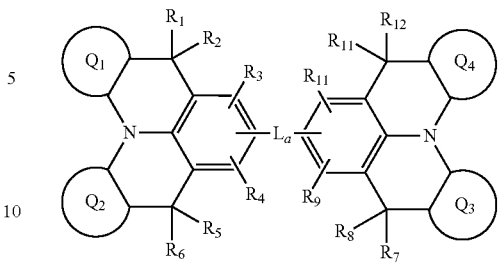

[Formula 1]

In Formula 1, $L_a$ represents *-$L_1$-$L_2$-$L_3$-$L_4$-*, $L_1$, $L_2$, $L_3$, and $L_4$ each independently represent a single bond, —O—, —S—, an arylene group having 6 to 60 carbon atoms, a heteroarylene group having 2 to 60 carbon atoms, an alkenylene group having 2 to 60 carbon atoms, a cycloalkylene group having 3 to 60 carbon atoms, or a heterocycloalkylene group having 2 to 60 carbon atoms, $Q_1$, $Q_2$, $Q_3$, and $Q_4$ each independently represent an aryl group having 6 to 60 carbon atoms or a heteroaryl group having 2 to 60 carbon atoms, which is unsubstituted or substituted with one or more selected from the group consisting of an alkyl group having 1 to 12 carbon atoms, an alkoxy group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, and an alkenyl group having 2 to 12 carbon atoms, $R_1$, $R_2$, $R_3$, $R_4$, $R_5$, $R_6$, $R_7$, $R_8$, $R_9$, $R_{10}$, $R_{11}$, and $R_{12}$ each independently represent hydrogen, an alkyl group having 1 to 6 carbon atoms, an alkoxy group having 1 to 6 carbon atoms, an aryl group having 6 to 20 carbon atoms, or a heteroaryl group having 2 to 20 carbon atoms, and hydrogen atoms of $Q_1$, $Q_2$, $Q_3$, $Q_4$, $L_a$, $R_1$, $R_2$, $R_3$, $R_4$, $R_5$, $R_6$, $R_7$, $R_8$, $R_9$, $R_{10}$, $R_{11}$, and $R_{12}$ of Formula 1 are each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

A light emitting device according to an exemplary embodiment for realizing the aforementioned another object of the present invention includes a first electrode, a second electrode, a light emitting layer, and an organic layer including the compound represented by Formula 1. The first electrode and the second electrode face each other, the light emitting layer is interposed between the first electrode and the second electrode, and the organic layer is disposed between the first electrode and the light emitting layer.

In an exemplary embodiment, the organic layer may be a hole transport layer. In this case, the organic layer may further include a P-type dopant.

In an exemplary embodiment, the organic layer may be a hole transport layer including a first layer including the compound and the P-type dopant, and a second layer including the compound. For example, the first layer may be disposed between the first electrode and the light emitting layer, and the second layer may be disposed between the first layer and the light emitting layer. In this case, the second layer may further include a dopant which is substantially the same as or different from the P-type dopant of the first layer.

In an exemplary embodiment, the light emitting device may further include a blocking layer disposed between the organic layer and the light emitting layer. In this case, the organic layer may be a hole transport layer.

In an exemplary embodiment, the light emitting device may further include a hole transport layer disposed between the organic layer and the first electrode. In this case, the organic layer may be a blocking layer.

An electronic device according to an exemplary embodiment for realizing the aforementioned still another object of the present invention may include a hole transport layer including the compound represented by Formula 1.

Effect of the Invention

According to the novel compound, the light emitting device including the same, and the electronic device, the novel compound of the present invention may improve the hole injection and transport properties in a light emitting device. Further, the novel compound of the present invention may minimize the non-radiative decay of an exciton produced in a light emitting layer. By using the novel compound according to the present invention in a light emitting device, it is possible to improve the light emitting efficiency of the light emitting device and increase the lifespan of the light emitting device.

BRIEF DESCRIPTION OF DRAWINGS

FIG. 1 is a cross-sectional view for describing a light emitting device according to an exemplary embodiment of the present invention.

FIG. 2 is a cross-sectional view for describing a light emitting device according to another exemplary embodiment of the present invention.

FIG. 3 is a cross-sectional view for describing a light emitting device according to still another exemplary embodiment of the present invention.

DETAILED DESCRIPTION OF THE INVENTION

Hereinafter, a novel compound according to the present invention will be first described, and a light emitting device including the compound will be described in more detail with reference to the accompanying drawings.

The compound according to the present invention is represented by the following Formula 1.

[Formula 1]

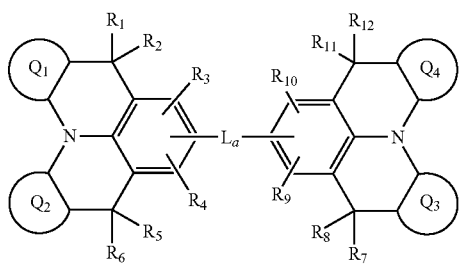

In Formula 1, $L_a$ represents *-$L_1$-$L_2$-$L_3$-$L_4$-*, $L_1$, $L_2$, $L_3$, and $L_4$ each independently represent a single bond, —O—, —S—, an arylene group having 6 to 60 carbon atoms, a heteroarylene group having 2 to 60 carbon atoms, an alkenylene group having 2 to 60 carbon atoms, a cycloalkylene group having 3 to 60 carbon atoms, or a heterocycloalkylene group having 2 to 60 carbon atoms, $Q_1$, $Q_2$, $Q_3$, and $Q_4$ each independently represent an aryl group having 6 to 60 carbon atoms or a heteroaryl group having 2 to 60 carbon atoms, which is unsubstituted or substituted with one or more selected from the group consisting of an alkyl group having 1 to 12 carbon atoms, an alkoxy group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, and an alkenyl group having 2 to 12 carbon atoms, and $R_1$, $R_2$, $R_3$, $R_4$, $R_5$, $R_6$, $R_7$, $R_8$, $R_9$, $R_{10}$, $R_{11}$, and $R_{12}$ each independently represent hydrogen, an alkyl group having 1 to 6 carbon atoms, an alkoxy group having 1 to 6 carbon atoms, an aryl group having 6 to 20 carbon atoms, or a heteroaryl group having 2 to 20 carbon atoms.

In this case, hydrogen atoms of $Q_1$, $Q_2$, $Q_3$, $Q_4$, $L_a$, $R_1$, $R_2$, $R_3$, $R_4$, $R_5$, $R_6$, $R_7$, $R_8$, $R_9$, $R_{10}$, $R_{11}$, and $R_{12}$ of Formula 1 are each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

In the present invention, "an aryl group" is defined as a monovalent substituent derived from an aromatic hydrocarbon.

Specific examples of the aryl group include a phenyl group, a naphthyl group, an anthracenyl group, a naphthacenyl group, a pyrenyl group, a tolyl group, a biphenyl group, a terphenyl group, a chrycenyl group, a spirobifluorenyl group, a fluoranthenyl group, a fluorenyl group, a perylenyl group, an indenyl group, an azulenyl group, a heptalenyl group, a phenalenyl group, a phenanthrenyl group, and the like.

"A heteroaryl group" represents "an aromatic heterocyclic ring" or "a heterocyclic" derived from a monocyclic or fused ring. The heteroaryl group may include at least one of nitrogen (N), sulfur (S), oxygen (O), phosphorus (P), selenium (Se), and silicon (Si) as a heteroatom.

Specific examples of the heteroaryl group include: a nitrogen-containing heteroaryl group including a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolinyl group, a quinolizinyl group, a phthalazinyl group, a naphthylidinyl group, a quinoxalinyl group, a quinazolinyl group, a cinnolinyl group, a pteridinyl group, an imidazotriazinyl group, an acridinyl group, a phenanthridinyl group, a carbazolyl group, a phenanthrolinyl group, a phenazinyl group, an imidazopyridinyl group, an imidazopyrimidinyl group, a pyrazolopyridinyl group, a fused-julolidinyl group represented by the following Formula 1-1 or a julolidinyl group represented by the following Formula 1-2, and the like; a sulfur-containing heteroaryl group including a thienyl group, a benzothienyl group, a dibenzothienyl group, and the like; an oxygen-containing heteroaryl group including a furyl group, a pyranyl group, a cyclopentapyranyl group, a benzofuranyl group, an isobenzofuranyl group, a dibenzofuranyl group, and the like; and the like. In addition, specific examples of the heteroaryl group include compounds including at least two heteroatoms, such as a thiazolyl group, an isothiazolyl group, a benzothiazolyl group, a benzothiadiazolyl group, a phenothiazinyl group, an isoxazolyl group, a furazanyl group, a phenoxazinyl group, an oxazolyl group, a benzoxazolyl group, an oxadiazolyl group, a pyrazoloxazolyl group, an imidazothiazolyl group, and a thienofuranyl group.

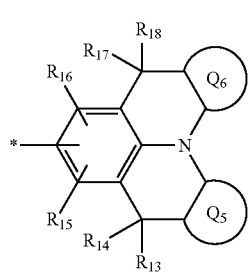

[Formula 1-1]

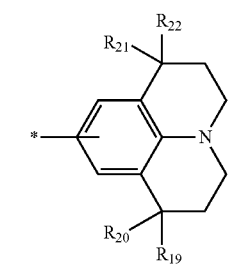

[Formula 1-2]

In Formula 1-1, $Q_5$ and $Q_6$ each independently represent an aryl group having 6 to 60 carbon atoms or a heteroaryl group having 2 to 60 carbon atoms, and $R_{13}$, $R_{14}$, $R_{15}$, $R_{16}$, $R_{17}$, and $R_{18}$ each independently represent hydrogen, an alkyl group having 1 to 6 carbon atoms, an alkoxy group having 1 to 6 carbon atoms, an aryl group having 6 to 20 carbon atoms, or a heteroaryl group having 2 to 20 carbon atoms.

In Formula 1-2, $R_{19}$, $R_{20}$, $R_{21}$, and $R_{22}$ each independently represent hydrogen, an alkyl group having 1 to 6 carbon atoms, an alkoxy group having 1 to 6 carbon atoms, an aryl group having 6 to 20 carbon atoms, or a heteroaryl group having 2 to 20 carbon atoms.

The "alkyl group" is defined as a functional group derived from a linear or branched, saturated hydrocarbon.

Specific examples of the alkyl group include a methyl group, an ethyl group, an n-propyl group, an iso-propyl group, an n-butyl group, a sec-butyl group, a tert-butyl group, an n-pentyl group, a 1,1-dimethylpropyl group, a 1,2-dimethylpropyl group, a 2,2-dimethylpropyl group, a 1-ethylpropyl group, a 2-ethylpropyl group, an n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like.

Further, "an arylene group" may mean a divalent substituent derived from the aryl group described above.

In addition, "a heteroarylene group" may mean a divalent substituent derived from the heteroaryl group described above. In the present invention, when "the heteroarylene group" includes a carbazole structure, the heteroarylene group is defined to include a structure represented by the following Linking Group 1 or the following Linking Group 2.

<Linking Group 1>

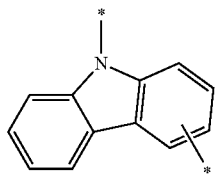

<Linking Group 2>

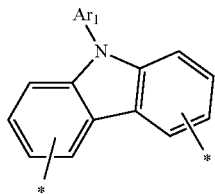

In Linking Group 2, $Ar_1$ represents *-$A_1$-$A_2$-$A_3$-$A_4$, $A_1$, $A_2$, and $A_3$ each independently represent a single bond, —O—, —S—, an arylene group having 6 to 30 carbon atoms, a heteroarylene group having 2 to 30 carbon atoms, an alkenylene group having 2 to 30 carbon atoms, a cycloalkylene group having 3 to 30 carbon atoms, or a heterocycloalkylene group having 2 to 30 carbon atoms, and $A_4$ may represent an alkyl group having 1 to 12 carbon atoms, an alkoxy group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, or an alkenyl group having 2 to 12 carbon atoms.

In this case, hydrogen atoms of Linking Group 1 or Linking Group 2 may be each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

In an exemplary embodiment, the compound represented by Formula 1 may include a compound represented by the following Formula 2.

[Formula 2]

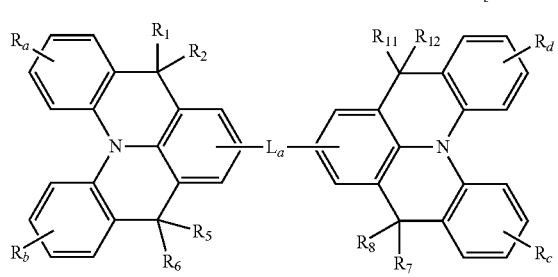

In Formula 2, $L_a$ represents *-$L_1$-$L_2$-$L_3$-$L_4$-*, $L_1$, $L_2$, $L_3$, and $L_4$ each independently represent a single bond, —O—, —S—, an arylene group having 6 to 30 carbon atoms, a heteroarylene group having 2 to 30 carbon atoms, an alkenylene group having 2 to 30 carbon atoms, a cycloalkylene group having 3 to 30 carbon atoms, or a heterocycloalkylene group having 2 to 30 carbon atoms, $R_a$, $R_b$, $R_c$, and $R_d$ each independently represent hydrogen, an alkyl group having 1 to 12 carbon atoms, an alkoxy group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, or an alkenyl group having 2 to 12 carbon atoms, $R_1$, $R_2$, $R_5$, $R_6$, $R_7$, $R_8$, $R_{11}$, and $R_{12}$ each independently represent hydrogen, an alkyl group having 1 to 6 carbon atoms, an alkoxy group having 1 to 6 carbon atoms, an aryl group having 6 to 20 carbon atoms, or a heteroaryl group having 2 to 20 carbon atoms, and hydrogen atoms of $R_a$, $R_b$, $R_c$, $R_d$, $L_a$, $R_1$, $R_2$, $R_5$, $R_6$, $R_7$, $R_8$, $R_{11}$, and $R_{12}$ of Formula 2 are each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

In Formula 2, $L_1$, $L_2$, $L_3$, and $L_4$ of $L_a$ may be each independently selected from a single bond, or the structures of Substituents 1 to 7 shown in the following Table 1.

TABLE 1

| No. | Substituent structure |
|---|---|
| 1 | ![benzene] |
| 2 | ![carbazole with $Ar_1$] |
| 3 | ![carbazole] |
| 4 | ![fluorene with $Ar_2$, $Ar_3$] |
| 5 | ![silafluorene with $Ar_4$, $Ar_5$] |
| 6 | ![dibenzothiophene] |
| 7 | ![dibenzofuran] |

In Table 1, $Ar_1$ of Substituent No. 2 represents *-$A_1$-$A_2$-$A_3$-$A_4$, $A_1$, $A_2$, and $A_3$ may each independently represent a single bond, an arylene group having 6 to 30 carbon atoms, or a heteroarylene group having 2 to 30 carbon atoms, and $A_4$ may represent an alkyl group having 1 to 12 carbon atoms, an aryl group having 6 to 30 carbon atoms, or a heteroaryl group having 2 to 30 carbon atoms.

In Table 1, $Ar_e$ and $Ar_a$ of Substituent No. 4 and $Ar_4$ and $Ar_5$ of Substituent No. 5 may each independently represent an alkyl group having 1 to 12 carbon atoms, an aryl group having 6 to 30 carbon atoms, or a heteroaryl group having 2 to 30 carbon atoms.

In each case of the substituents in Table 1, benzene rings adjacent to each other may be all linked at the para position, and thus, may be linked to each other to have entirely a linear type. In contrast, a plurality of benzene rings may be linked to each other not to be limited only to the para position, and thus, $L_a$ of Formula 2 may also have entirely a bended form.

For example, Substituent No. 1 in Table 1 may be represented by the following Formula 1-1a or the following Formula 1-1b.

<Formula 1-1a>

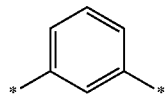
<Formula 1-1b>

Furthermore, Substituent No. 2 in Table 1 may be represented by the following Formula 1-2a or the following Formula 1-2b.

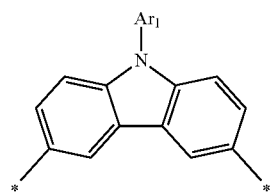
<Formula 1-2a>

<Formula 1-2b>

Further, Substituent No. 3 in Table 1 may be represented by the following Formula 1-3a or the following Formula 1-3b.

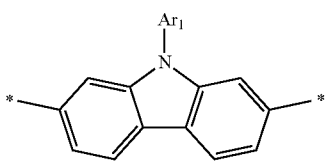
<Formula 1-3a>

<Formula 1-3b>

Substituent No. 5 in Table 1 may be represented by the following Formula 1-5a or the following Formula 1-5b.

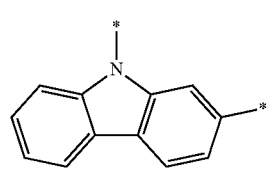
<Formula 1-5a>

<Formula 1-5b>
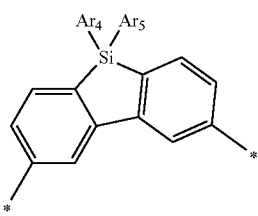

Substituent No. 6 in Table 1 may be represented by the following Formula 1-6a or the following Formula 1-6b.

<Formula 1-6a>
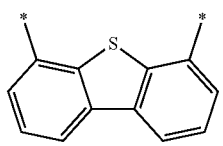

<Formula 1-6b>
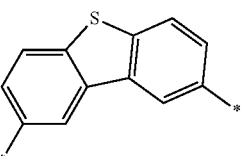

In addition, Substituent No. 7 in Table 1 may be represented by the following Formula 1-7a or the following Formula 1-7b.

<Formula 1-7a>
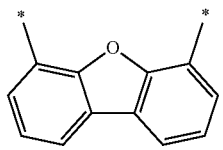

<Formula 1-7b>
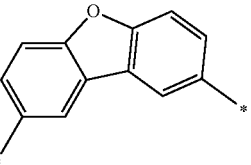

In Formula 2, $R_a$, $R_b$, $R_c$, and $R_d$ may be each independently selected from hydrogen or the structures of Substituents 8 to 10 represented by the following Table 2.

TABLE 2

| No. | Substituent structure |
|---|---|
| 8 | 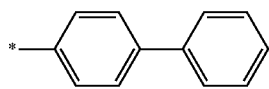 [SMILES: *c1ccc(-c2ccccc2)cc1] |
| 9 | 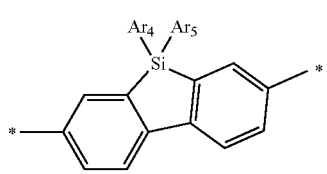 |

TABLE 2-continued

| No. | Substituent structure |
|---|---|
| 10 | *—(2-naphthyl) |

Substituent No. 10 in Table 2 may be specifically represented by the following Formula 2-10a or the following Formula 2-10b.

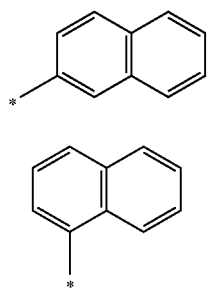

<Formula 2-10a>

<Formula 2-10b>

In this case, in Formula 2, $R_1$, $R_2$, $R_5$, $R_6$, $R_7$, $R_8$, $R_{11}$, and $R_{12}$ may be each independently selected from hydrogen, a methyl group, or a phenyl group.

In an exemplary embodiment, the compound represented by Formula 1 may include a compound represented by the following Formula 3.

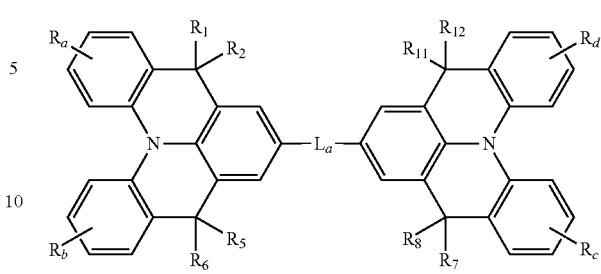

[Formula 3]

In Formula 3, $L_a$ represents a single bond, an arylene group having 6 to 30 carbon atoms, or a heteroarylene group having 2 to 30 carbon atoms, $R_a$, $R_b$, $R_c$, and $R_d$ each independently represent hydrogen, an alkyl group having 1 to 12 carbon atoms, an alkoxy group having 1 to 12 carbon atoms, an aryl group having 6 to 30 carbon atoms, or a heteroaryl group having 2 to 30 carbon atoms, $R_1$, $R_2$, $R_5$, $R_6$, $R_7$, $R_8$, $R_{11}$, and $R_{12}$ each independently represent hydrogen, an alkyl group having 1 to 6 carbon atoms, or an alkoxy group having 1 to 6 carbon atoms, and hydrogen atoms of $L_a$, $R_1$, $R_2$, $R_5$, $R_6$, $R_7$, $R_8$, $R_{11}$, $R_{12}$, $R_a$, $R_b$, $R_c$, and $R_d$ of Formula 3 may be each independently unsubstituted or substituted with an alkyl group having 1 to 6 carbon atoms, an alkenyl group having 1 to 6 carbon atoms, an alkoxy group having 1 to 6 carbon atoms, an aryl group having 6 to 20 carbon atoms, or a heteroaryl group having 2 to 20 carbon atoms.

The compound represented by Formula 1 according to the present invention may be selected from the compounds shown in Structures 1 to 112 of the following Table 3.

TABLE 3

| No. | Structure |
|---|---|
| 1 | (structure shown) |
| 2 | (structure shown) |

TABLE 3-continued

| No. | Structure |
|---|---|
| 3 | 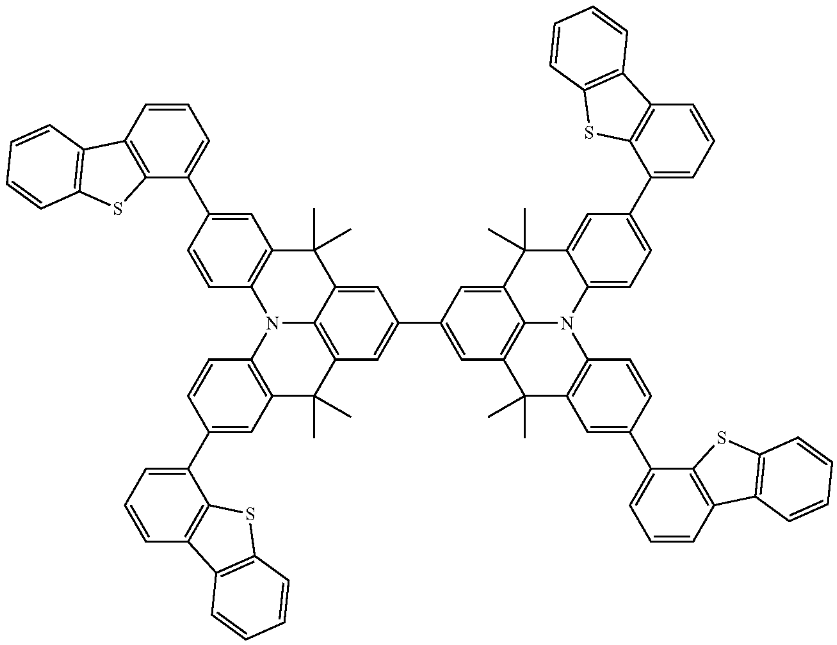 |
| 4 | 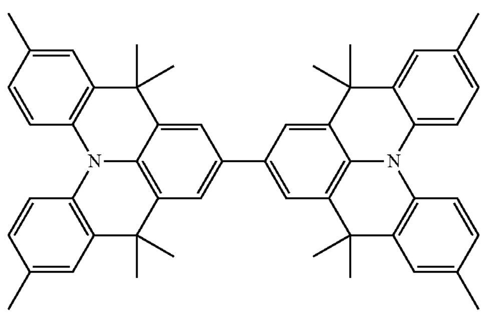 [SMILES: Cc1ccc2c(c1)C(C)(C)c1cc(-c3cc4c5c(c3)C(C)(C)c3cc(C)ccc3N5c3ccc(C)cc3C4(C)C)cc3c1N2c1ccc(C)cc1C3(C)C] |
| 5 | 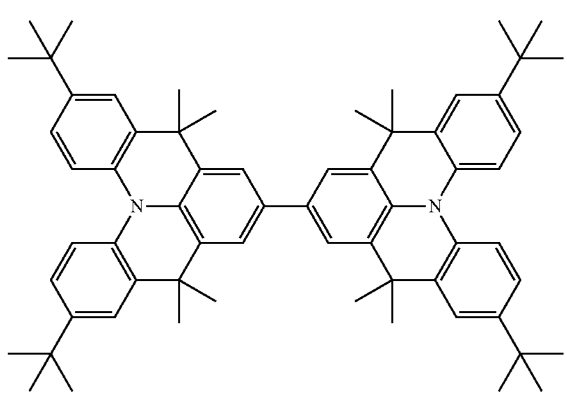 [SMILES: CC(C)(C)c1ccc2c(c1)C(C)(C)c1cc(-c3cc4c5c(c3)C(C)(C)c3cc(C(C)(C)C)ccc3N5c3ccc(C(C)(C)C)cc3C4(C)C)cc3c1N2c1ccc(C(C)(C)C)cc1C3(C)C] |

TABLE 3-continued
| No. | Structure |
|---|---|
| 6 | 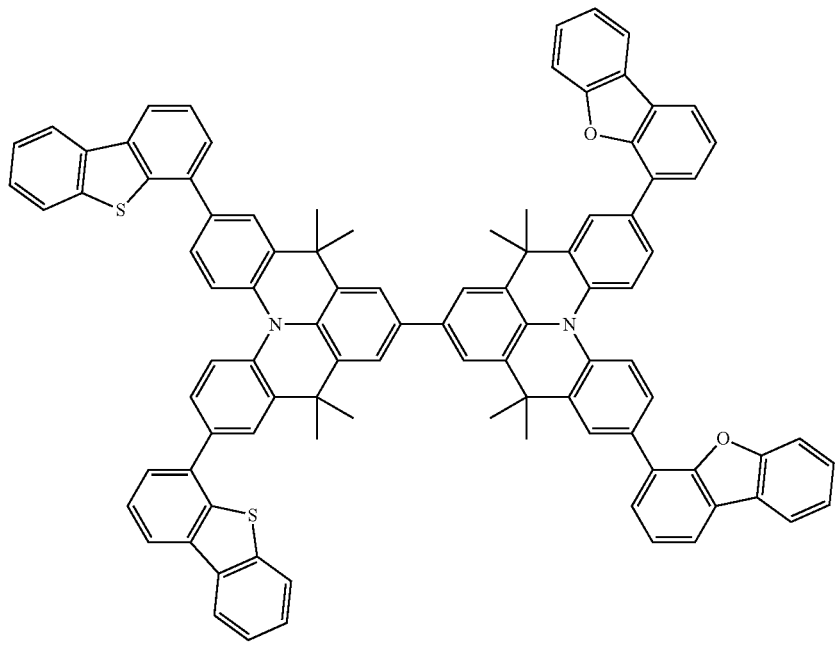 [SMILES: CC1(C)c2cc(-c3cccc4c3oc3ccccc34)ccc2N2c3ccc(-c4cccc5c4oc4ccccc45)cc3C(C)(C)c3cc(-c4cc5c6c(c4)C(C)(C)c4cc(-c7cccc8c7sc7ccccc78)ccc4N6c4ccc(-c6cccc7c6sc6ccccc67)cc4C5(C)C)cc1c32] |
| 7 | 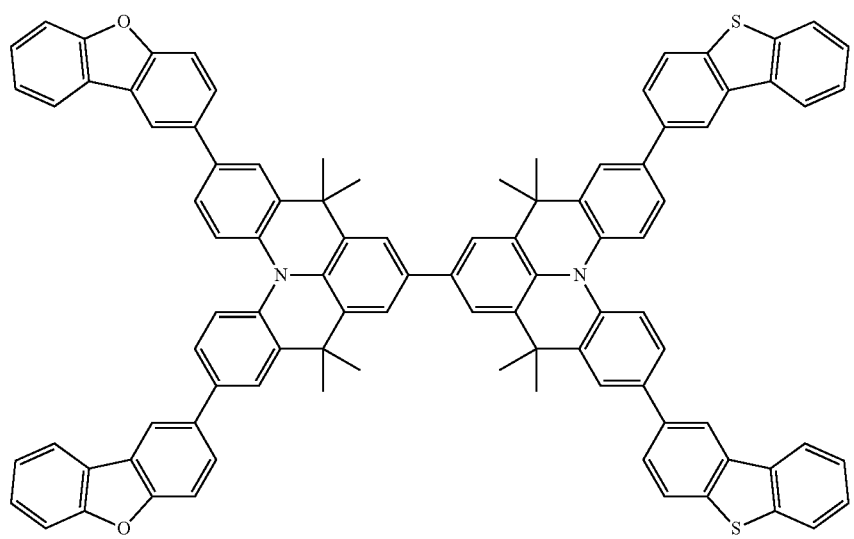 |

TABLE 3-continued
| No. | Structure |
|---|---|
| 8 | 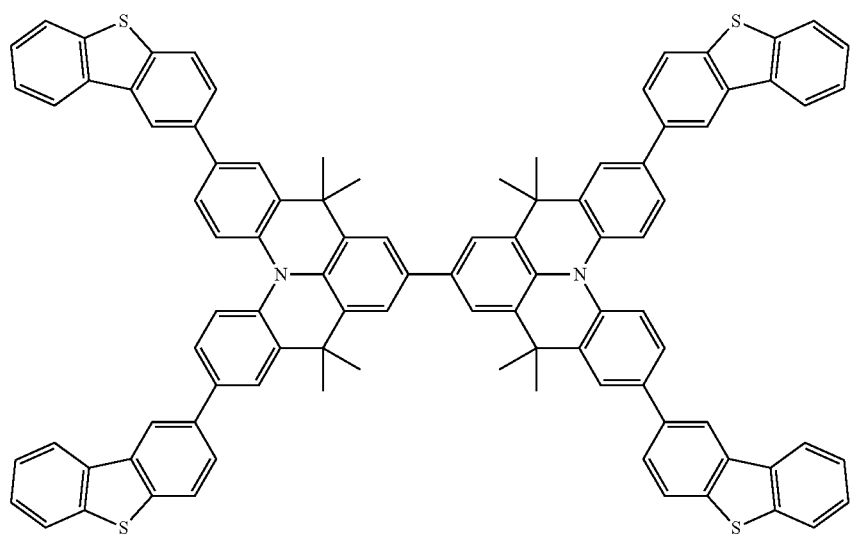 [SMILES: CC1(C)c2cc(-c3ccc4oc5ccccc5c4c3)ccc2N2c3ccc(-c4ccc5oc6ccccc6c5c4)cc3C(C)(C)c3cc(-c4cc5c6c(c4)C(C)(C)c4cc(-c7ccc8sc9ccccc9c8c7)ccc4N6c4ccc(-c6ccc7sc8ccccc8c7c6)cc4C5(C)C)cc1c32] |
| 9 | 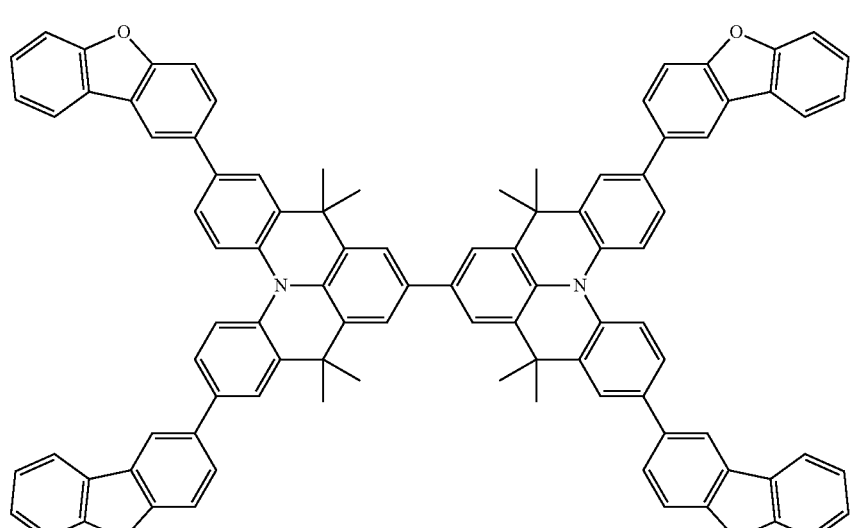 |

TABLE 3-continued

| No. | Structure |
|---|---|
| 10 | 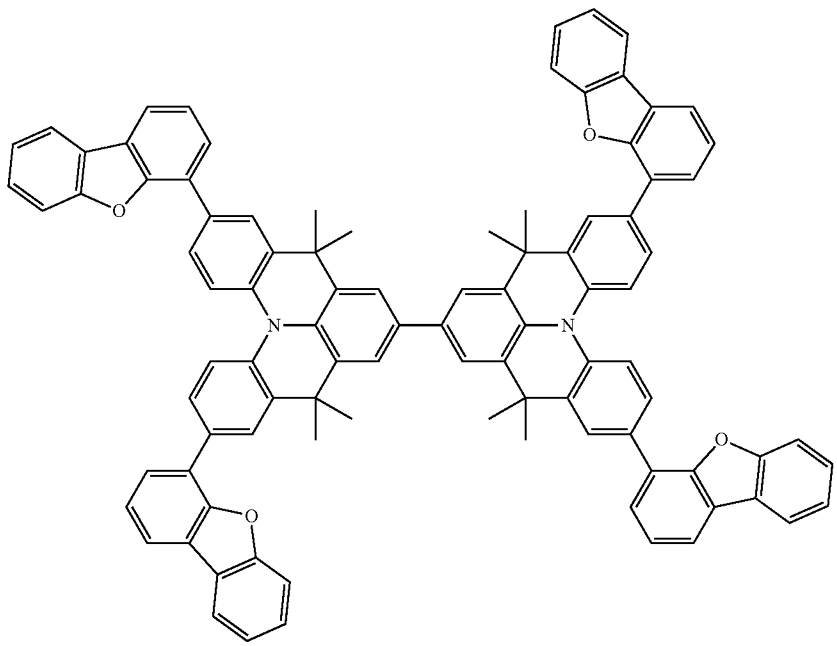 |
| 11 | 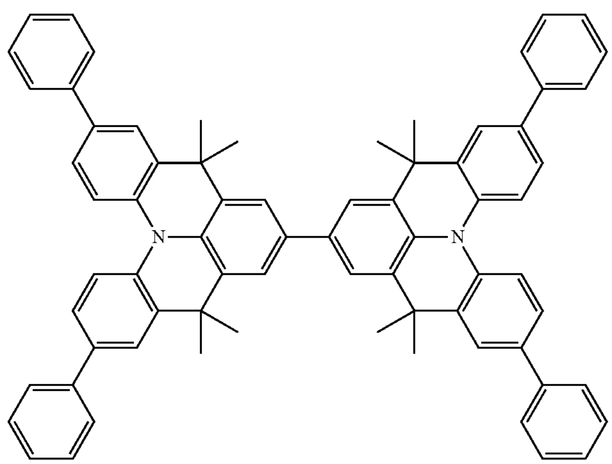 [SMILES: CC1(C)c2cc(-c3ccccc3)ccc2N2c3ccc(-c4ccccc4)cc3C(C)(C)c3cc(-c4cc5c6c(c4)C(C)(C)c4cc(-c7ccccc7)ccc4N6c4ccc(-c6ccccc6)cc4C5(C)C)cc1c32] |
| 12 | 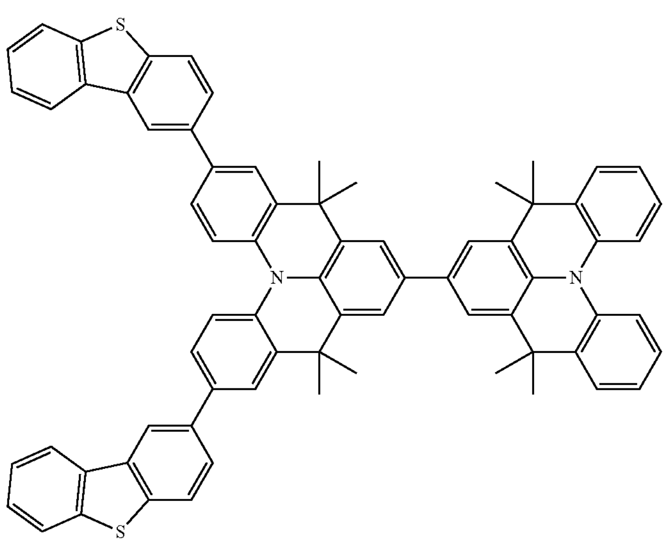 [SMILES: CC1(C)c2ccccc2N2c3ccccc3C(C)(C)c3cc(-c4cc5c6c(c4)C(C)(C)c4cc(-c7ccc8oc9ccccc9c8c7)ccc4N6c4ccc(-c6ccc7oc8ccccc8c7c6)cc4C5(C)C)cc1c32] |

TABLE 3-continued
| No. | Structure |
|---|---|
| 13 | 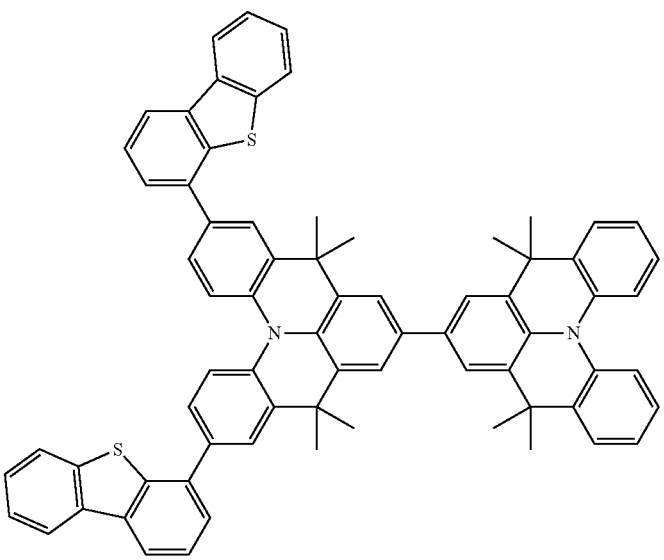 |
| 14 | 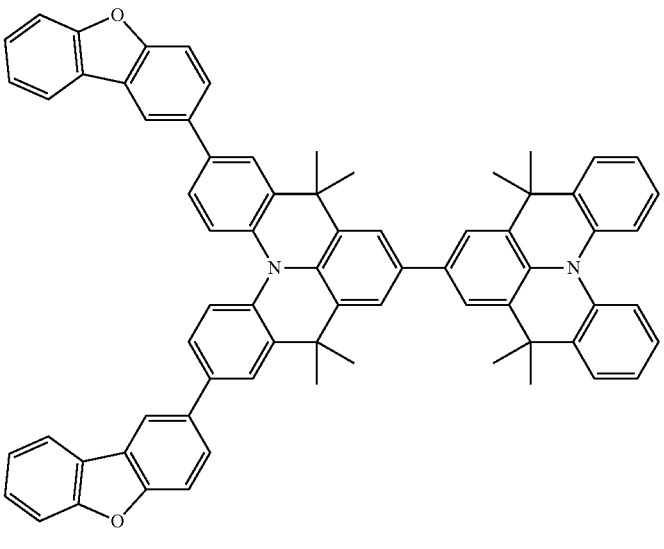 |

TABLE 3-continued
| No. | Structure |
|---|---|
| 15 | 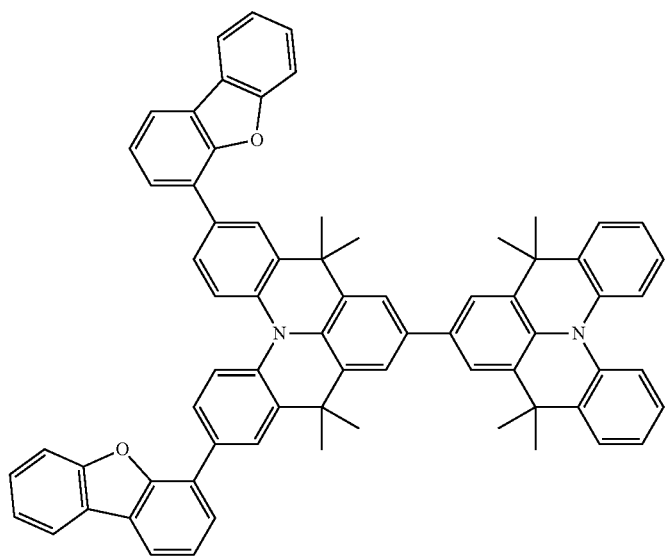 [SMILES: CC1(C)c2ccccc2N2c3ccccc3C(C)(C)c3cc(-c4cc5c6c(c4)C(C)(C)c4cc(-c7cccc8c7oc7ccccc78)ccc4N6c4ccc(-c6cccc7c6oc6ccccc67)cc4C5(C)C)cc1c32] |
| 16 | 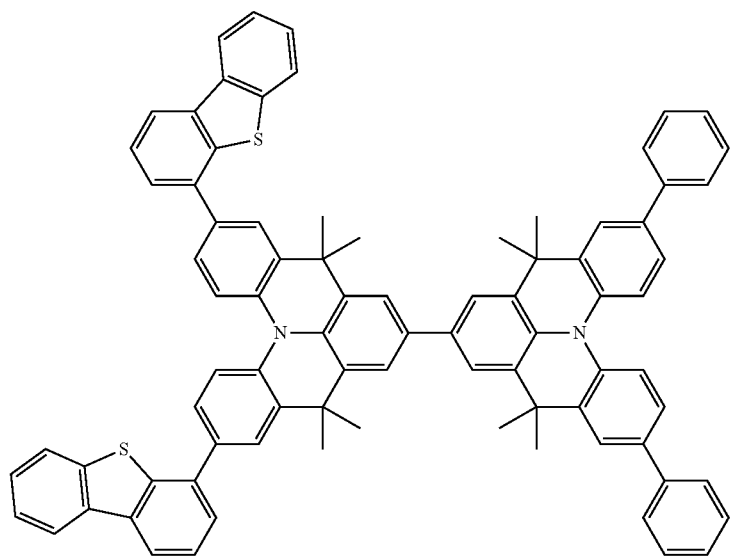 [SMILES: CC1(C)c2cc(-c3ccccc3)ccc2N2c3ccc(-c4ccccc4)cc3C(C)(C)c3cc(-c4cc5c6c(c4)C(C)(C)c4cc(-c7cccc8c7sc7ccccc78)ccc4N6c4ccc(-c6cccc7c6sc6ccccc67)cc4C5(C)C)cc1c32] |

TABLE 3-continued
| No. | Structure |
|---|---|
| 17 | 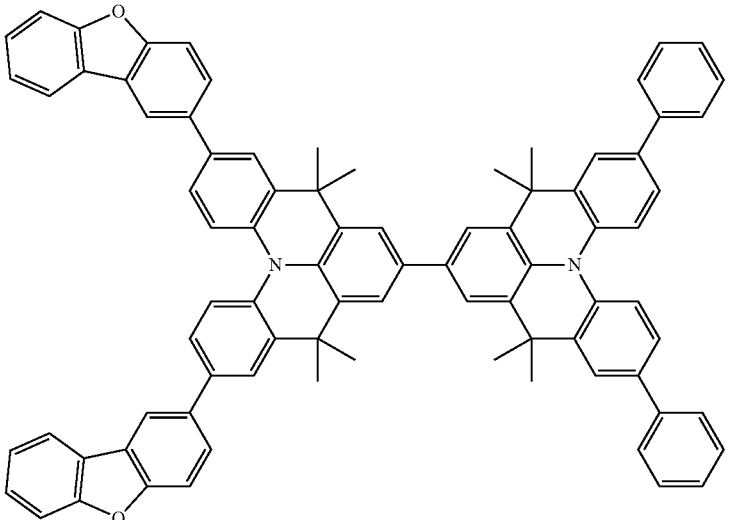 [SMILES: CC1(C)c2cc(-c3ccccc3)ccc2N2c3ccc(-c4ccccc4)cc3C(C)(C)c3cc(-c4cc5c6c(c4)C(C)(C)c4cc(-c7ccc8oc9ccccc9c8c7)ccc4N6c4ccc(-c6ccc7oc8ccccc8c7c6)cc4C5(C)C)cc1c32] |
| 18 | 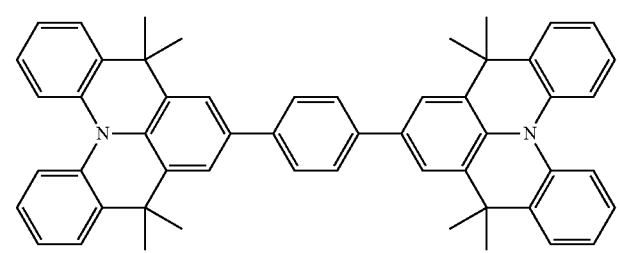 [SMILES: CC1(C)c2ccccc2N2c3ccccc3C(C)(C)c3cc(-c4ccc(-c5cc6c7c(c5)C(C)(C)c5ccccc5N7c5ccccc5C6(C)C)cc4)cc1c32] |
| 19 | 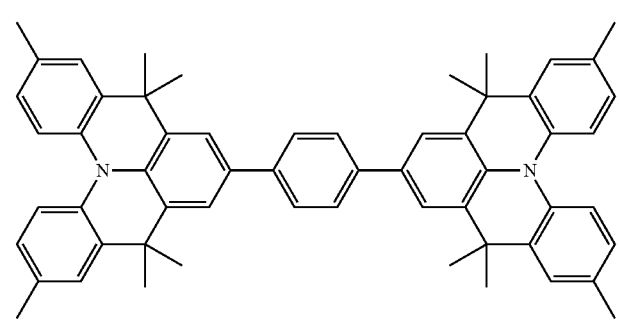 [SMILES: Cc1ccc2c(c1)C(C)(C)c1cc(-c3ccc(-c4cc5c6c(c4)C(C)(C)c4cc(C)ccc4N6c4ccc(C)cc4C5(C)C)cc3)cc3c1N2c1ccc(C)cc1C3(C)C] |
| 20 | 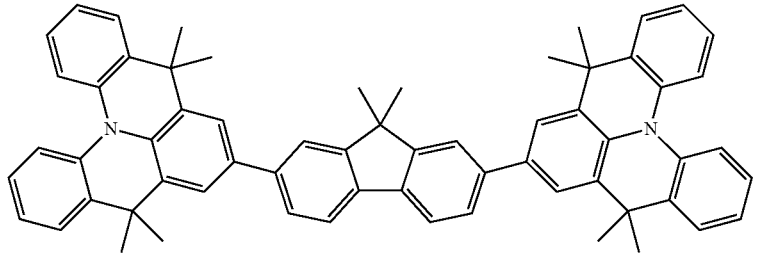 |

TABLE 3-continued

| No. | Structure |
|---|---|
| 21 | 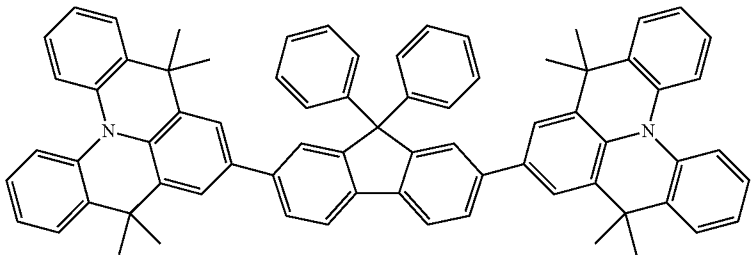 [SMILES: CC1(C)c2ccccc2N2c3ccccc3C(C)(C)c3cc(-c4ccc5c(c4)C(c4ccccc4)(c4ccccc4)c4cc(-c6cc7c8c(c6)C(C)(C)c6ccccc6N8c6ccccc6C7(C)C)ccc4-5)cc1c32] |
| 22 | 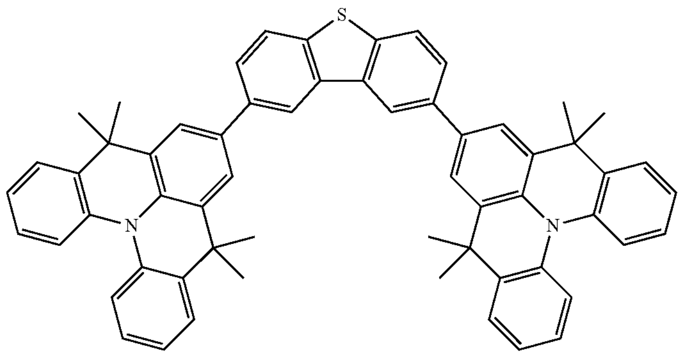 [SMILES: CC1(C)c2ccccc2N2c3ccccc3C(C)(C)c3cc(-c4ccc5sc6ccc(-c7cc8c9c(c7)C(C)(C)c7ccccc7N9c7ccccc7C8(C)C)cc6c5c4)cc1c32] |
| 23 | 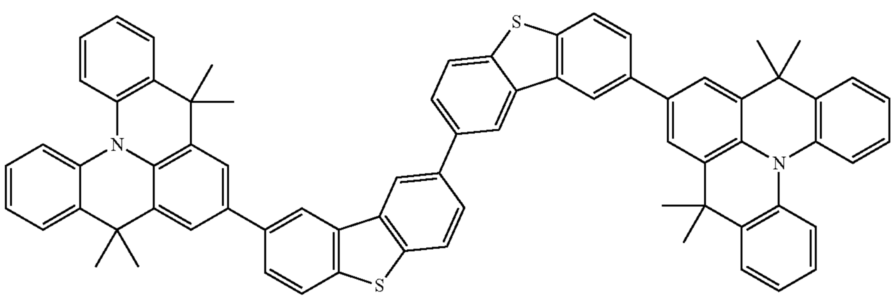 |
| 24 | 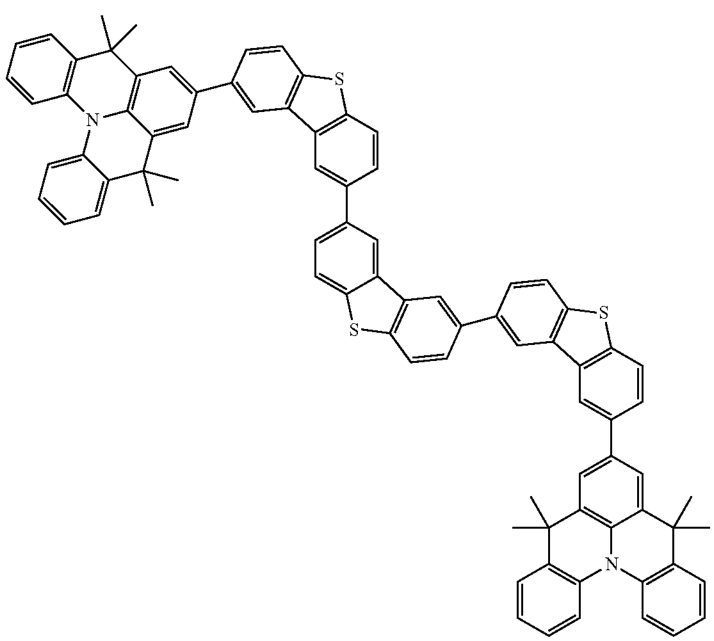 [SMILES: CC1(C)c2ccccc2N2c3ccccc3C(C)(C)c3cc(-c4ccc5sc6ccc(-c7ccc8sc9ccc(-c%10ccc%11sc%12ccc(-c%13cc%14c%15c(c%13)C(C)(C)c%13ccccc%13N%15c%13ccccc%13C%14(C)C)cc%12c%11c%10)cc9c8c7)cc6c5c4)cc1c32] |

TABLE 3-continued

| No. | Structure |
| --- | --- |
| 25 | 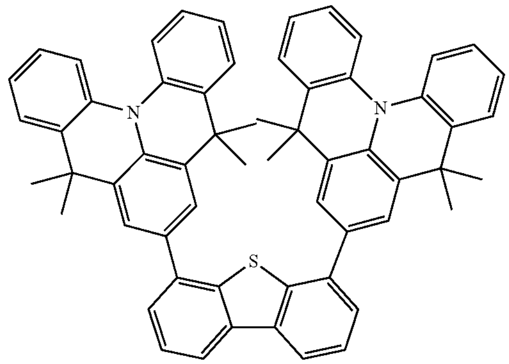 [SMILES: CC1(C)c2ccccc2N2c3ccccc3C(C)(C)c3cc(-c4cccc5c4sc4c(-c6cc7c8c(c6)C(C)(C)c6ccccc6N8c6ccccc6C7(C)C)cccc45)cc1c32] |
| 26 | 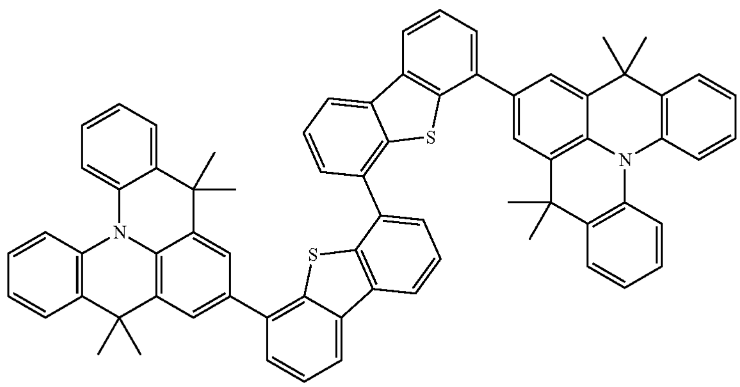 |
| 27 | 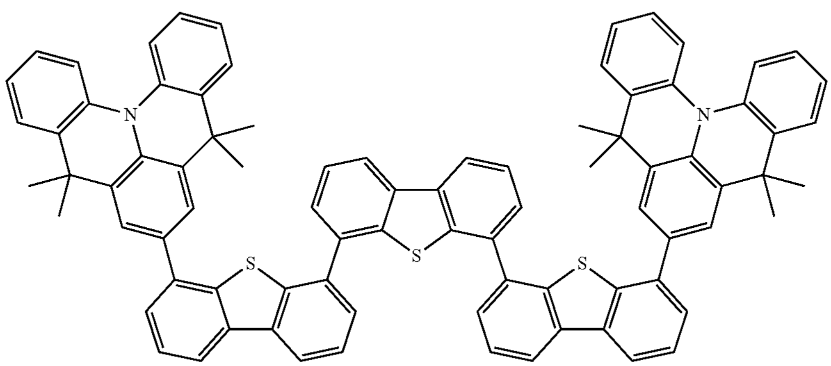 [SMILES: CC1(C)c2ccccc2N2c3ccccc3C(C)(C)c3cc(-c4cccc5c4sc4c(-c6cccc7c6sc6c(-c8cccc9c8sc8c(-c%10cc%11c%12c(c%10)C(C)(C)c%10ccccc%10N%12c%10ccccc%10C%11(C)C)cccc89)cccc67)cccc45)cc1c32] |
| 28 | 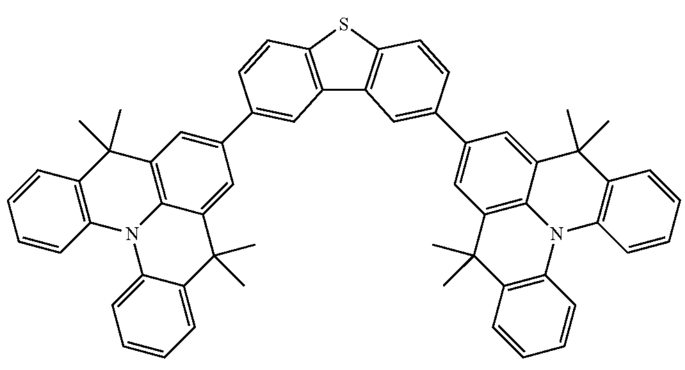 [SMILES: CC1(C)c2ccccc2N2c3ccccc3C(C)(C)c3cc(-c4ccc5sc6ccc(-c7cc8c9c(c7)C(C)(C)c7ccccc7N9c7ccccc7C8(C)C)cc6c5c4)cc1c32] |

TABLE 3-continued

| No. | Structure |
|-----|-----------|
| 29  | 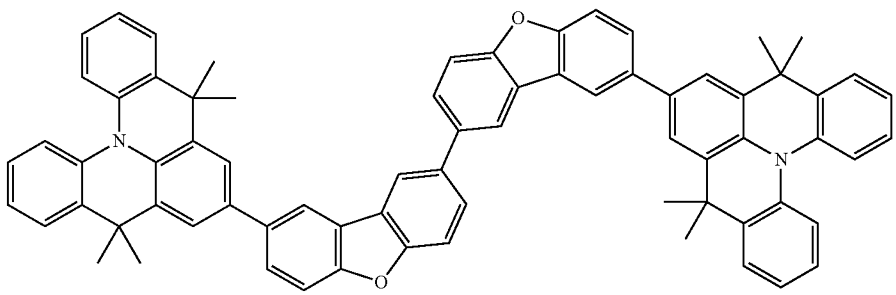          |
| 30  | 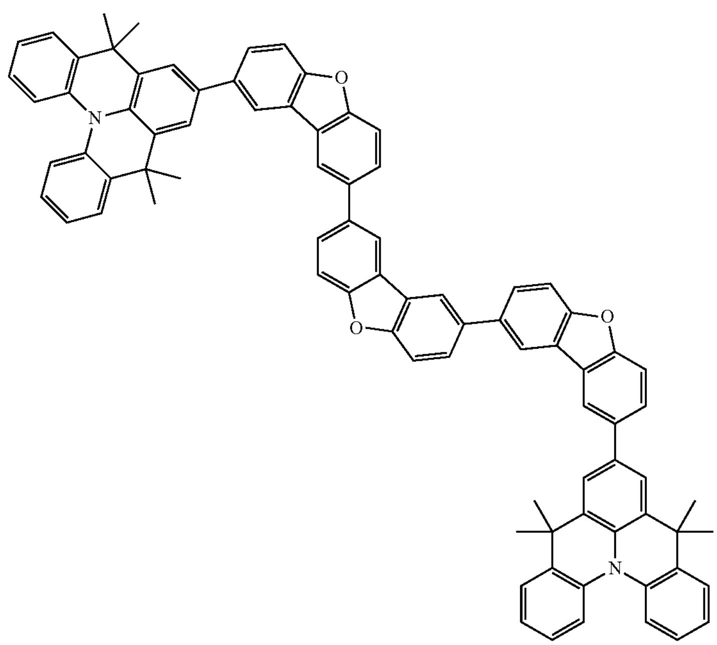 [SMILES: CC1(C)c2ccccc2N2c3ccccc3C(C)(C)c3cc(-c4ccc5oc6ccc(-c7ccc8oc9ccc(-c%10ccc%11oc%12ccc(-c%13cc%14c%15c(c%13)C(C)(C)c%13ccccc%13N%15c%13ccccc%13C%14(C)C)cc%12c%11c%10)cc9c8c7)cc6c5c4)cc1c32]          |
| 31  | 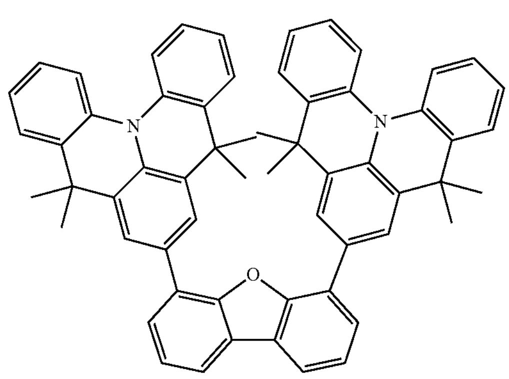 [SMILES: CC1(C)c2ccccc2N2c3ccccc3C(C)(C)c3cc(-c4cccc5c4oc4c(-c6cc7c8c(c6)C(C)(C)c6ccccc6N8c6ccccc6C7(C)C)cccc45)cc1c32]          |

TABLE 3-continued

| No. | Structure |
|---|---|
| 32 | 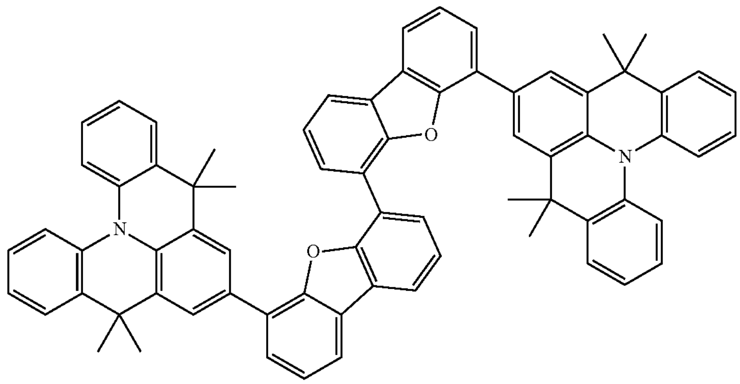 [SMILES: CC1(C)c2ccccc2N2c3ccccc3C(C)(C)c3cc(-c4cccc5c4oc4c(-c6cccc7c6oc6c(-c8cc9c%10c(c8)C(C)(C)c8ccccc8N%10c8ccccc8C9(C)C)cccc67)cccc45)cc1c32] |
| 33 | 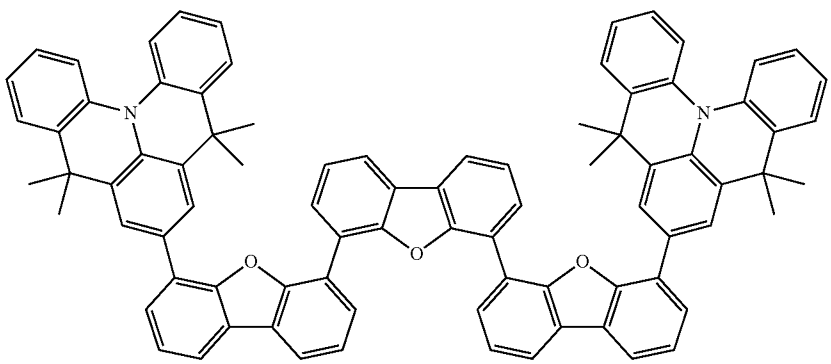 |
| 34 | 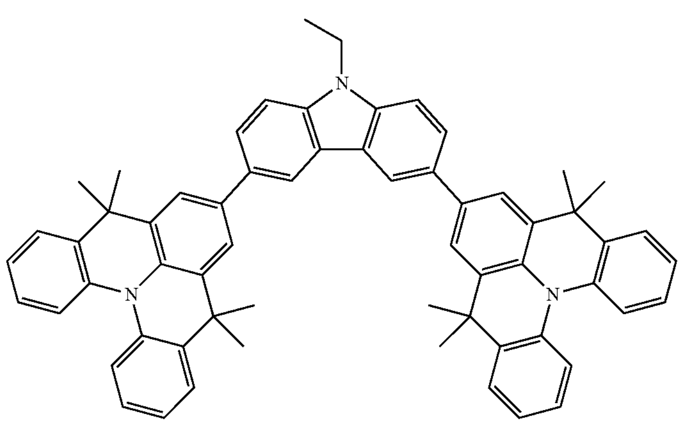 [SMILES: CCn1c2ccc(-c3cc4c5c(c3)C(C)(C)c3ccccc3N5c3ccccc3C4(C)C)cc2c2cc(-c3cc4c5c(c3)C(C)(C)c3ccccc3N5c3ccccc3C4(C)C)ccc21] |

TABLE 3-continued

| No. | Structure |
|---|---|
| 35 | 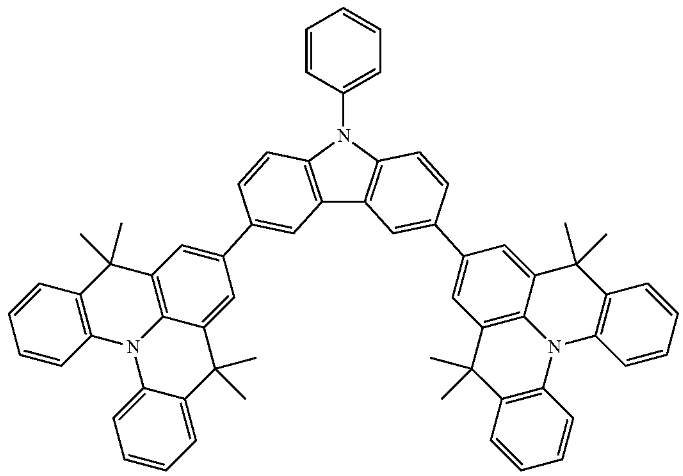 [SMILES: CC1(C)c2ccccc2N2c3ccccc3C(C)(C)c3cc(-c4ccc5c(c4)c4cc(-c6cc7c8c(c6)C(C)(C)c6ccccc6N8c6ccccc6C7(C)C)ccc4n5-c4ccccc4)cc1c32] |
| 36 | 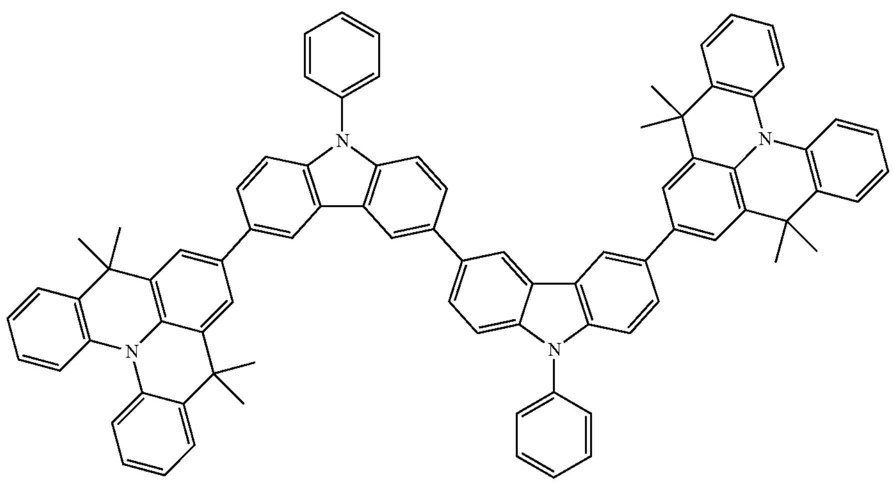 [SMILES: CC1(C)c2ccccc2N2c3ccccc3C(C)(C)c3cc(-c4ccc5c(c4)c4cc(-c6ccc7c(c6)c6cc(-c8cc9c%10c(c8)C(C)(C)c8ccccc8N%10c8ccccc8C9(C)C)ccc6n7-c6ccccc6)ccc4n5-c4ccccc4)cc1c32] |
| 37 | 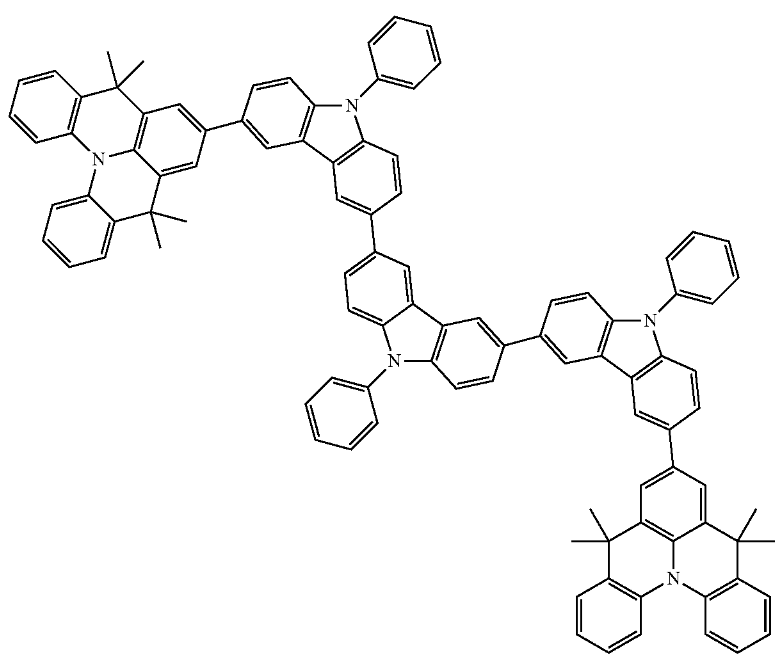 [SMILES: CC1(C)c2ccccc2N2c3ccccc3C(C)(C)c3cc(-c4ccc5c(c4)c4cc(-c6ccc7c(c6)c6cc(-c8ccc9c(c8)c8cc(-c%10cc%11c%12c(c%10)C(C)(C)c%10ccccc%10N%12c%10ccccc%10C%11(C)C)ccc8n9-c8ccccc8)ccc6n7-c6ccccc6)ccc4n5-c4ccccc4)cc1c32] |

TABLE 3-continued
| No. | Structure |
|---|---|
| 38 | 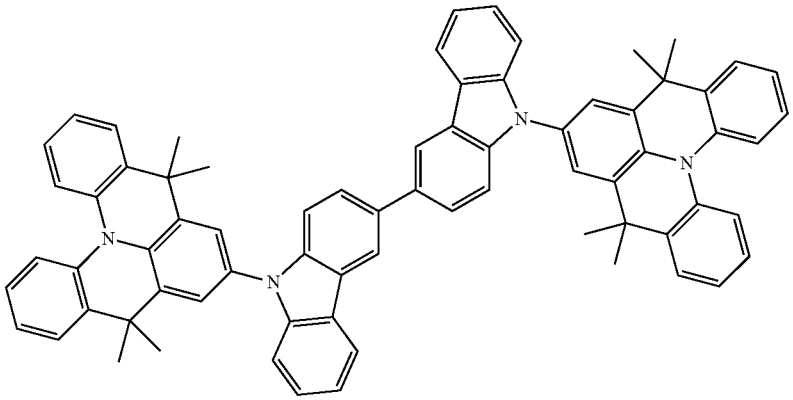 [SMILES: CC1(C)c2ccccc2N2c3ccccc3C(C)(C)c3cc(-n4c5ccccc5c5cc(-c6ccc7c(c6)c6ccccc6n7-c6cc7c8c(c6)C(C)(C)c6ccccc6N8c6ccccc6C7(C)C)ccc54)cc1c32] |
| 39 | 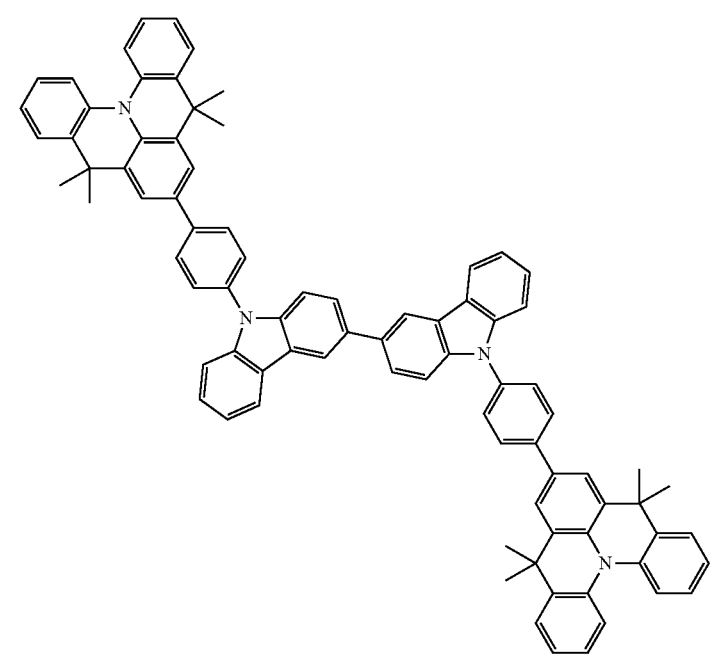 [SMILES: CC1(C)c2ccccc2N2c3ccccc3C(C)(C)c3cc(-c4ccc(-n5c6ccccc6c6cc(-c7ccc8c(c7)c7ccccc7n8-c7ccc(-c8cc9c%10c(c8)C(C)(C)c8ccccc8N%10c8ccccc8C9(C)C)cc7)ccc65)cc4)cc1c32] |

TABLE 3-continued
| No. | Structure |
|---|---|
| 40 | 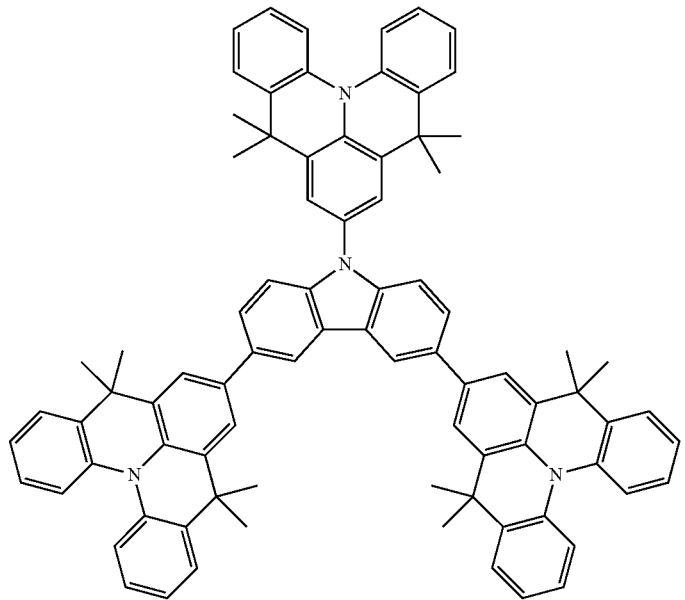 [SMILES: CC1(C)c2ccccc2N2c3ccccc3C(C)(C)c3cc(-c4ccc5c(c4)c4cc(-c6cc7c8c(c6)C(C)(C)c6ccccc6N8c6ccccc6C7(C)C)ccc4n5-c4cc5c6c(c4)C(C)(C)c4ccccc4N6c4ccccc4C5(C)C)cc1c32] |
| 41 | 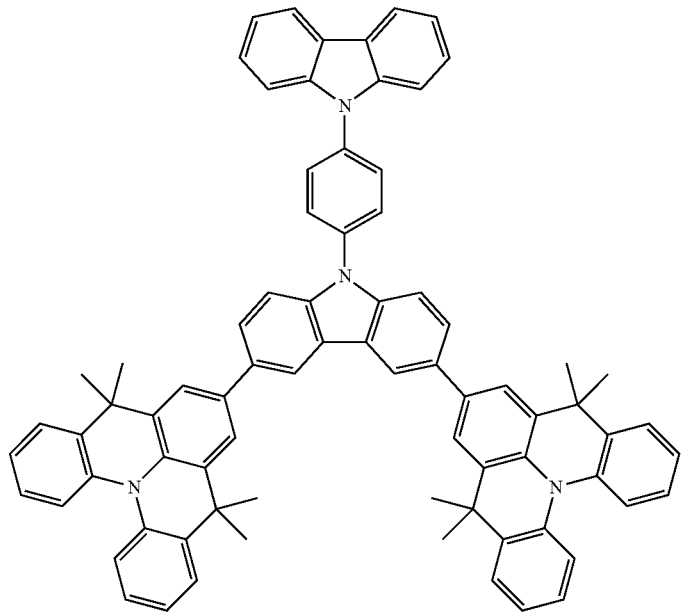 [SMILES: CC1(C)c2ccccc2N2c3ccccc3C(C)(C)c3cc(-c4ccc5c(c4)c4cc(-c6cc7c8c(c6)C(C)(C)c6ccccc6N8c6ccccc6C7(C)C)ccc4n5-c4ccc(-n5c6ccccc6c6ccccc65)cc4)cc1c32] |

TABLE 3-continued
| No. | Structure |
|---|---|
| 42 | 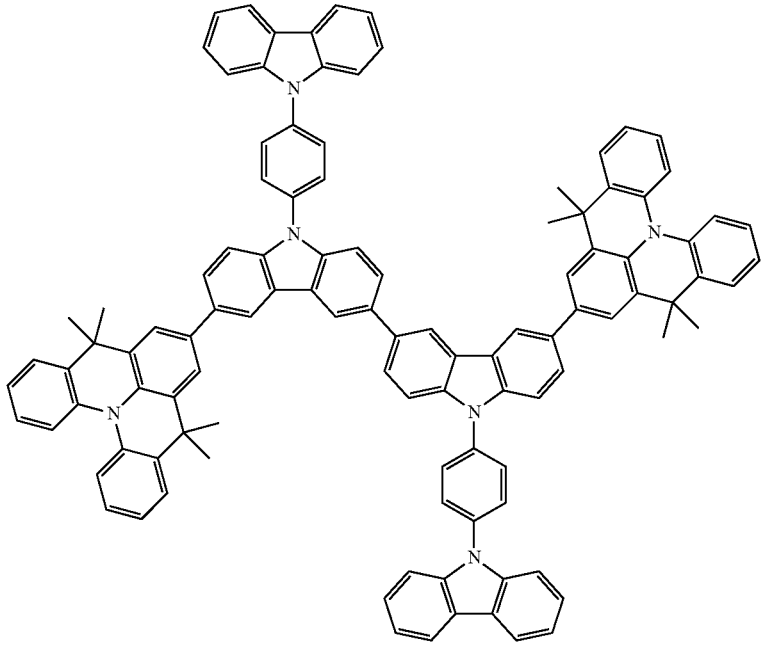 [SMILES: CC1(C)c2ccccc2N2c3ccccc3C(C)(C)c3cc(-c4ccc5c(c4)c4cc(-c6ccc7c(c6)c6cc(-c8cc9c%10c(c8)C(C)(C)c8ccccc8N%10c8ccccc8C9(C)C)ccc6n7-c6ccc(-n7c8ccccc8c8ccccc87)cc6)ccc4n5-c4ccc(-n5c6ccccc6c6ccccc65)cc4)cc1c32] |
| 43 | 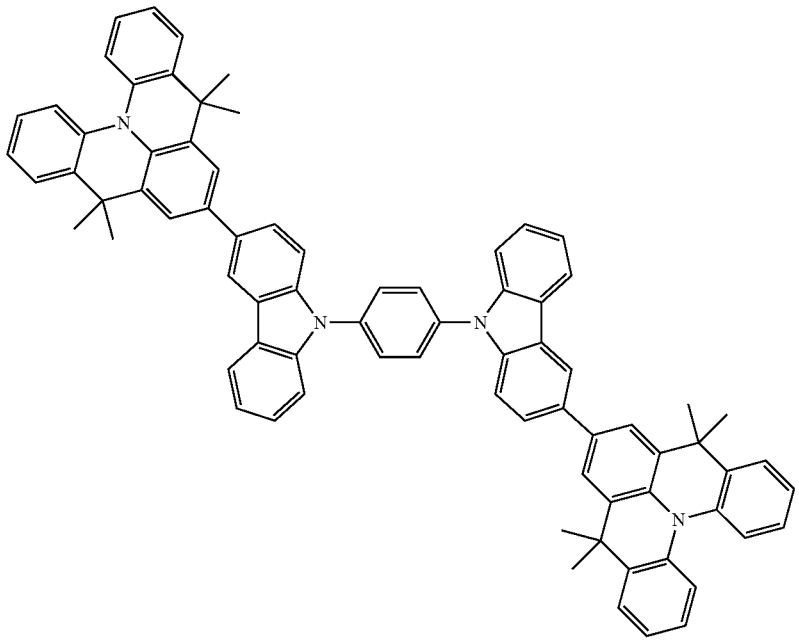 [SMILES: CC1(C)c2ccccc2N2c3ccccc3C(C)(C)c3cc(-c4ccc5c(c4)c4ccccc4n5-c4ccc(-n5c6ccccc6c6cc(-c7cc8c9c(c7)C(C)(C)c7ccccc7N9c7ccccc7C8(C)C)ccc65)cc4)cc1c32] |

TABLE 3-continued
| No. | Structure |
|-----|-----------|
| 44 | 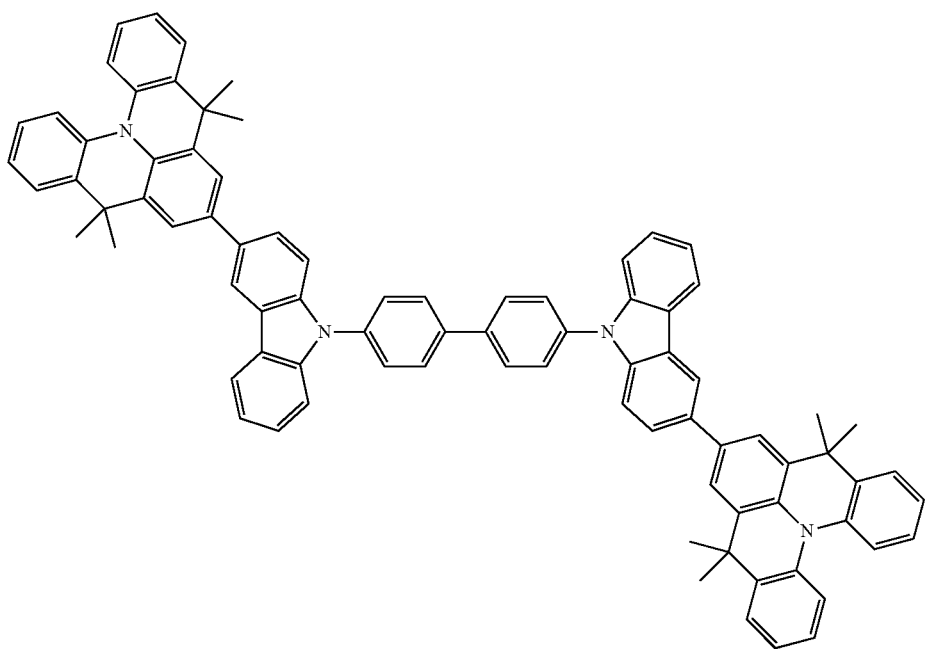 [SMILES: CC1(C)c2ccccc2N2c3ccccc3C(C)(C)c3cc(-c4ccc5c(c4)c4ccccc4n5-c4ccc(-c5ccc(-n6c7ccccc7c7cc(-c8cc9c%10c(c8)C(C)(C)c8ccccc8N%10c8ccccc8C9(C)C)ccc76)cc5)cc4)cc1c32] |
| 45 | 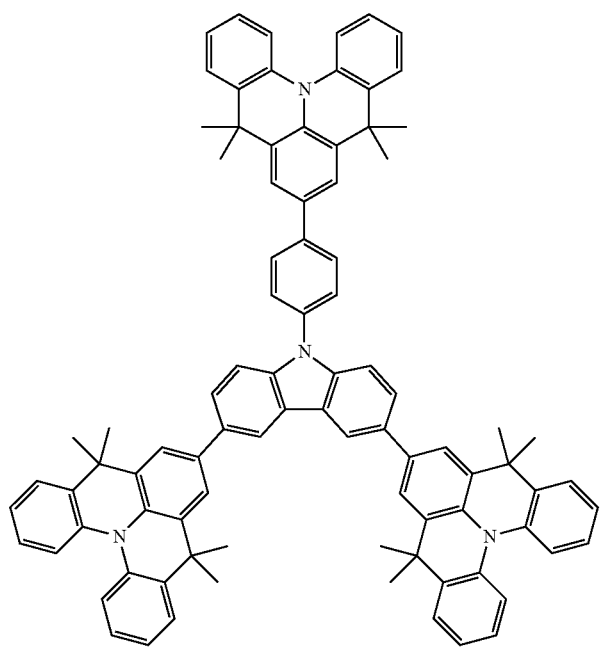 [SMILES: CC1(C)c2ccccc2N2c3ccccc3C(C)(C)c3cc(-c4ccc(-n5c6ccc(-c7cc8c9c(c7)C(C)(C)c7ccccc7N9c7ccccc7C8(C)C)cc6c6cc(-c7cc8c9c(c7)C(C)(C)c7ccccc7N9c7ccccc7C8(C)C)ccc65)cc4)cc1c32] |

TABLE 3-continued
| No. | Structure |
|---|---|
| 46 | 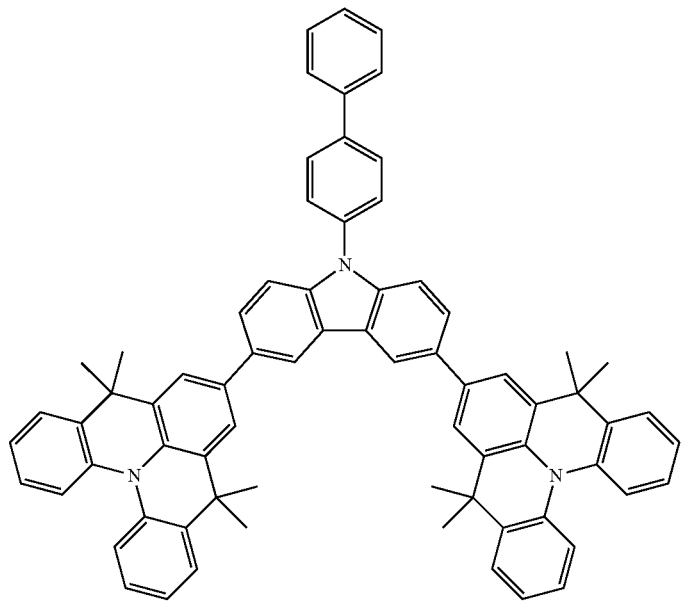 [SMILES: CC1(C)c2ccccc2N2c3ccccc3C(C)(C)c3cc(-c4ccc5c(c4)c4cc(-c6cc7c8c(c6)C(C)(C)c6ccccc6N8c6ccccc6C7(C)C)ccc4n5-c4ccc(-c5ccccc5)cc4)cc1c32] |
| 47 | 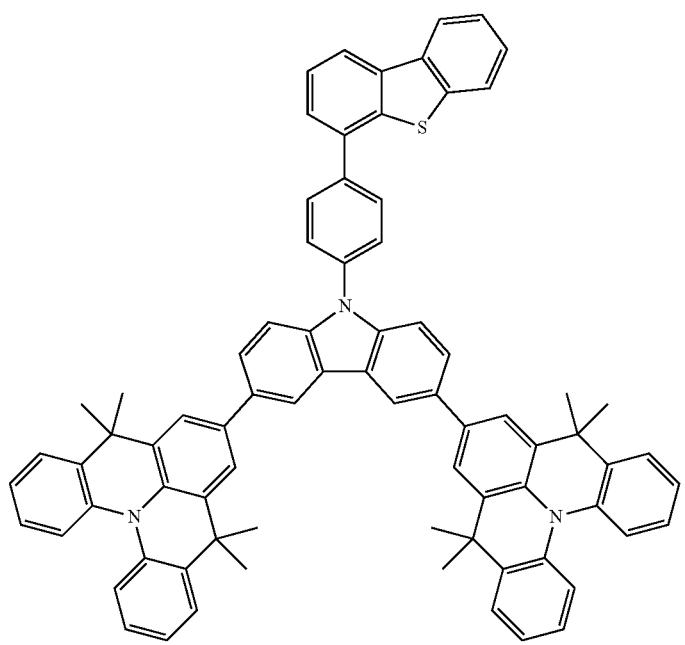 [SMILES: CC1(C)c2ccccc2N2c3ccccc3C(C)(C)c3cc(-c4ccc5c(c4)c4cc(-c6cc7c8c(c6)C(C)(C)c6ccccc6N8c6ccccc6C7(C)C)ccc4n5-c4ccc(-c5cccc6c5sc5ccccc56)cc4)cc1c32] |

TABLE 3-continued
| No. | Structure |
|---|---|
| 48 | 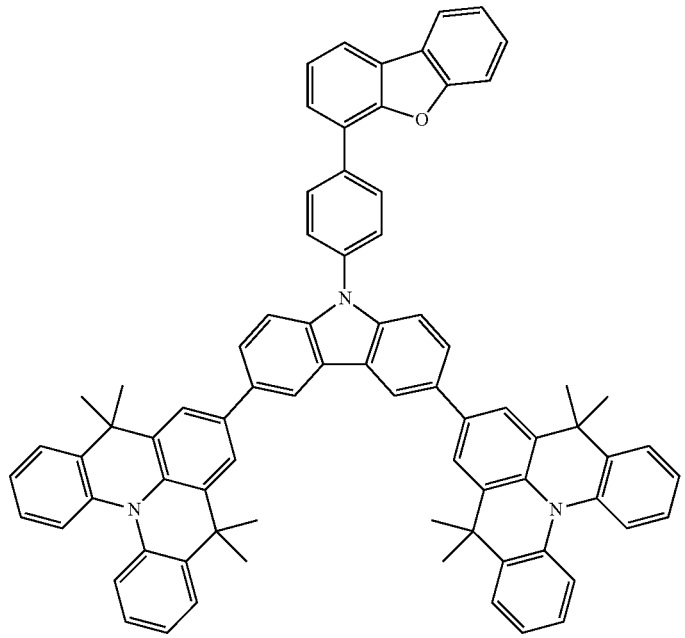 |
| 49 | 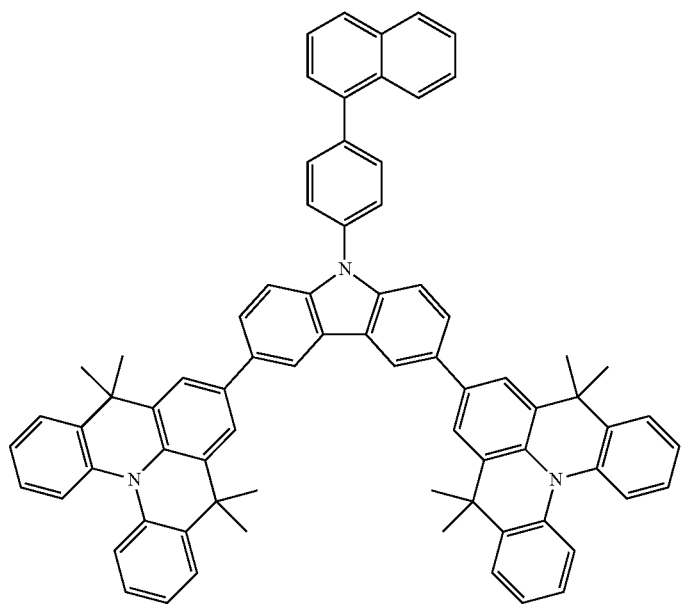 [SMILES: CC1(C)c2ccccc2N2c3ccccc3C(C)(C)c3cc(-c4ccc5c(c4)c4cc(-c6cc7c8c(c6)C(C)(C)c6ccccc6N8c6ccccc6C7(C)C)ccc4n5-c4ccc(-c5cccc6ccccc56)cc4)cc1c32] |

TABLE 3-continued
| No. | Structure |
|---|---|
| 50 | 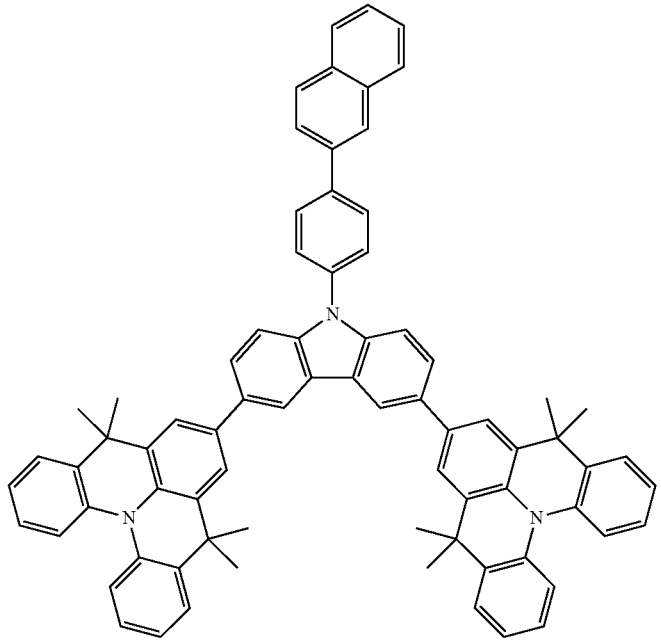 [SMILES: CC1(C)c2ccccc2N2c3ccccc3C(C)(C)c3cc(-c4ccc5c(c4)c4cc(-c6cc7c8c(c6)C(C)(C)c6ccccc6N8c6ccccc6C7(C)C)ccc4n5-c4ccc(-c5ccc6ccccc6c5)cc4)cc1c32] |
| 51 | 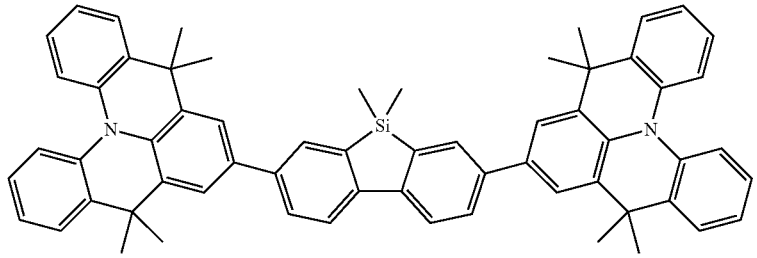 [SMILES: CC1(C)c2ccccc2N2c3ccccc3C(C)(C)c3cc(-c4ccc5c(c4)[Si](C)(C)c4cc(-c6cc7c8c(c6)C(C)(C)c6ccccc6N8c6ccccc6C7(C)C)ccc4-5)cc1c32] |
| 52 | 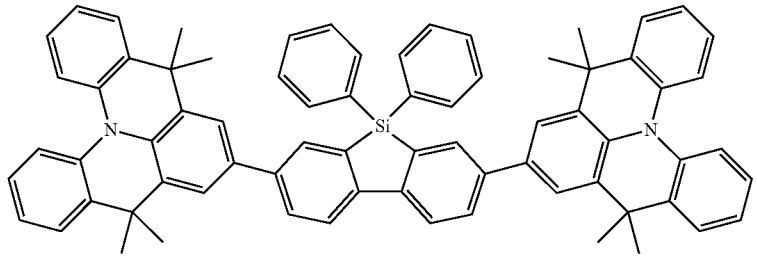 |
| 53 | 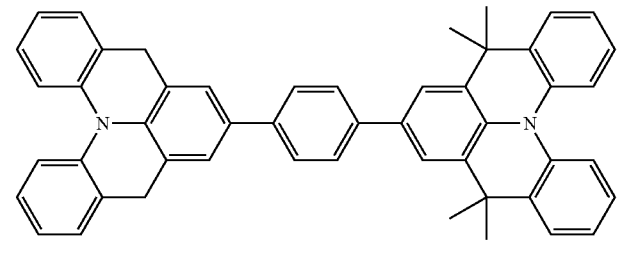 [SMILES: CC1(C)c2ccccc2N2c3ccccc3C(C)(C)c3cc(-c4ccc(-c5cc6c7c(c5)Cc5ccccc5N7c5ccccc5C6)cc4)cc1c32] |

TABLE 3-continued
| No. | Structure |
|---|---|
| 54 | 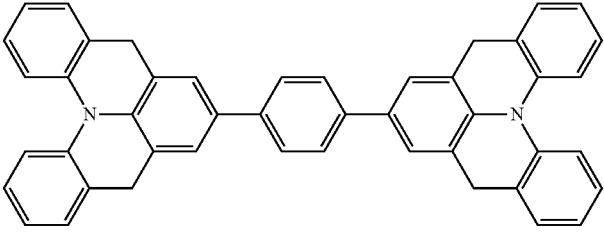 [SMILES: c1ccc2c(c1)Cc1cc(-c3ccc(-c4cc5c6c(c4)Cc4ccccc4N6c4ccccc4C5)cc3)cc3c1N2c1ccccc1C3] |
| 55 | 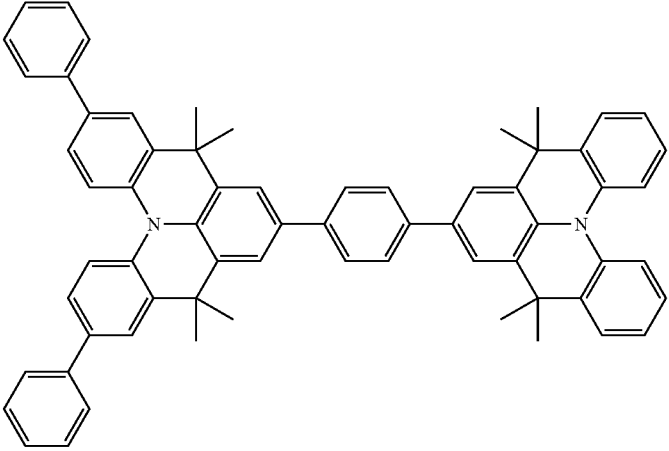 [SMILES: CC1(C)c2ccccc2N2c3ccccc3C(C)(C)c3cc(-c4ccc(-c5cc6c7c(c5)C(C)(C)c5cc(-c8ccccc8)ccc5N7c5ccc(-c7ccccc7)cc5C6(C)C)cc4)cc1c32] |
| 56 | 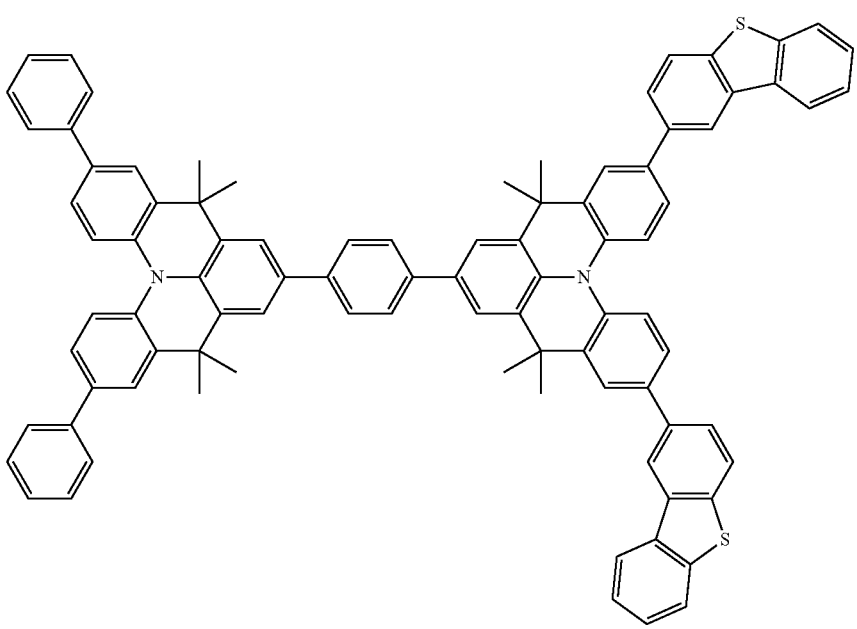 [SMILES: CC1(C)c2cc(-c3ccccc3)ccc2N2c3ccc(-c4ccccc4)cc3C(C)(C)c3cc(-c4ccc(-c5cc6c7c(c5)C(C)(C)c5cc(-c8ccc9oc%10ccccc%10c9c8)ccc5N7c5ccc(-c7ccc8oc9ccccc9c8c7)cc5C6(C)C)cc4)cc1c32] |

TABLE 3-continued
| No. | Structure |
|---|---|
| 57 | 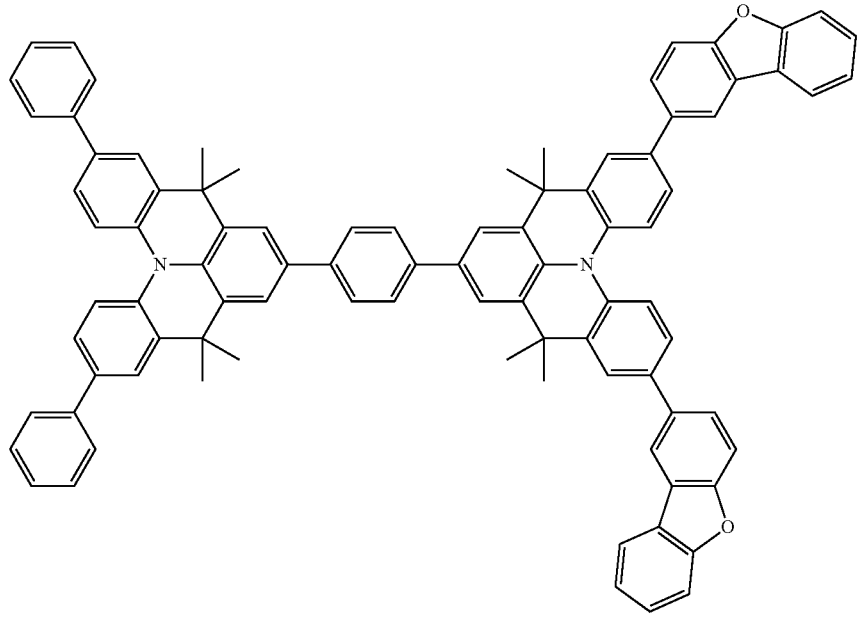 |
| 58 | 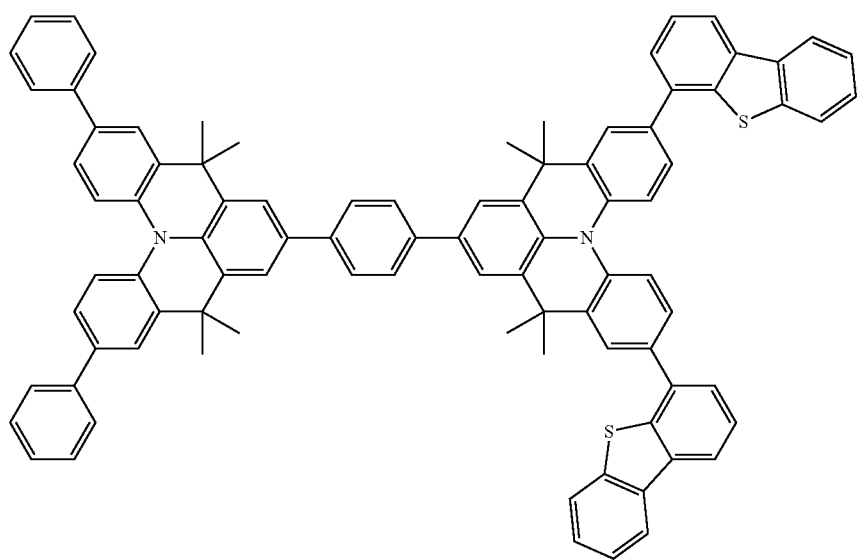 [SMILES: CC1(C)c2cc(-c3ccccc3)ccc2N2c3ccc(-c4ccccc4)cc3C(C)(C)c3cc(-c4ccc(-c5cc6c7c(c5)C(C)(C)c5cc(-c8cccc9c8oc8ccccc89)ccc5N7c5ccc(-c7cccc8c7oc7ccccc78)cc5C6(C)C)cc4)cc1c32] |

TABLE 3-continued
| No. | Structure |
|---|---|
| 59 | 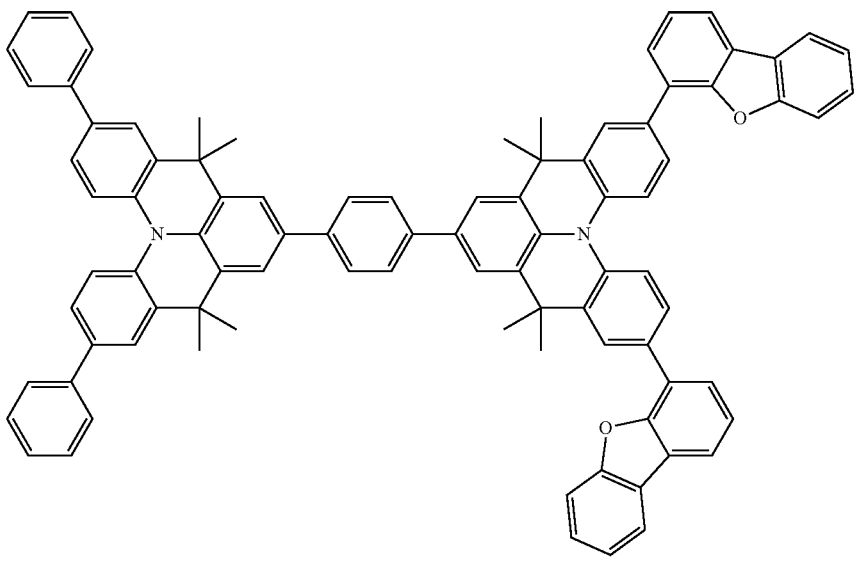 |
| 60 | 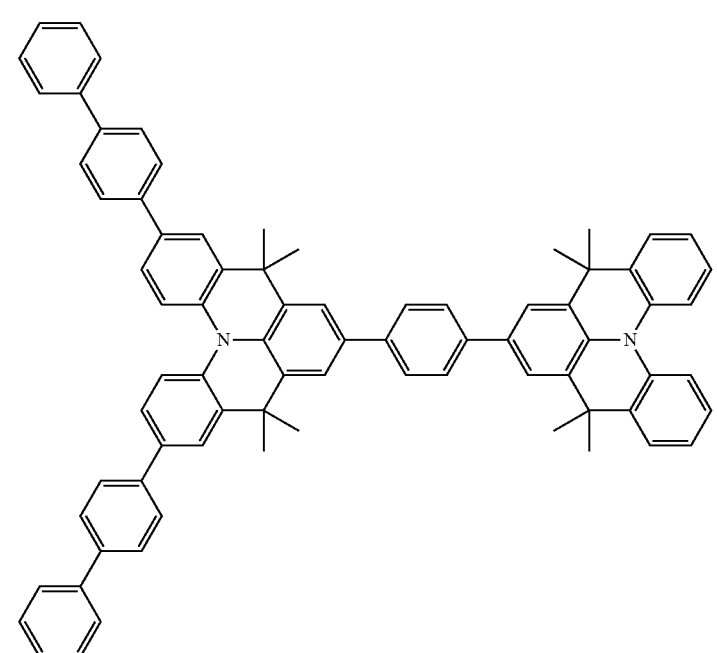 |

TABLE 3-continued
| No. | Structure |
|---|---|
| 61 | 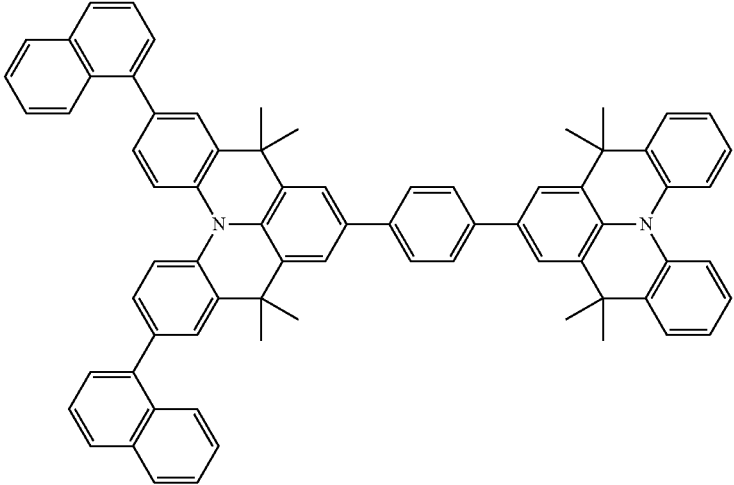 [SMILES: CC1(C)c2ccccc2N2c3ccccc3C(C)(C)c3cc(-c4ccc(-c5cc6c7c(c5)C(C)(C)c5cc(-c8cccc9ccccc89)ccc5N7c5ccc(-c7cccc8ccccc78)cc5C6(C)C)cc4)cc1c32] |
| 62 | 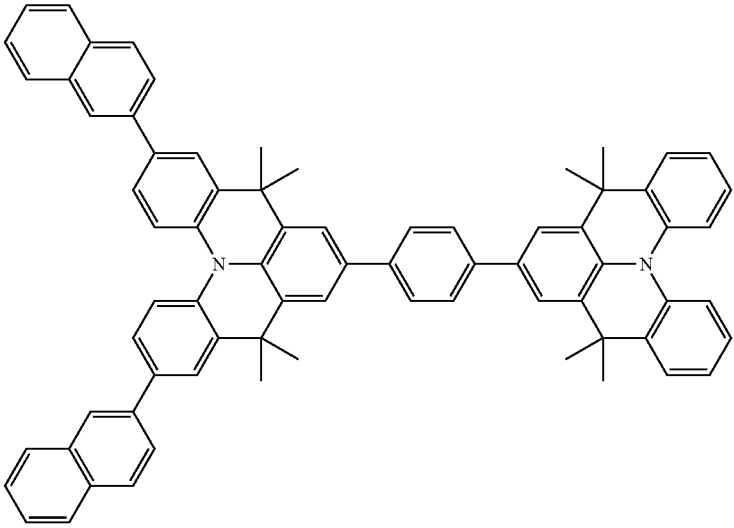 [SMILES: CC1(C)c2ccccc2N2c3ccccc3C(C)(C)c3cc(-c4ccc(-c5cc6c7c(c5)C(C)(C)c5cc(-c8ccc9ccccc9c8)ccc5N7c5ccc(-c7ccc8ccccc8c7)cc5C6(C)C)cc4)cc1c32] |
| 63 | 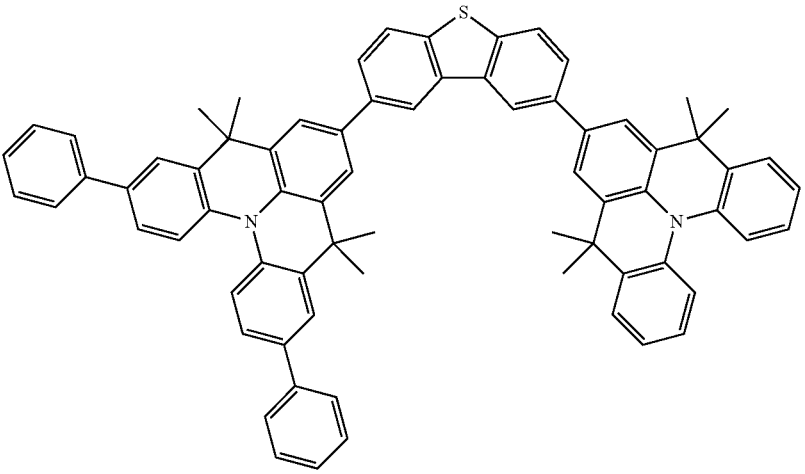 [SMILES: CC1(C)c2ccccc2N2c3ccccc3C(C)(C)c3cc(-c4ccc5sc6ccc(-c7cc8c9c(c7)C(C)(C)c7cc(-c%10ccccc%10)ccc7N9c7ccc(-c9ccccc9)cc7C8(C)C)cc6c5c4)cc1c32] |

TABLE 3-continued

| No. | Structure |
|---|---|
| 64 | 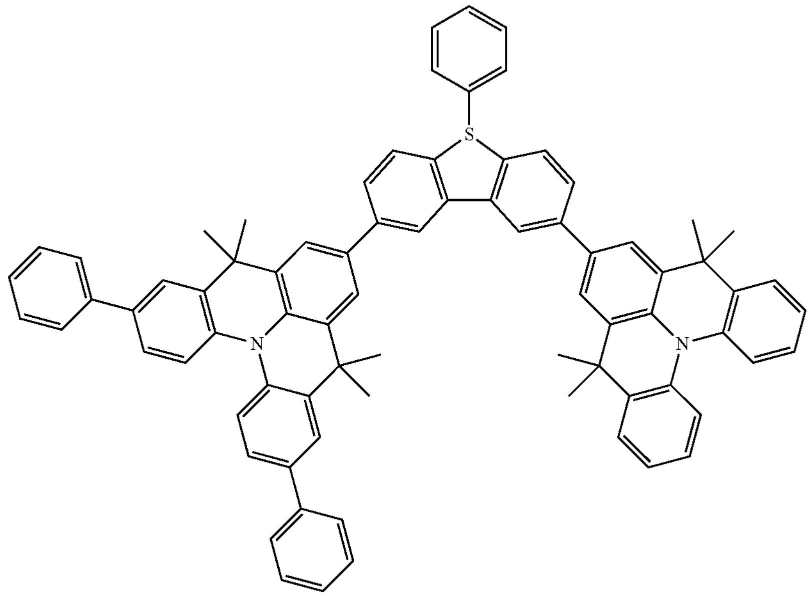 |
| 65 | 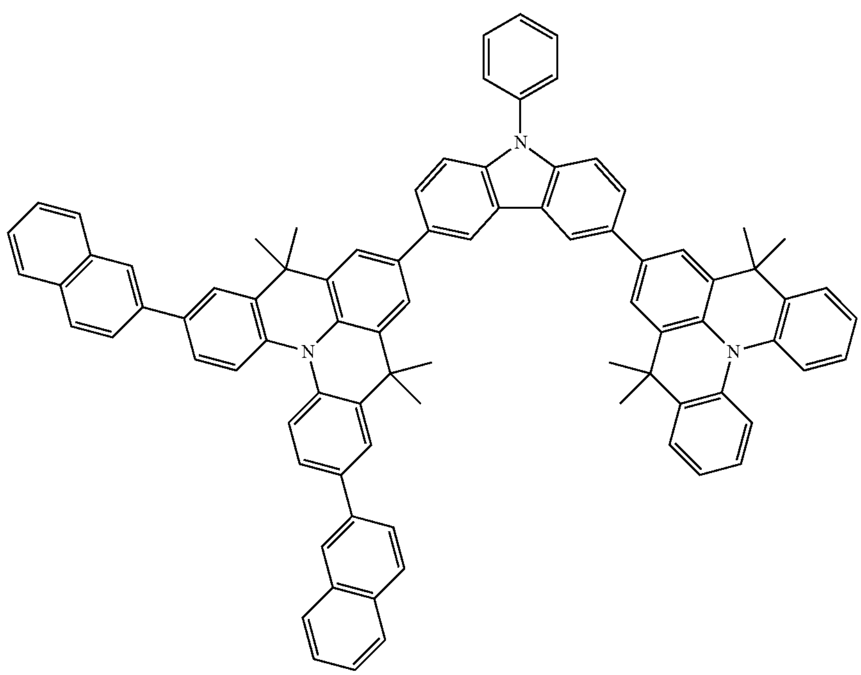 [SMILES: CC1(C)c2ccccc2N2c3ccccc3C(C)(C)c3cc(-c4ccc5c(c4)c4cc(-c6cc7c8c(c6)C(C)(C)c6cc(-c9ccc%10ccccc%10c9)ccc6N8c6ccc(-c8ccc9ccccc9c8)cc6C7(C)C)ccc4n5-c4ccccc4)cc1c32] |

TABLE 3-continued

| No. | Structure |
|---|---|
| 66 | 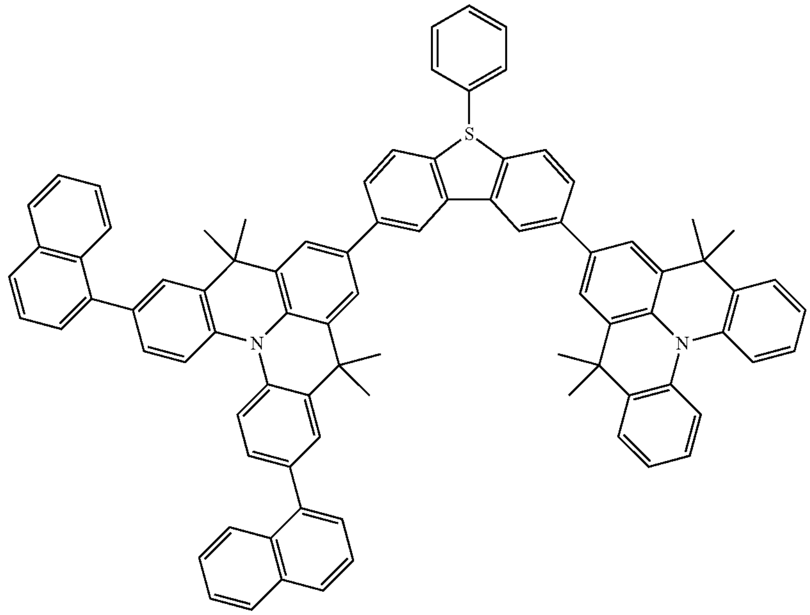 |
| 67 | 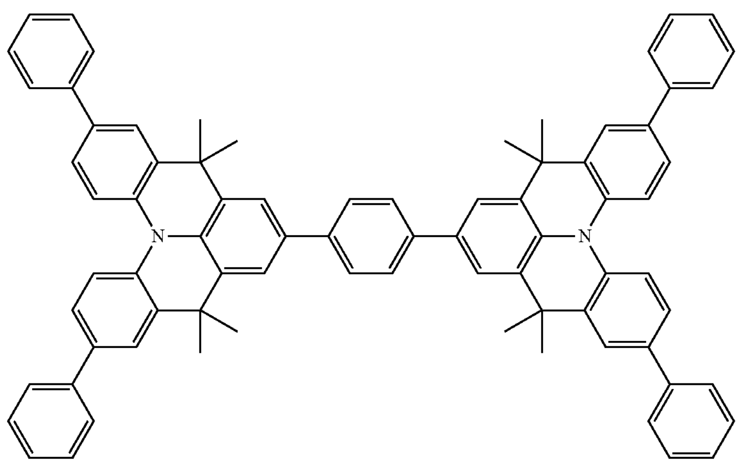 [SMILES: CC1(C)c2cc(-c3ccccc3)ccc2N2c3ccc(-c4ccccc4)cc3C(C)(C)c3cc(-c4ccc(-c5cc6c7c(c5)C(C)(C)c5cc(-c8ccccc8)ccc5N7c5ccc(-c7ccccc7)cc5C6(C)C)cc4)cc1c32] |
| 68 | 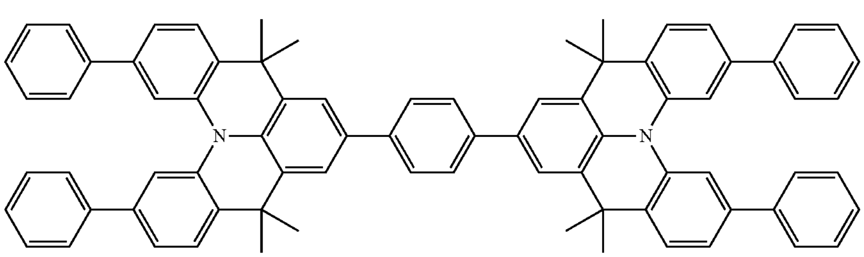 [SMILES: CC1(C)c2ccc(-c3ccccc3)cc2N2c3cc(-c4ccccc4)ccc3C(C)(C)c3cc(-c4ccc(-c5cc6c7c(c5)C(C)(C)c5ccc(-c8ccccc8)cc5N7c5cc(-c7ccccc7)ccc5C6(C)C)cc4)cc1c32] |

US 10,141,519 B2
TABLE 3-continued
| No. | Structure |
|---|---|
| 69 | 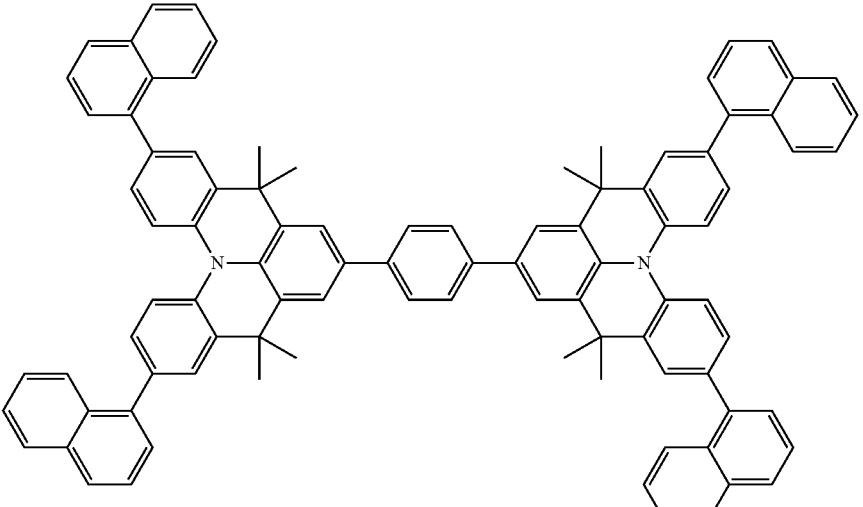 |
| 70 | 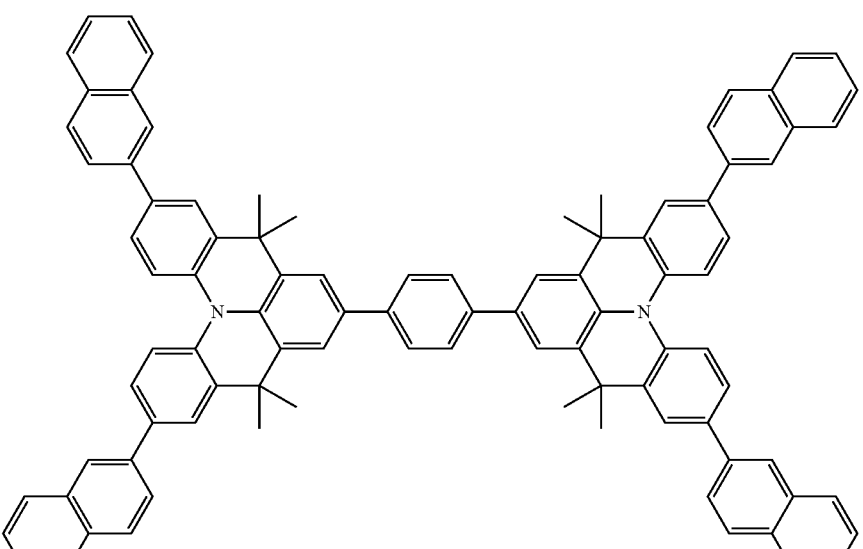 |
| 71 | 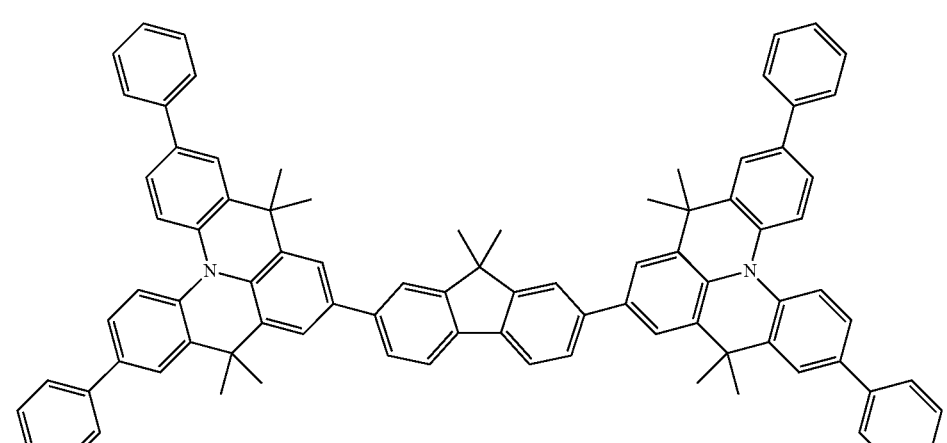 |

TABLE 3-continued

| No. | Structure |
|---|---|
| 72 | 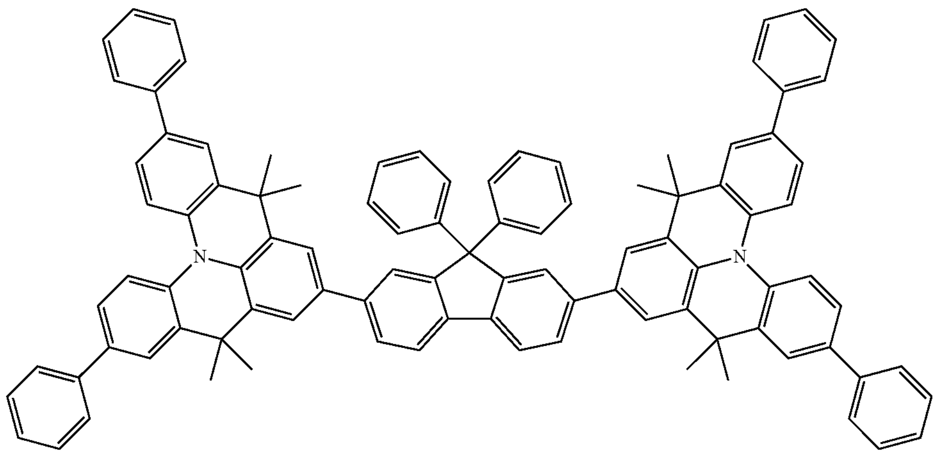 [SMILES: CC1(C)c2cc(-c3ccccc3)ccc2N2c3ccc(-c4ccccc4)cc3C(C)(C)c3cc(-c4ccc5c(c4)C(c4ccccc4)(c4ccccc4)c4cc(-c6cc7c8c(c6)C(C)(C)c6cc(-c9ccccc9)ccc6N8c6ccc(-c8ccccc8)cc6C7(C)C)ccc4-5)cc1c32] |
| 73 | 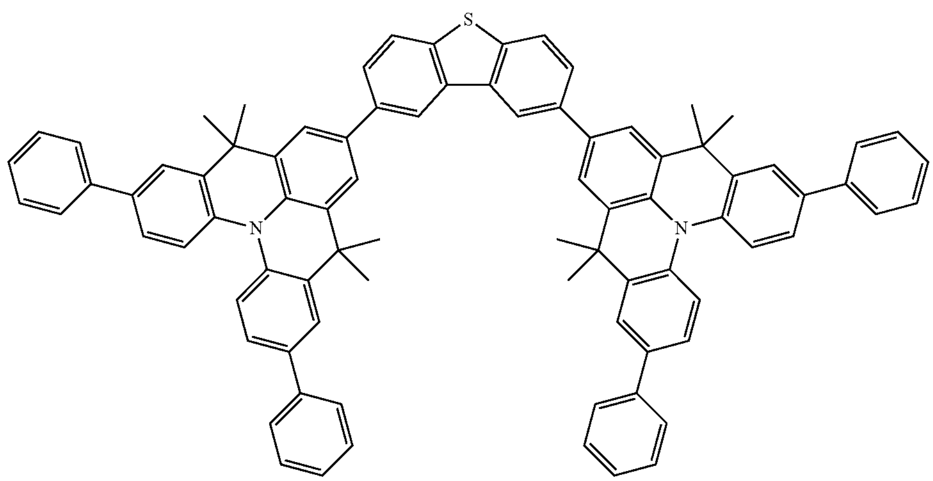 |
| 74 | 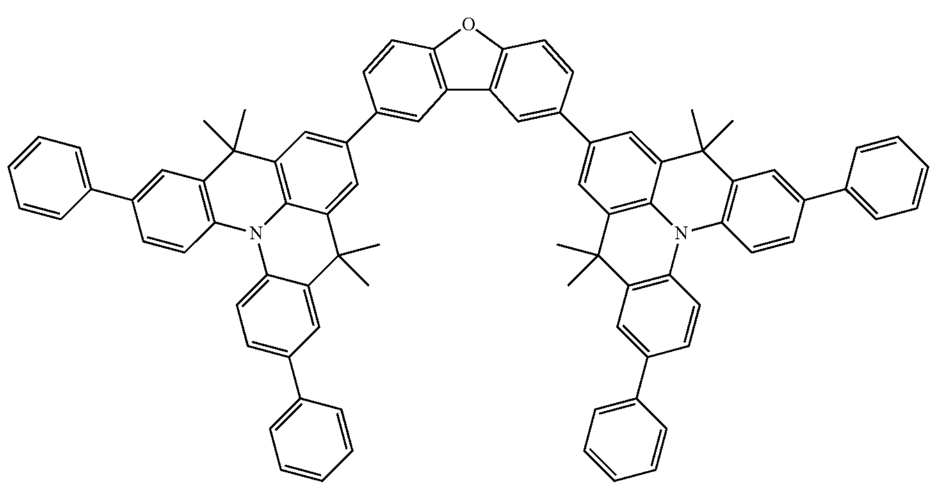 [SMILES: CC1(C)c2cc(-c3ccccc3)ccc2N2c3ccc(-c4ccccc4)cc3C(C)(C)c3cc(-c4ccc5sc6ccc(-c7cc8c9c(c7)C(C)(C)c7cc(-c%10ccccc%10)ccc7N9c7ccc(-c9ccccc9)cc7C8(C)C)cc6c5c4)cc1c32] |

TABLE 3-continued
| No. | Structure |
|---|---|
| 75 | 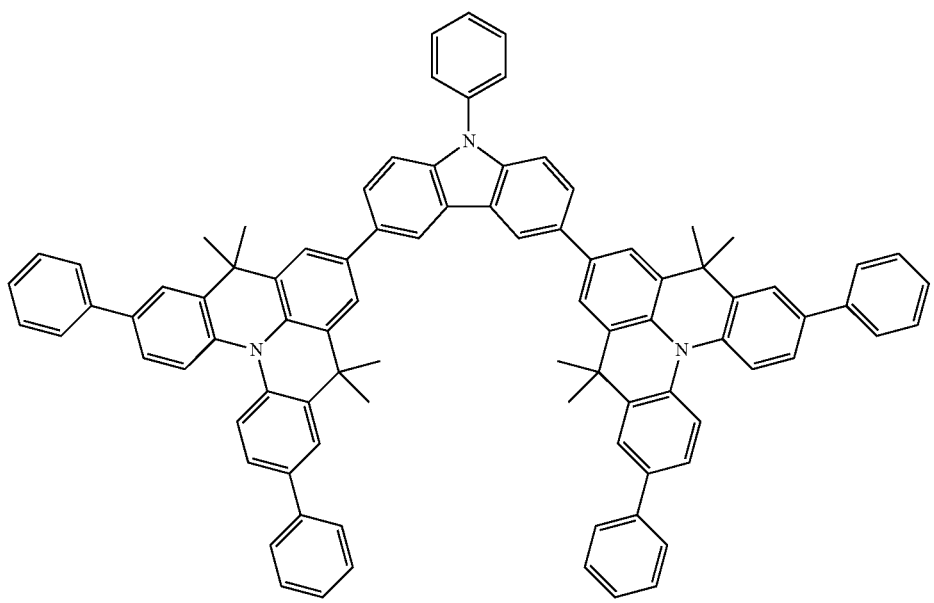 [SMILES: CC1(C)c2cc(-c3ccccc3)ccc2N2c3ccc(-c4ccccc4)cc3C(C)(C)c3cc(-c4ccc5c(c4)c4cc(-c6cc7c8c(c6)C(C)(C)c6cc(-c9ccccc9)ccc6N8c6ccc(-c8ccccc8)cc6C7(C)C)ccc4n5-c4ccccc4)cc1c32] |
| 76 | 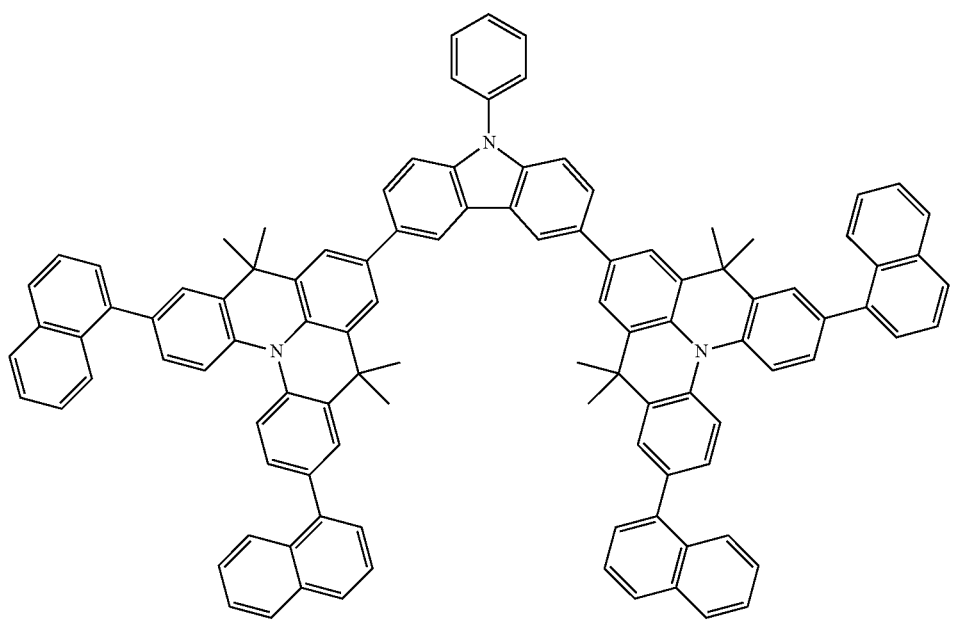 [SMILES: CC1(C)c2cc(-c3cccc4ccccc34)ccc2N2c3ccc(-c4cccc5ccccc45)cc3C(C)(C)c3cc(-c4ccc5c(c4)c4cc(-c6cc7c8c(c6)C(C)(C)c6cc(-c9cccc%10ccccc9%10)ccc6N8c6ccc(-c8cccc9ccccc89)cc6C7(C)C)ccc4n5-c4ccccc4)cc1c32] |

TABLE 3-continued
| No. | Structure |
|---|---|
| 77 | 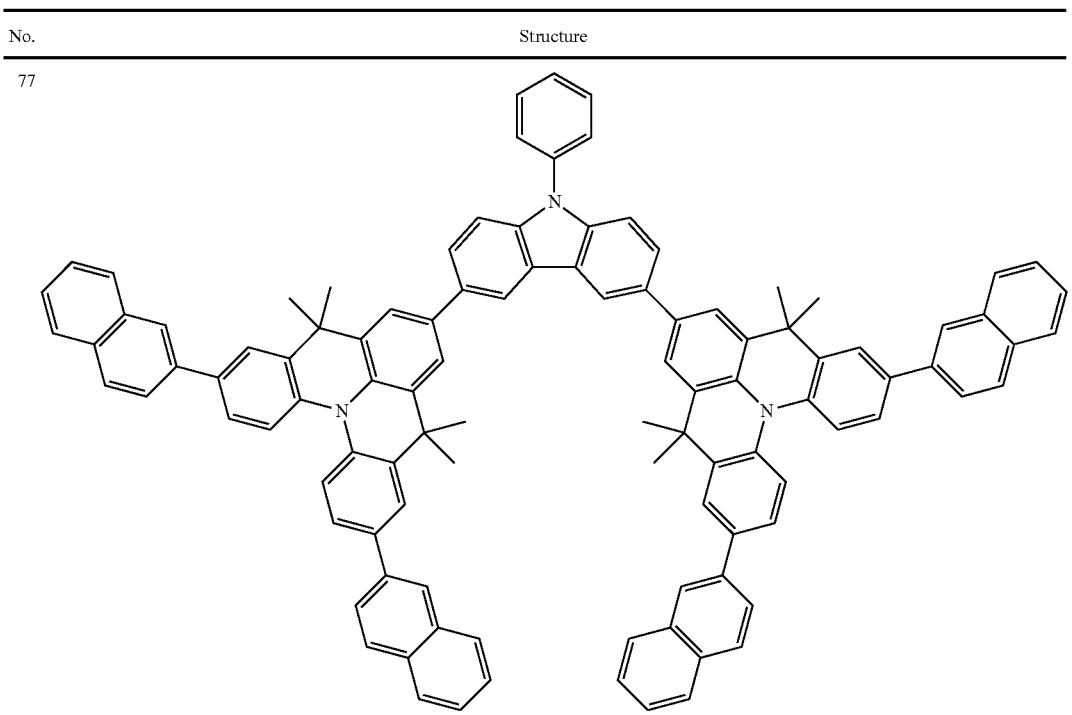 |
| 78 | 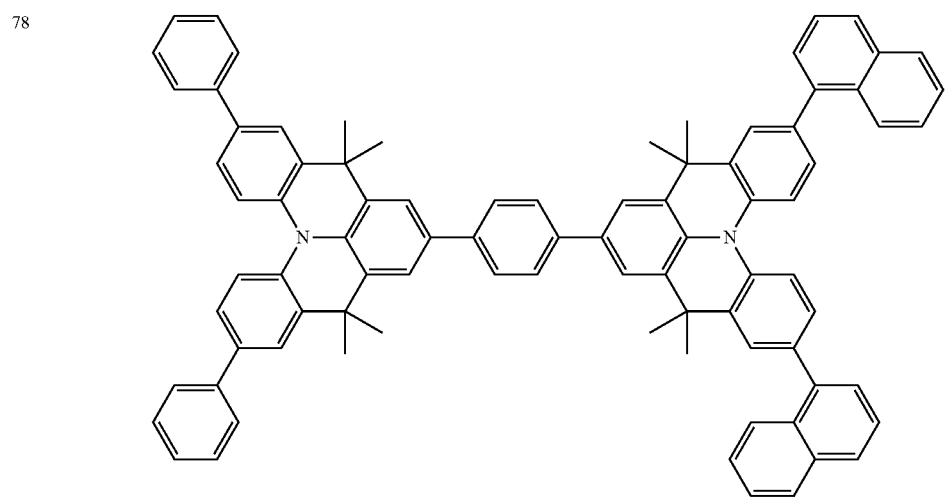 |

TABLE 3-continued

| No. | Structure |
|---|---|
| 79 | 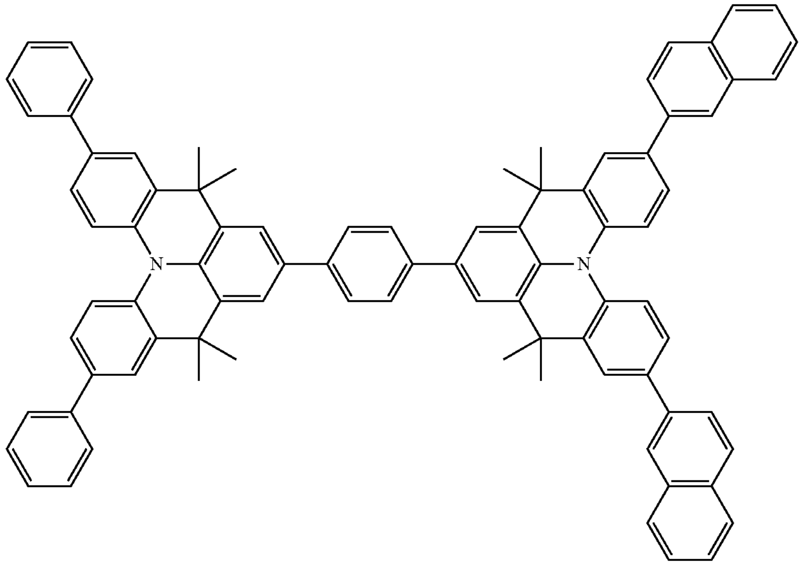 [SMILES: CC1(C)c2cc(-c3ccccc3)ccc2N2c3ccc(-c4ccccc4)cc3C(C)(C)c3cc(-c4ccc(-c5cc6c7c(c5)C(C)(C)c5cc(-c8ccc9ccccc9c8)ccc5N7c5ccc(-c7ccc8ccccc8c7)cc5C6(C)C)cc4)cc1c32] |
| 80 | 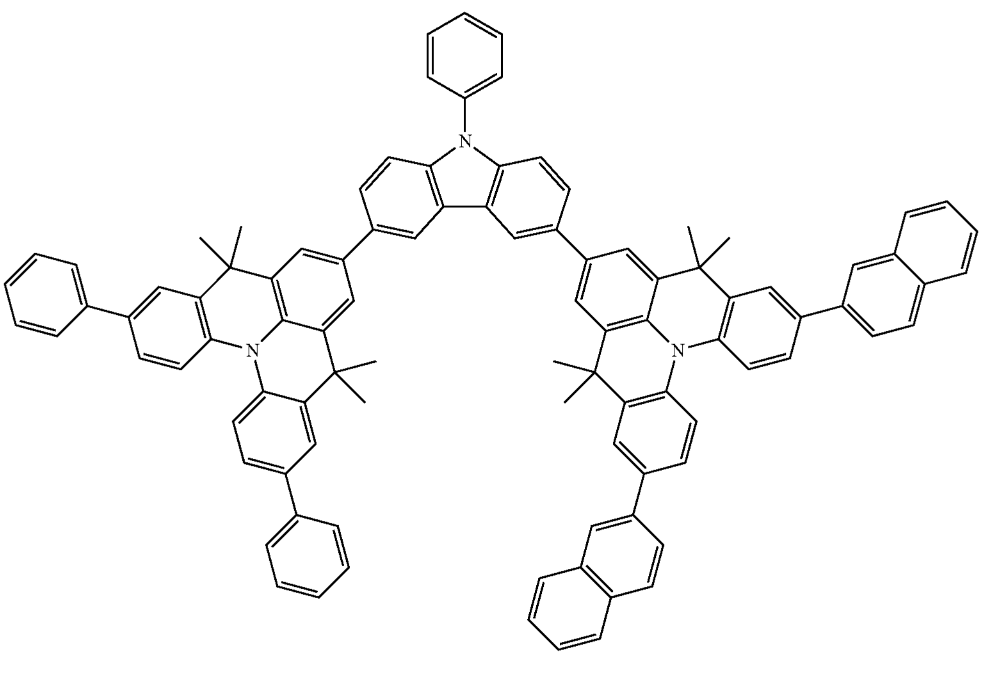 [SMILES: CC1(C)c2cc(-c3ccccc3)ccc2N2c3ccc(-c4ccccc4)cc3C(C)(C)c3cc(-c4ccc5c(c4)c4cc(-c6cc7c8c(c6)C(C)(C)c6cc(-c9ccc%10ccccc%10c9)ccc6N8c6ccc(-c8ccc9ccccc9c8)cc6C7(C)C)ccc4n5-c4ccccc4)cc1c32] |

TABLE 3-continued

| No. | Structure |
|---|---|
| 81 | 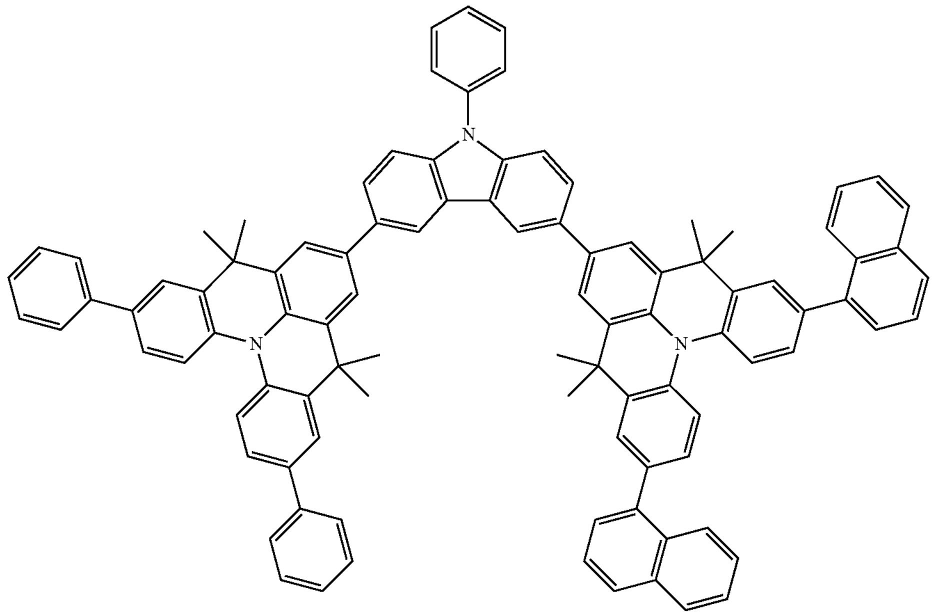 [SMILES: CC1(C)c2cc(-c3ccccc3)ccc2N2c3ccc(-c4ccccc4)cc3C(C)(C)c3cc(-c4ccc5c(c4)c4cc(-c6cc7c8c(c6)C(C)(C)c6cc(-c9cccc%10ccccc9%10)ccc6N8c6ccc(-c8cccc9ccccc89)cc6C7(C)C)ccc4n5-c4ccccc4)cc1c32] |
| 82 | 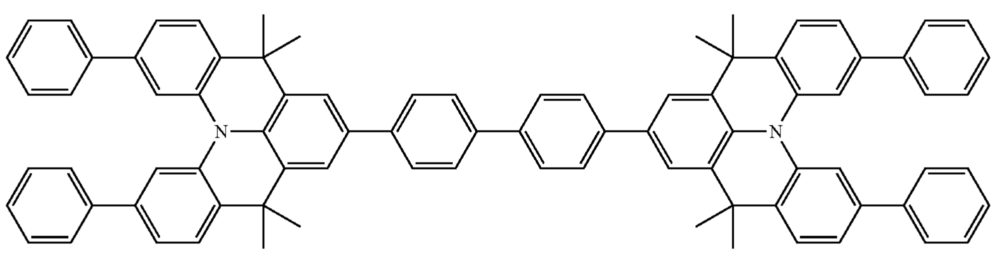 [SMILES: CC1(C)c2ccc(-c3ccccc3)cc2N2c3cc(-c4ccccc4)ccc3C(C)(C)c3cc(-c4ccc(-c5ccc(-c6cc7c8c(c6)C(C)(C)c6ccc(-c9ccccc9)cc6N8c6cc(-c8ccccc8)ccc6C7(C)C)cc5)cc4)cc1c32] |
| 83 | 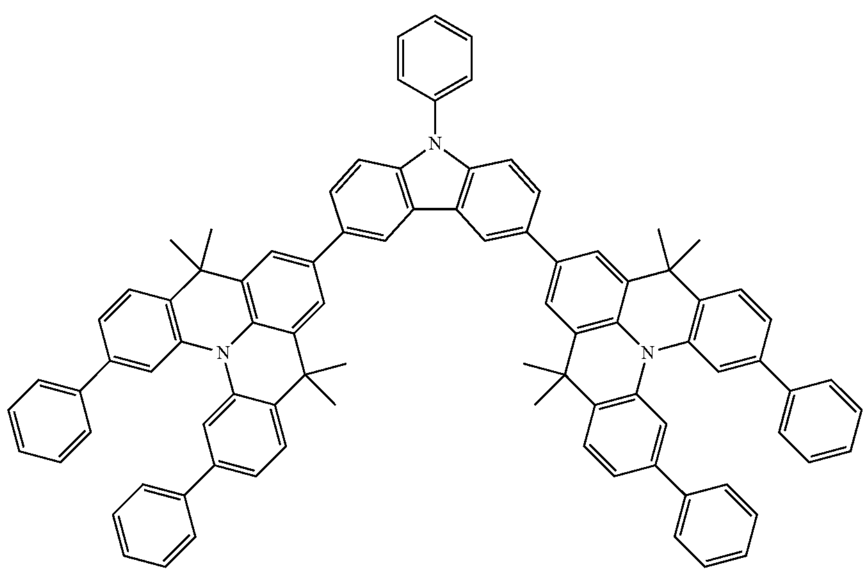 [SMILES: CC1(C)c2ccc(-c3ccccc3)cc2N2c3cc(-c4ccccc4)ccc3C(C)(C)c3cc(-c4ccc5c(c4)c4cc(-c6cc7c8c(c6)C(C)(C)c6ccc(-c9ccccc9)cc6N8c6cc(-c8ccccc8)ccc6C7(C)C)ccc4n5-c4ccccc4)cc1c32] |

TABLE 3-continued
| No. | Structure |
|---|---|
| 84 | 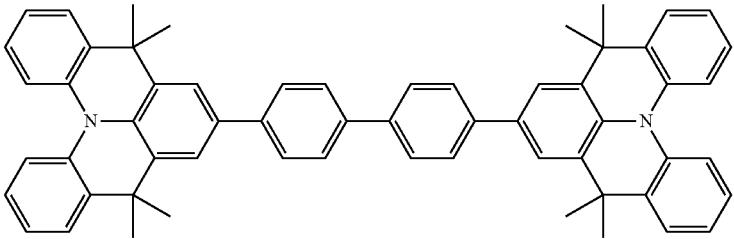 [SMILES: CC1(C)c2ccccc2N2c3ccccc3C(C)(C)c3cc(-c4ccc(-c5ccc(-c6cc7c8c(c6)C(C)(C)c6ccccc6N8c6ccccc6C7(C)C)cc5)cc4)cc1c32] |
| 85 | 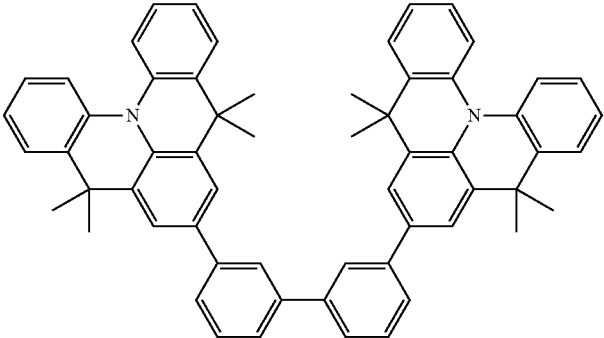 [SMILES: CC1(C)c2ccccc2N2c3ccccc3C(C)(C)c3cc(-c4cccc(-c5cccc(-c6cc7c8c(c6)C(C)(C)c6ccccc6N8c6ccccc6C7(C)C)c5)c4)cc1c32] |
| 86 | 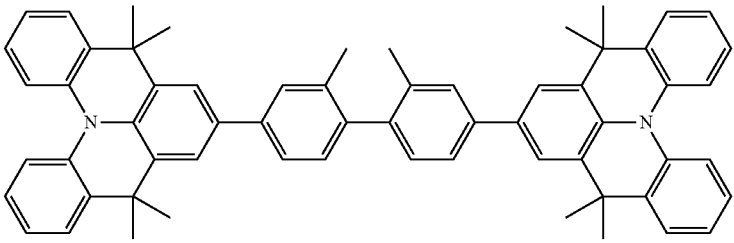 [SMILES: Cc1cc(-c2cc3c4c(c2)C(C)(C)c2ccccc2N4c2ccccc2C3(C)C)ccc1-c1ccc(-c2cc3c4c(c2)C(C)(C)c2ccccc2N4c2ccccc2C3(C)C)cc1C] |
| 87 | 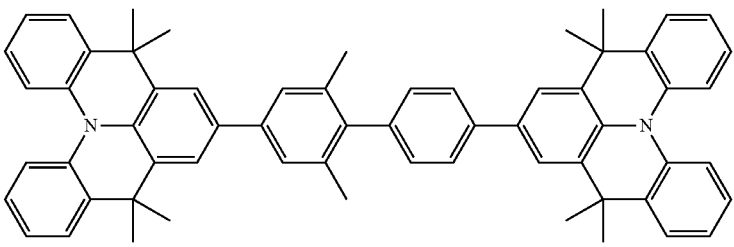 [SMILES: Cc1cc(-c2cc3c4c(c2)C(C)(C)c2ccccc2N4c2ccccc2C3(C)C)cc(C)c1-c1ccc(-c2cc3c4c(c2)C(C)(C)c2ccccc2N4c2ccccc2C3(C)C)cc1] |
| 88 | 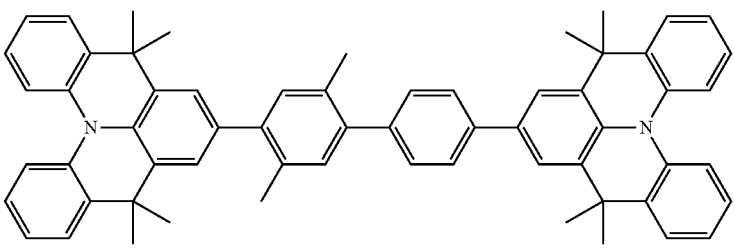 |

TABLE 3-continued

| No. | Structure |
|---|---|
| 89 | 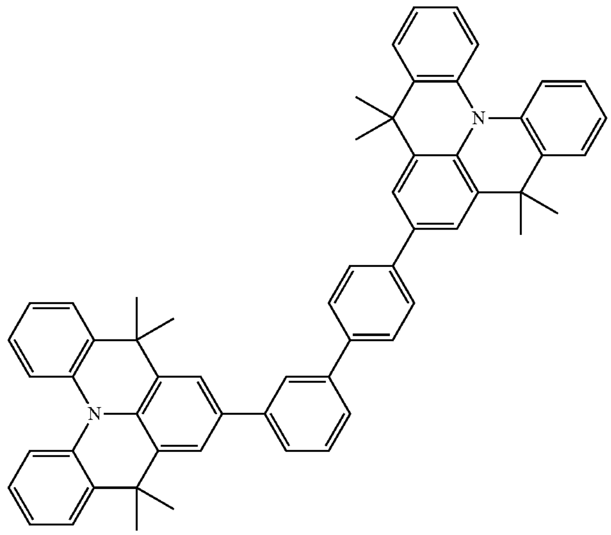 [SMILES: CC1(C)c2ccccc2N2c3ccccc3C(C)(C)c3cc(-c4ccc(-c5cccc(-c6cc7c8c(c6)C(C)(C)c6ccccc6N8c6ccccc6C7(C)C)c5)cc4)cc1c32] |
| 90 | 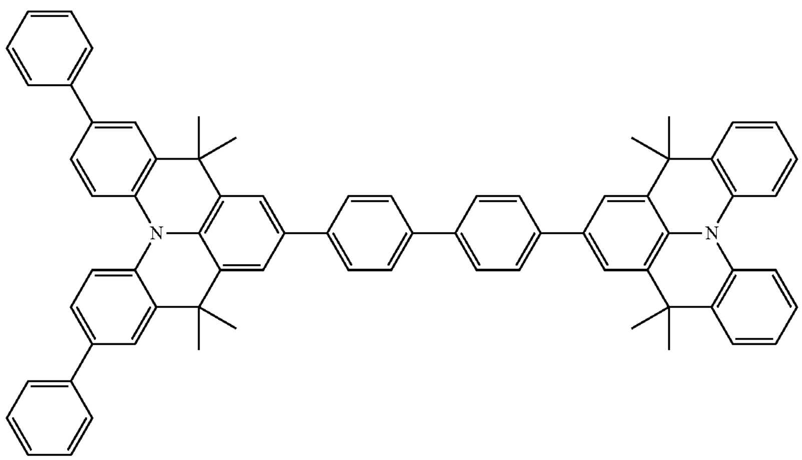 [SMILES: CC1(C)c2ccccc2N2c3ccccc3C(C)(C)c3cc(-c4ccc(-c5ccc(-c6cc7c8c(c6)C(C)(C)c6cc(-c9ccccc9)ccc6N8c6ccc(-c8ccccc8)cc6C7(C)C)cc5)cc4)cc1c32] |
| 91 | 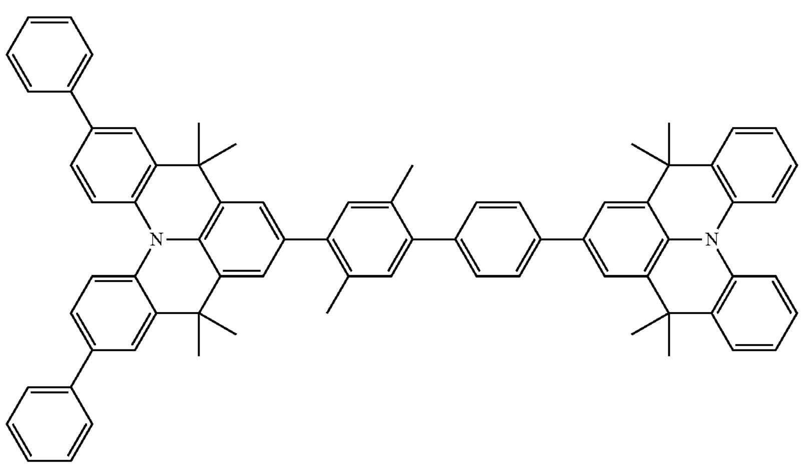 |

TABLE 3-continued
| No. | Structure |
|---|---|
| 92 | 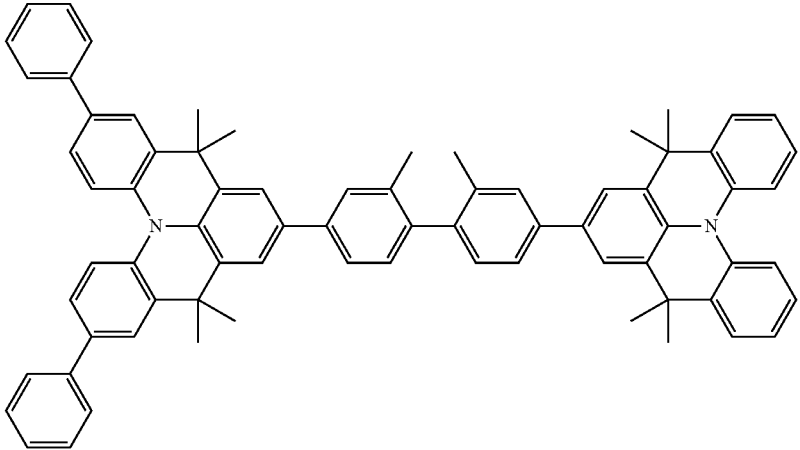 [SMILES: Cc1cc(-c2cc3c4c(c2)C(C)(C)c2ccccc2N4c2ccccc2C3(C)C)ccc1-c1ccc(-c2cc3c4c(c2)C(C)(C)c2cc(-c5ccccc5)ccc2N4c2ccc(-c4ccccc4)cc2C3(C)C)cc1C] |
| 93 | 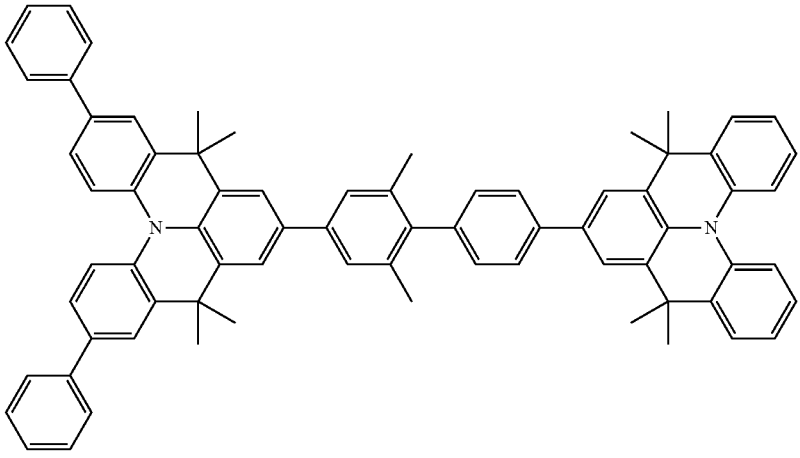 [SMILES: Cc1cc(-c2cc3c4c(c2)C(C)(C)c2cc(-c5ccccc5)ccc2N4c2ccc(-c4ccccc4)cc2C3(C)C)cc(C)c1-c1ccc(-c2cc3c4c(c2)C(C)(C)c2ccccc2N4c2ccccc2C3(C)C)cc1] |
| 94 | 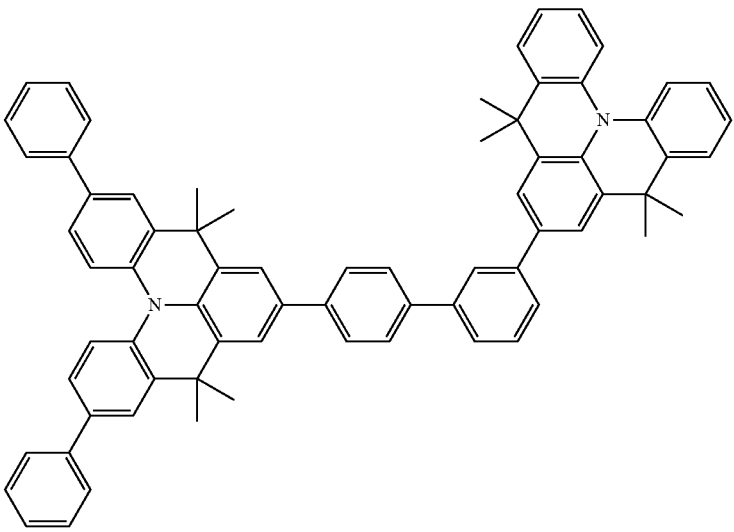 [SMILES: CC1(C)c2ccccc2N2c3ccccc3C(C)(C)c3cc(-c4cccc(-c5ccc(-c6cc7c8c(c6)C(C)(C)c6cc(-c9ccccc9)ccc6N8c6ccc(-c8ccccc8)cc6C7(C)C)cc5)c4)cc1c32] |

TABLE 3-continued

| No. | Structure |
|---|---|
| 95 | 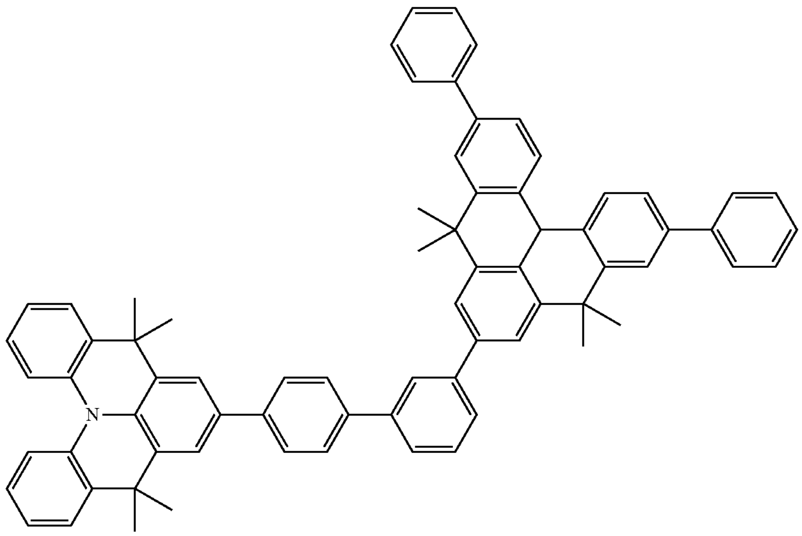 [SMILES: CC1(C)c2cc(-c3ccccc3)ccc2C2c3ccc(-c4ccccc4)cc3C(C)(C)c3cc(-c4cccc(-c5ccc(-c6cc7c8c(c6)C(C)(C)c6ccccc6N8c6ccccc6C7(C)C)cc5)c4)cc1c32] |
| 96 | 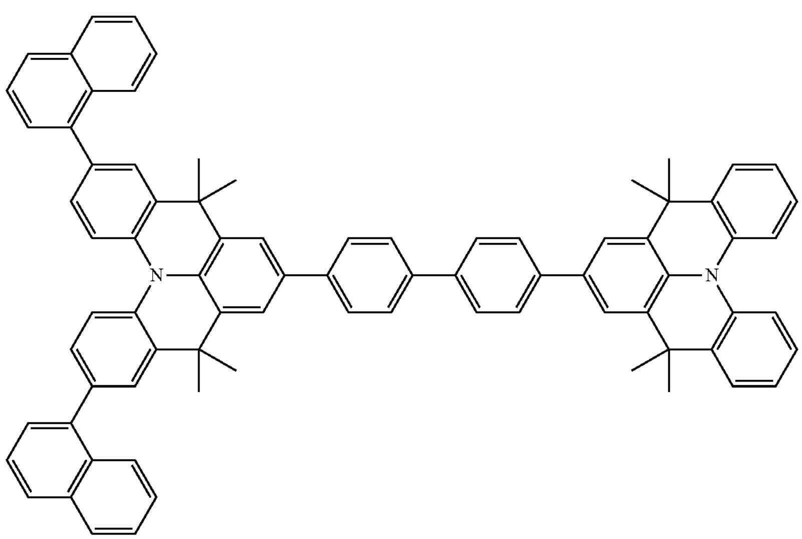 [SMILES: CC1(C)c2ccccc2N2c3ccccc3C(C)(C)c3cc(-c4ccc(-c5ccc(-c6cc7c8c(c6)C(C)(C)c6cc(-c9cccc%10ccccc9%10)ccc6N8c6ccc(-c8cccc9ccccc89)cc6C7(C)C)cc5)cc4)cc1c32] |

TABLE 3-continued

| No. | Structure |
|-----|-----------|
| 97  | 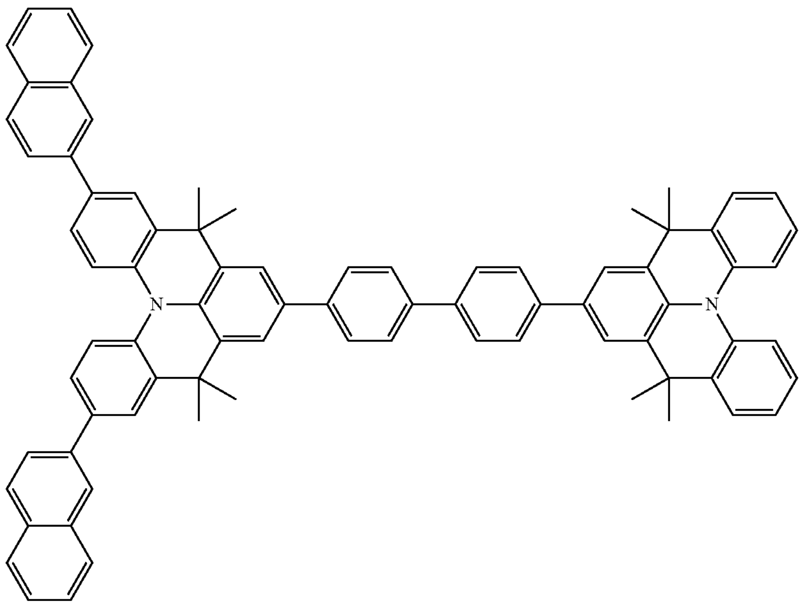 [SMILES: CC1(C)c2ccccc2N2c3ccccc3C(C)(C)c3cc(-c4ccc(-c5ccc(-c6cc7c8c(c6)C(C)(C)c6cc(-c9ccc%10ccccc%10c9)ccc6N8c6ccc(-c8ccc9ccccc9c8)cc6C7(C)C)cc5)cc4)cc1c32]          |
| 98  | 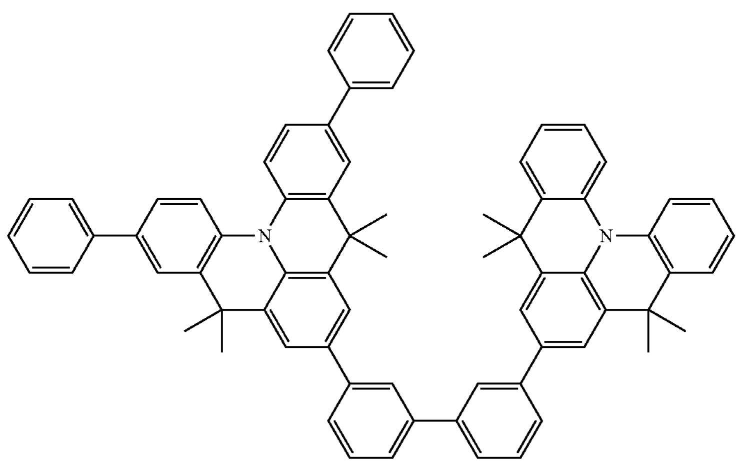 [SMILES: CC1(C)c2ccccc2N2c3ccccc3C(C)(C)c3cc(-c4cccc(-c5cccc(-c6cc7c8c(c6)C(C)(C)c6cc(-c9ccccc9)ccc6N8c6ccc(-c8ccccc8)cc6C7(C)C)c5)c4)cc1c32]          |
| 99  | 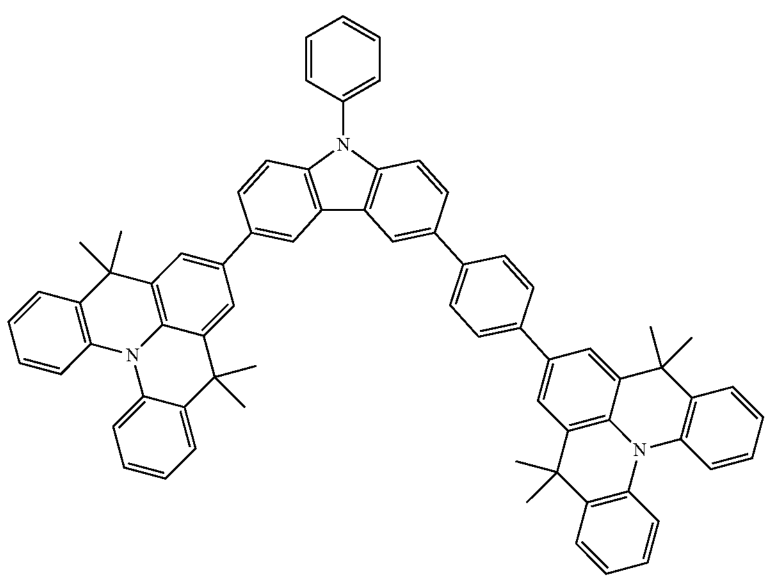 [SMILES: CC1(C)c2ccccc2N2c3ccccc3C(C)(C)c3cc(-c4ccc(-c5ccc6c(c5)c5cc(-c7cc8c9c(c7)C(C)(C)c7ccccc7N9c7ccccc7C8(C)C)ccc5n6-c5ccccc5)cc4)cc1c32]          |

TABLE 3-continued

| No. | Structure |
| --- | --- |
| 100 | 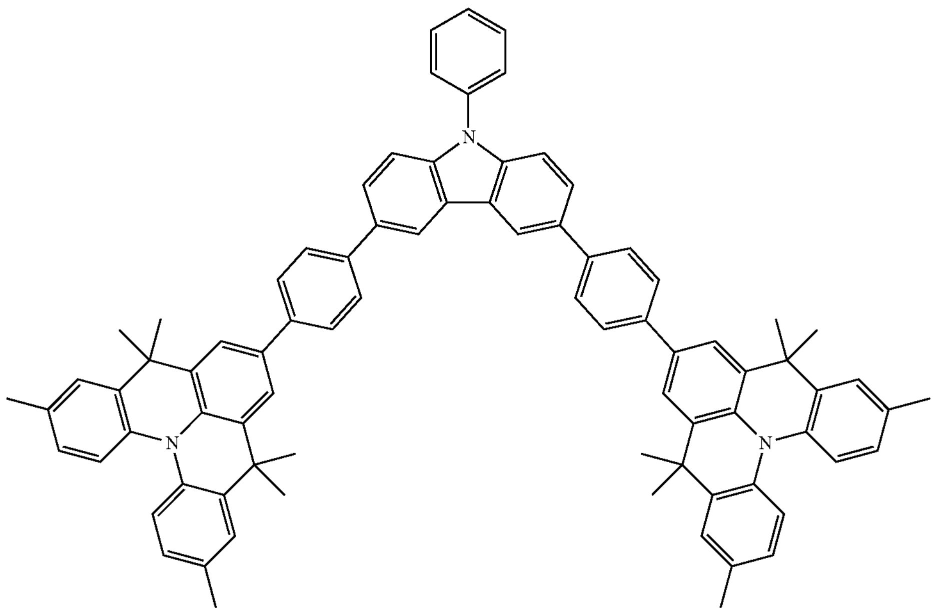 |
| 101 | 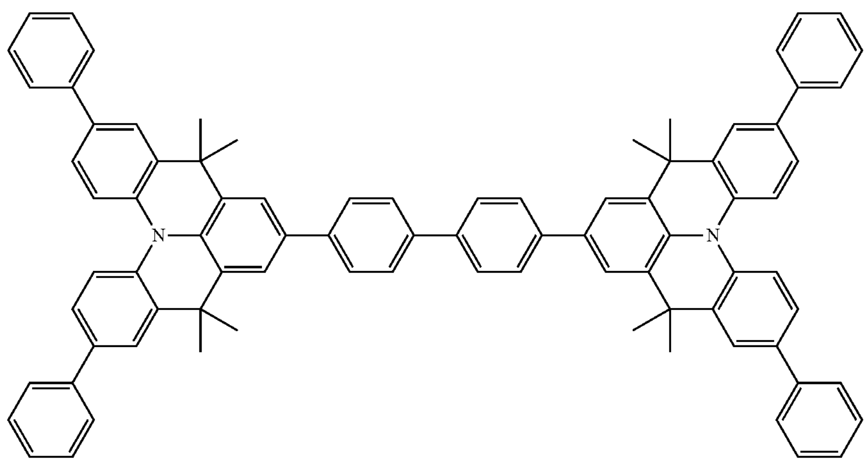 [SMILES: CC1(C)c2cc(-c3ccccc3)ccc2N2c3ccc(-c4ccccc4)cc3C(C)(C)c3cc(-c4ccc(-c5ccc(-c6cc7c8c(c6)C(C)(C)c6cc(-c9ccccc9)ccc6N8c6ccc(-c8ccccc8)cc6C7(C)C)cc5)cc4)cc1c32] |
| 102 | 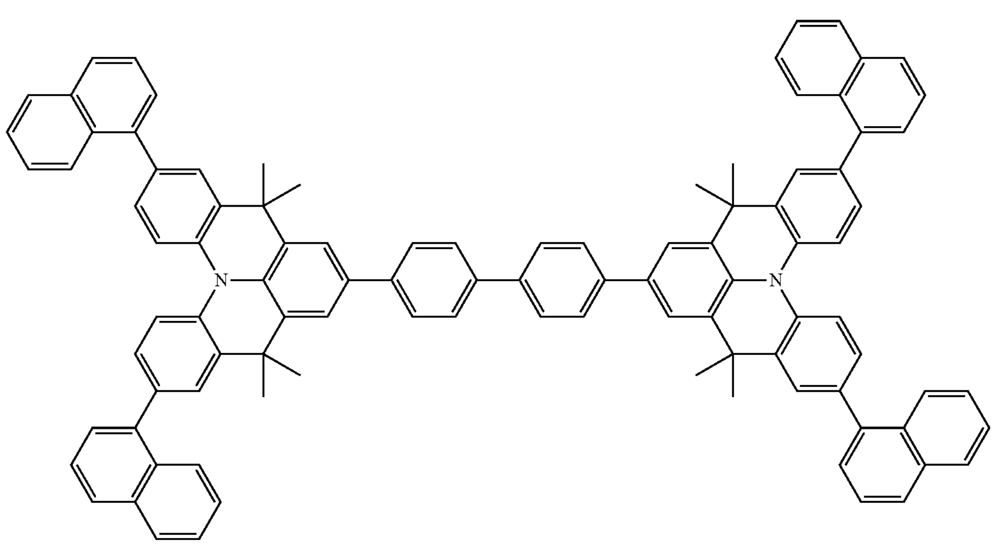 [SMILES: CC1(C)c2cc(-c3cccc4ccccc34)ccc2N2c3ccc(-c4cccc5ccccc45)cc3C(C)(C)c3cc(-c4ccc(-c5ccc(-c6cc7c8c(c6)C(C)(C)c6cc(-c9cccc%10ccccc9%10)ccc6N8c6ccc(-c8cccc9ccccc89)cc6C7(C)C)cc5)cc4)cc1c32] |

TABLE 3-continued
| No. | Structure |
|---|---|
| 103 | 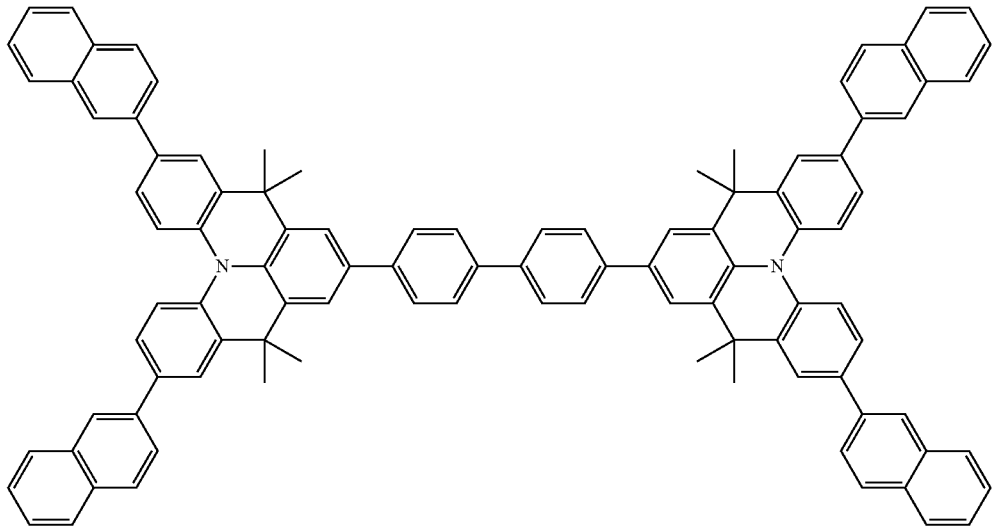 [SMILES: CC1(C)c2cc(-c3ccc4ccccc4c3)ccc2N2c3ccc(-c4ccc5ccccc5c4)cc3C(C)(C)c3cc(-c4ccc(-c5ccc(-c6cc7c8c(c6)C(C)(C)c6cc(-c9ccc%10ccccc%10c9)ccc6N8c6ccc(-c8ccc9ccccc9c8)cc6C7(C)C)cc5)cc4)cc1c32] |
| 104 | 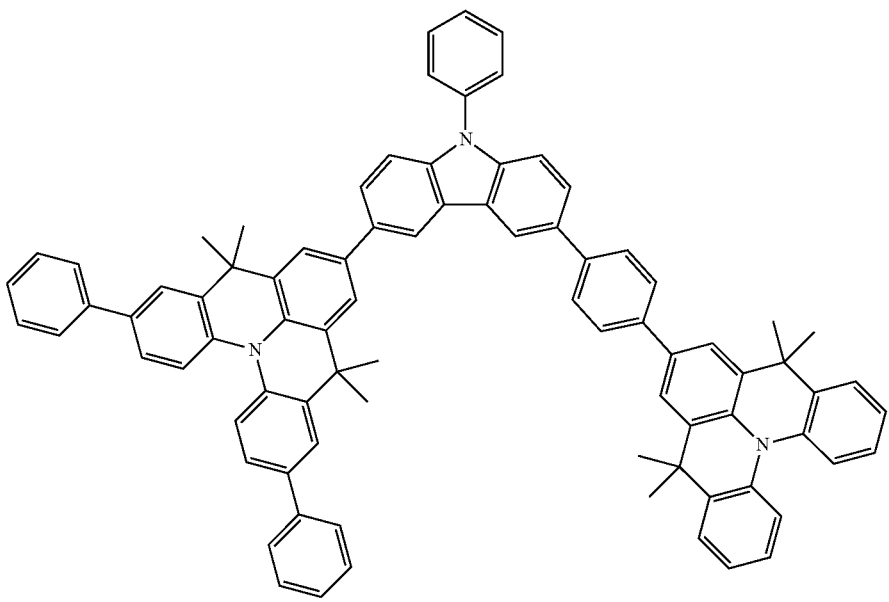 [SMILES: CC1(C)c2ccccc2N2c3ccccc3C(C)(C)c3cc(-c4ccc(-c5ccc6c(c5)c5cc(-c7cc8c9c(c7)C(C)(C)c7cc(-c%10ccccc%10)ccc7N9c7ccc(-c9ccccc9)cc7C8(C)C)ccc5n6-c5ccccc5)cc4)cc1c32] |

TABLE 3-continued

| No. | Structure |
|-----|-----------|
| 105 | 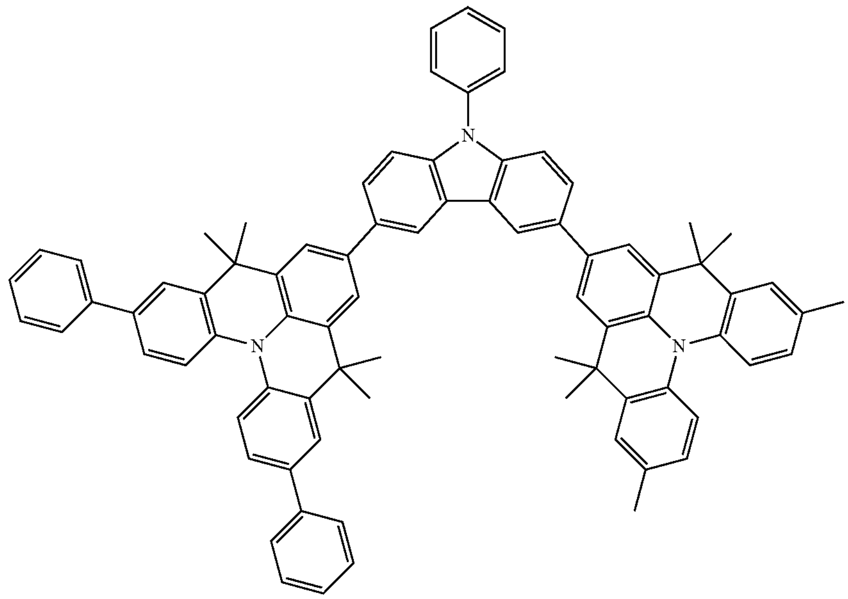 [SMILES: Cc1ccc2c(c1)C(C)(C)c1cc(-c3ccc4c(c3)c3cc(-c5cc6c7c(c5)C(C)(C)c5cc(-c8ccccc8)ccc5N7c5ccc(-c7ccccc7)cc5C6(C)C)ccc3n4-c3ccccc3)cc3c1N2c1ccc(C)cc1C3(C)C] |
| 106 | 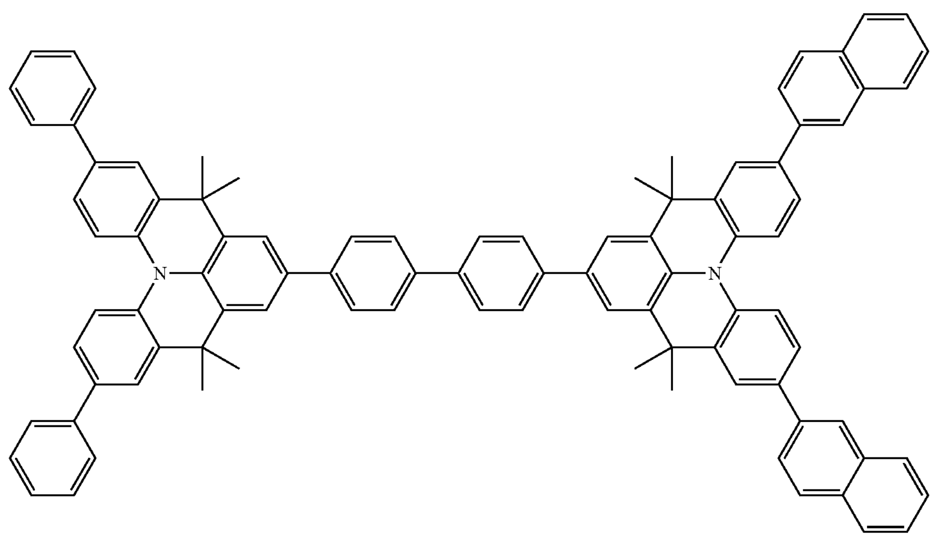 [SMILES: CC1(C)c2cc(-c3ccccc3)ccc2N2c3ccc(-c4ccccc4)cc3C(C)(C)c3cc(-c4ccc(-c5ccc(-c6cc7c8c(c6)C(C)(C)c6cc(-c9ccc%10ccccc%10c9)ccc6N8c6ccc(-c8ccc9ccccc9c8)cc6C7(C)C)cc5)cc4)cc1c32] |
| 107 | 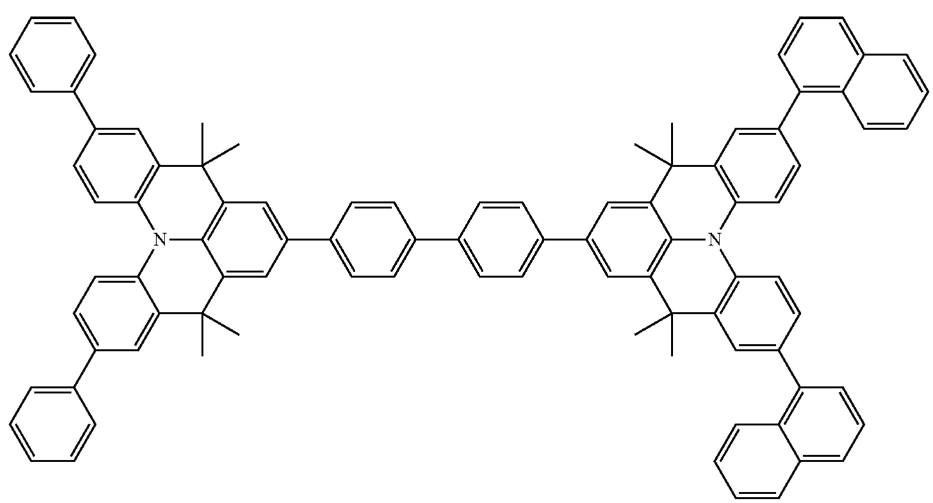 [SMILES: CC1(C)c2cc(-c3ccccc3)ccc2N2c3ccc(-c4ccccc4)cc3C(C)(C)c3cc(-c4ccc(-c5ccc(-c6cc7c8c(c6)C(C)(C)c6cc(-c9cccc%10ccccc9%10)ccc6N8c6ccc(-c8cccc9ccccc89)cc6C7(C)C)cc5)cc4)cc1c32] |

TABLE 3-continued
| No. | Structure |
|---|---|
| 108 | 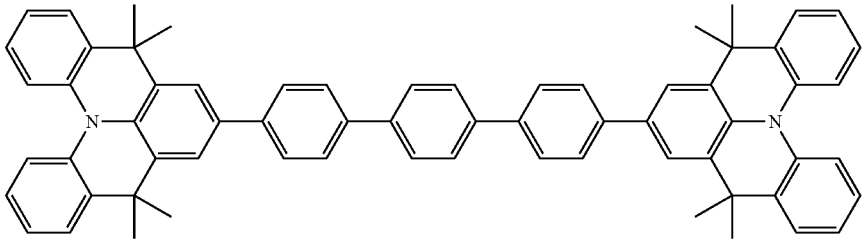 [SMILES: CC1(C)c2ccccc2N2c3ccccc3C(C)(C)c3cc(-c4ccc(-c5ccc(-c6ccc(-c7cc8c9c(c7)C(C)(C)c7ccccc7N9c7ccccc7C8(C)C)cc6)cc5)cc4)cc1c32] |
| 109 | 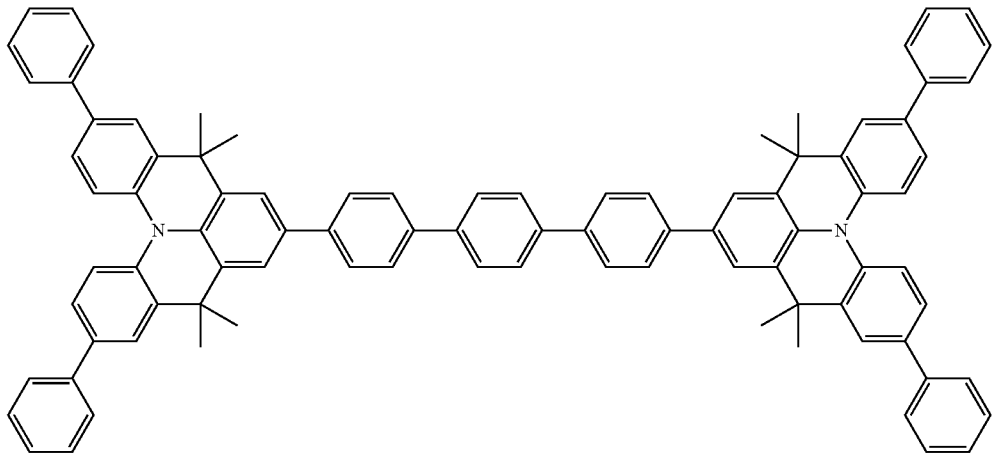 [SMILES: CC1(C)c2cc(-c3ccccc3)ccc2N2c3ccc(-c4ccccc4)cc3C(C)(C)c3cc(-c4ccc(-c5ccc(-c6ccc(-c7cc8c9c(c7)C(C)(C)c7cc(-c%10ccccc%10)ccc7N9c7ccc(-c9ccccc9)cc7C8(C)C)cc6)cc5)cc4)cc1c32] |
| 110 | 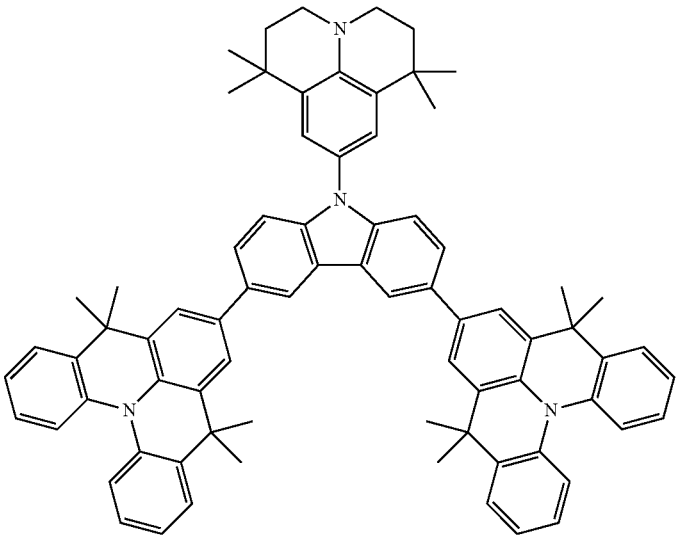 [SMILES: CC1(C)CCN2CCC(C)(C)c3cc(-n4c5ccc(-c6cc7c8c(c6)C(C)(C)c6ccccc6N8c6ccccc6C7(C)C)cc5c5cc(-c6cc7c8c(c6)C(C)(C)c6ccccc6N8c6ccccc6C7(C)C)ccc54)cc1c32] |

TABLE 3-continued

| No. | Structure |
|---|---|
| 111 | 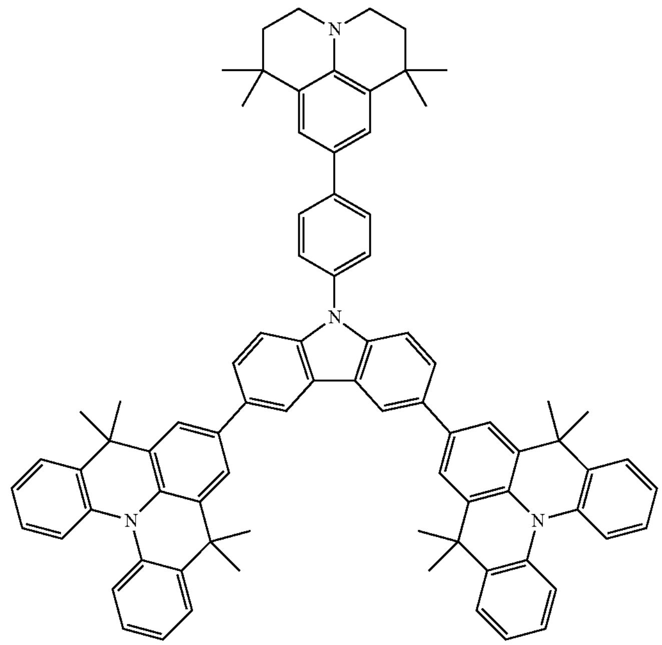 [SMILES: CC1(C)CCN2CCC(C)(C)c3cc(-c4ccc(-n5c6ccc(-c7cc8c9c(c7)C(C)(C)c7ccccc7N9c7ccccc7C8(C)C)cc6c6cc(-c7cc8c9c(c7)C(C)(C)c7ccccc7N9c7ccccc7C8(C)C)ccc65)cc4)cc1c32] |
| 112 | 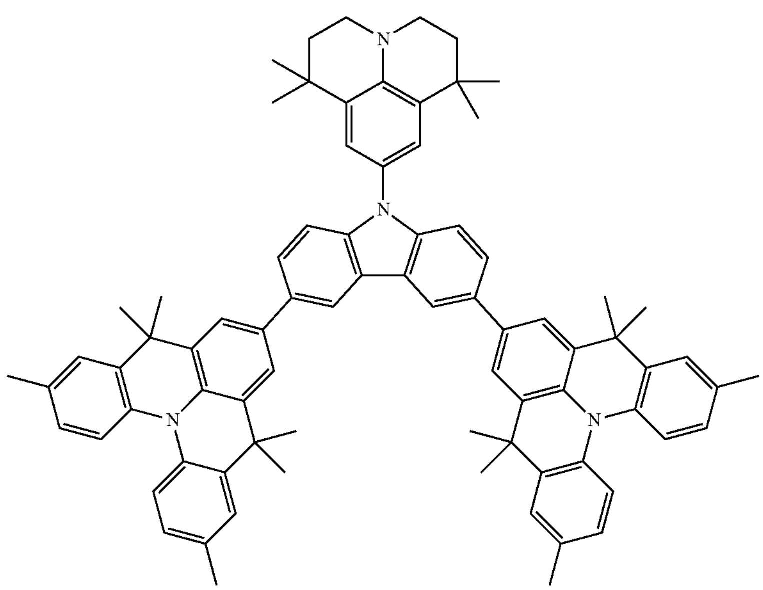 |

Hereinafter, a light emitting device including the novel compound according to the present invention will be described with reference to the accompanying drawings. The structure of the light emitting device including the compound is not limited by the accompanying drawings and the following description. The drawings illustrate a structure including an organic layer including the compound according to the present invention in which a light emitting device is disposed between one electrode and a light emitting layer, and the structure will be described.

FIG. 1 is a cross-sectional view for describing a light emitting device according to an exemplary embodiment of the present invention.

Referring to FIG. 1, a light emitting device 100 includes a first electrode 20, a hole transport layer 30, a light emitting layer 40, and a second electrode 50, which are formed on a base substrate 10. The light emitting device 100 may be an organic light emitting diode (OLED).

The first electrode 20 may be formed of a conductive material on the base substrate 10. As an example, the first electrode 20 may be a transparent electrode. In this case, the first electrode 20 may be formed of indium tin oxide (ITO). In contrast, the first electrode 20 may be an opaque (reflective) electrode. In this case, the first electrode 20 may have an ITO/silver (Ag)/ITO structure. The first electrode 20 may become an anode of the light emitting device 100.

The hole transport layer 30 is an organic layer which is formed on the first electrode 20 to be interposed between the first electrode 20 and the light emitting layer 40, and includes a compound represented by the following Formula 1. That is, the organic layer interposed between the first electrode 20 and the light emitting layer 40 may be the hole transport layer 30.

[Formula 1]

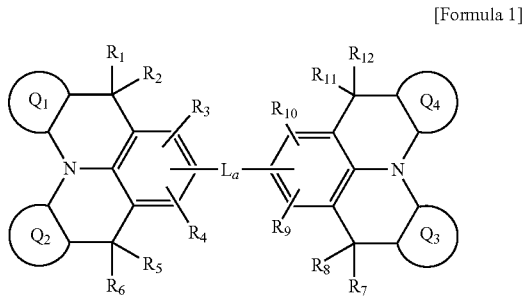

The compound represented by Formula 1 is a novel compound according to the present invention and may be substantially the same as those described above. Therefore, an overlapping specific description for each of $L_a$, $R_1$ to $R_{12}$, and $Q_1$ to $Q_4$ will be omitted.

The wavelength of light which the light emitting layer 40 emits may vary according to the kind of compound which forms the light emitting layer 40.

The second electrode 50 may be formed of a conductive material on the light emitting layer 40. When the first electrode 20 is a transparent electrode, the second electrode 50 may be an opaque (reflective) electrode. In this case, the second electrode 50 may be an aluminum electrode. In contrast, when the first electrode 20 is an opaque electrode, the second electrode 50 may be a transparent or semi-transparent electrode. In this case, the second electrode 50 may have a thickness of 100 Å to 150 Å, and may be an alloy including magnesium and silver. The second electrode 50 may become a cathode of the light emitting device 100.

Between the light emitting layer 40 and the second electrode 50, an electron transporting layer and/or an electron injecting layer may be formed as an electron transport layer.

When current flows between the first and second electrodes 20 and 50 of the light emitting device 100, a hole injected from the first electrode 20 to the light emitting layer 40 and an electron injected from the second electrode 50 to the light emitting layer 40 combine with each other to form an exciton. While the exciton is transferred to a bottom state, light having a wavelength at a specific band is produced. In this case, the exciton may be a singlet exciton, and may also be a triplet exciton. Accordingly, the light emitting device 100 may provide light to the outside.

Even though not illustrated in the drawing, the light emitting device 100 may further include an electron transporting layer (ETL) and an electron injecting layer (EIL), which are disposed between the light emitting layer 40 and the second electrode 50. The electron transporting layer and the electron injecting layer may be sequentially stacked and formed on the light emitting layer 40.

Further, the light emitting device 100 may further include a first blocking layer (not illustrated) disposed between the first electrode 20 and the light emitting layer 40 and/or a second blocking layer (not illustrated) disposed between the light emitting layer 40 and the second electrode 50.

For example, the first blocking layer may be an electron blocking layer (EBL) which is disposed between the hole transport layer 30 and the light emitting layer 40 and thus prevents electrons injected from the second electrode 50 from flowing into the hole transport layer 30 via the light emitting layer 40. In addition, the first blocking layer may be an exciton blocking layer which prevents an exciton formed in the light emitting layer 40 from being diffused in a direction of the first electrode 20 and thus being non-radiatively decayed. Furthermore, the first blocking layer may be an exciton dissociation blocking layer (EDBL). The exciton dissociation blocking layer may prevent an exciton formed in the light emitting layer from being non-radiatively decayed through the process of 'exciton dissociation' at the interface between the light emitting layer 40 and the hole transport layer 30. In order to prevent exciton dissociation at the interface, a compound which forms the first blocking layer may be selected so as to have a HOMO value at a level similar to that of a compound which forms the light emitting layer 40.

In this case, the first blocking layer may include the compound according to the present invention, which is described above.

The second blocking layer may be a hole blocking layer (HBL) which is disposed between the light emitting layer 40 and the second electrode 50, specifically, the light emitting layer 40 and the electron transporting layer, and thus, prevents holes from flowing into the electron transporting layer via the light emitting layer 40 from the first electrode 20. Further, the second blocking layer may be an exciton blocking layer which prevents an exciton formed in the light emitting layer 40 from being diffused in a direction of the second electrode 50 and thus being non-radiatively decayed.

When the thickness of each of the first and second blocking layers is adjusted so as to be suitable for the resonance length of the light emitting device 100, the light emitting efficiency may be increased, and the exciton may be adjusted so as to be formed in the central part of the light emitting layer 40.

Referring to FIG. 2, a light emitting device 102 includes a first electrode 20, a hole transport layer 32, a light emitting layer 40, and a second electrode 50, which are formed on a base substrate 10. Except for the hole transport layer 32, the other constituent elements are substantially the same as those described in FIG. 1, and thus the overlapping description thereof will be omitted.

The hole transport layer 32 includes the compound represented by Formula 1 and a P-type dopant. That is, an organic layer including the compound according to the present invention may be the hole transport layer 32 which further includes a P-type dopant. Since a compound included in the hole transport layer 32 is substantially the same as that described above, the overlapping specific description thereof will be omitted.

The P-type dopant may include a P-type organic dopant and/or a P-type inorganic dopant.

Specific examples of the P-type organic dopant include compounds represented by the following Formulae 4 to 8, hexadecafluorophthalocyanine (F16CuPc), 11,11,12,12-tetracyanonaphtho-2,6-quinodimethane (TNAP), 3,6-difluoro-2,5,7,7,8,8-hexacyano-quinodimethane (F2-HCNQ), or tetracyanoquinodimethane (TCNQ), and the like. These may be used either alone or in combination of two or more thereof.

[Formula 4]

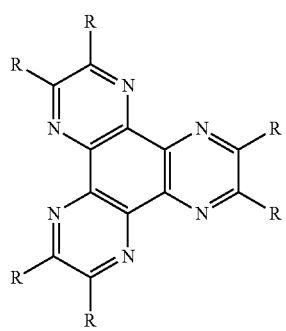

In Formula 4, R may represent a cyano group, a sulfone group, a sulfoxide group, a sulfonamide group, a sulfonate group, a nitro group, or a trifluoromethyl group.

[Formula 5]

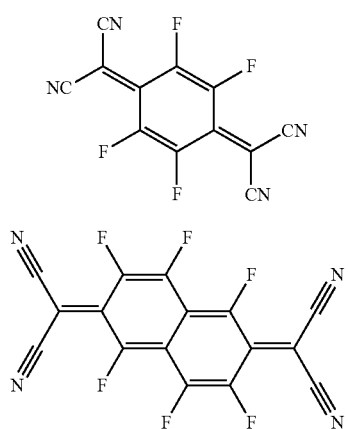

[Formula 6]

[Formula 7]

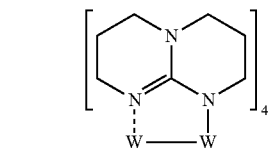

[Formula 8]

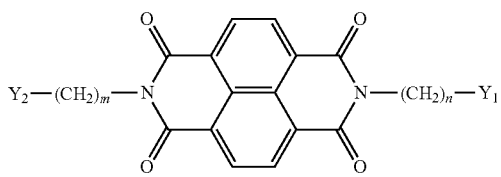

In Formula 8, m and n each independently represent an integer of 1 to 5, and $Y_1$ and $Y_2$ may each independently represent an aryl group having 6 to 20 carbon atoms, or a heteroaryl group having 2 to 20 carbon atoms. In this case, a hydrogen atom of the aryl group or heteroaryl group represented by $Y_1$ and $Y_2$ may be unsubstituted or substituted with an alkyl group having 1 to 5 carbon atoms, an alkoxy group having 1 to 5 carbon atoms, or a hydroxyl group, and hydrogen atoms of substituted or unsubstituted $Y_1$ and $Y_2$ may be each independently unsubstituted or substituted with a halogen group.

For example, the compound represented by Formula 8 may include a compound represented by the following Formula 8a or the following Formula 8b.

[Formula 8a]

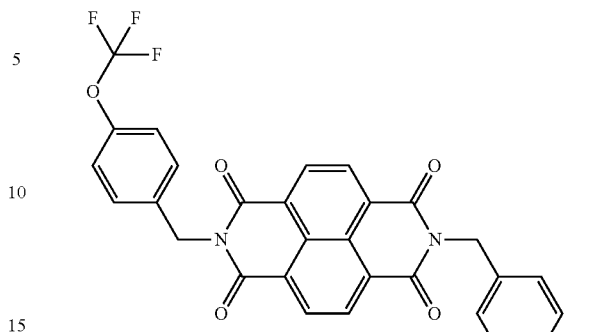

[Formula 8b]

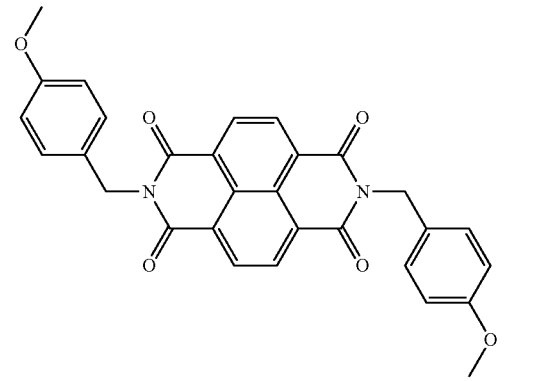

Examples of the P-type inorganic dopant include metal oxide or metal halide, and the like. Specific examples of the P-type inorganic dopant include $MoO_3$, $V_2O_5$, $WO_3$, $SnO_2$, $ZnO$, $MnO_2$, $CoO_2$, $ReO_3$, $TiO_2$, $FeCl_3$, $SbCl_5$ or $MgF_2$, and the like. These may be used either alone or in combination of two or more thereof.

The content of the P-type dopant may be about 0.5 part by weight to about 20 parts by weight based on 100 parts by weight of the novel compound according to the present invention, which is a hole transport compound. For example, the content of the P-type dopant may be about 0.5 part by weight to about 15 parts by weight, or about 0.5 part by weight to about 5 parts by weight, based on 100 parts by weight of the hole transport compound. In contrast, the content of the P-type dopant may be about 1 part by weight to about 10 parts by weight, about 1 part by weight to about 5 parts by weight, about 1.5 parts by weight to about 6 parts by weight, or about 2 parts by weight to about 5 parts by weight, based on 100 parts by weight of the hole transport compound.

When the content of the P-type dopant is about 0.5 part by weight to about 20 parts by weight based on 100 parts by weight of the hole transport compound, the P-type dopant may prevent an excessive leakage current from being generated without degrading physical properties of the hole transport compound. In addition, the energy barrier at the interface with each of the upper and lower layers, which are brought into contact with the hole transport layer 32, may be reduced by the P-type dopant.

Even though not illustrated in the drawing, the light emitting device 102 may further include an electron transporting layer, an electron injecting layer, a first blocking layer, and/or a second blocking layer. Since the layers are substantially the same as those described in the light emitting device 100 of FIG. 1, the specific description thereof will be omitted. When the light emitting device 102 includes the first blocking layer, the first blocking layer may include the compound according to the present invention, which is described above.

Meanwhile, the light emitting device 100 illustrated in FIG. 1 may further include an interlayer (not illustrated). The interlayer may be disposed between the first electrode 20 and the hole transport layer 30 of FIG. 1, and may be formed of the compound used as the P-type dopant described in FIG. 2.

Referring to FIG. 3, a light emitting device 104 includes a first electrode 20, a hole transport layer 34, a light emitting layer 40, and a second electrode 50, which are formed on a base substrate 10. Except for the hole transport layer 34, the other constituent elements are substantially the same as those described in FIG. 1, and thus the overlapping description thereof will be omitted.

The hole transport layer 34 includes a first layer 33a brought into contact with the first electrode 20 and a second layer 33b disposed between the first layer 33a and the light emitting layer 40. That is, the hole transport layer 34 may have a two-layer structure as an organic layer including the compound according to the present invention. Furthermore, the hole transport layer 34 may have a multi-layer structure having two or more layers, which includes the first and second layers 33a and 33b.

The first and second layers 33a and 33b may include the same kind of hole transport compound. Since components of the hole transport compound included in the first layer 33a and the second layer 33b are made identical to each other, physical and chemical defects which may be generated at the interface between different species materials may be reduced, thereby facilitating injection of holes into the light emitting layer. In another aspect, when the same host material is used for the first layer 33a and the second layer 33b, there are advantages in that the first layer 33a and the second layer 33b may be continuously formed within one chamber, so that the manufacturing process may be simplified and the manufacturing time may be shortened. Furthermore, physical properties such as the glass transition temperature become similar to each other between the adjacent layers, so that there is also an advantage in that durability of the device may be increased.

The first layer 33a includes the novel compound according to the present invention, which is represented by Formula 1, as the hole transport compound, and a P-type dopant. Except for the thickness, the first layer 33a is substantially the same as the hole transport layer 32 described in FIG. 2. Therefore, the overlapping description thereof will be omitted.

The second layer 33b includes the novel compound according to the present invention, which is represented by Formula 1, as the hole transport compound, but the hole transport compound which constitutes the second layer 33b may be the same as the hole transport compound which constitutes the first layer 33a. Except for the thickness, the second layer 33b is also substantially the same as the hole transport layer 30 described in FIG. 1, and thus the overlapping detailed description thereof will be omitted.

In contrast, the first and second layers 33a and 33b may include a different kind of hole transport compound. The hole transport compound, which constitutes the first and second layers 33a and 33b, is the novel compound according to the present invention, which is represented by Formula 1, but $L_a$, $R_1$ to $R_{12}$, and $Q_1$ to $Q_4$ may be each independently different from each other. In this case, the compound, which constitutes each of the first and second layers 33a and 33b, may be selected so as to have a HOMO value for efficiently transferring holes to the light emitting layer 40.

Additionally, the second layer 33b may further include a P-type dopant together with the hole transport compound. In this case, the kinds of P-type dopants doped in the first layer 33a and the second layer 33b may be different from each other, and an amount of doping may vary even though the same kind of P-type dopants are used. For example, a content (P1) of the P-type dopant doped in the first layer 33a and a content (P2) of the P-type dopant doped in the second layer 33b may satisfy the relationship of the following Equation 1.

$$P1/P2 \geq 1 \quad \text{[Equation 1]}$$

In Equation 1, 'P1' is a content of the P-type dopant doped in the first layer 33a based on 100 parts by weight of the hole transport compound, and "P2" is a content of the P-type dopant doped in the second layer 33b based on 100 parts by weight of the hole transport compound.

For example, the content of the P-type dopant doped in the first layer 33a may range from 0.3 to 20 parts by weight, 1 to 15 parts by weight, 2 to 10 parts by weight, or 4 to 6 parts by weight, based on 100 parts by weight of the hole transport compound. Further, the content of the P-type dopant doped in the second layer 33b may range from 0.3 to 20 parts by weight, 0.5 to 10 parts by weight, 1 to 8 parts by weight, or 2 to 4 parts by weight, based on 100 parts by weight of the hole transport compound.

In addition, even though not illustrated in the drawing, the light emitting device 104 may further include an electron transporting layer, an electron injecting layer, a first blocking layer, and/or a second blocking layer. Since the layers are substantially the same as those described in the light emitting device 100 of FIG. 1, the specific description thereof will be omitted.

Each of the light emitting devices 100, 102, and 104 described above includes the novel compound according to the present invention, which is represented by Formula 1, and thus the light emitting devices 100, 102, and 104 may have enhanced light emitting efficiency and an increased lifespan.

Meanwhile, even though not illustrated in the drawing, the light emitting device according to the present invention may include an organic layer including the compound represented by Formula 1 as a blocking layer. That is, the hole transport layer includes a hole transport compound which may be easily obtained by the person skilled in the art, and a blocking layer including the compound represented by Formula 1 according to the present invention may be disposed between the hole transport layer and the light emitting layer.

FIGS. 1 to 3 illustrate that the light emitting devices 100, 102, and 104 are directly formed on the base substrate 10, but a thin film transistor may be disposed as a driving device, which drives pixels, between the first electrode 20 of each of the light emitting devices 100, 102, and 104 and the base substrate 10. In this case, the first electrode 20 may become a pixel electrode connected to the thin film transistor. When the first electrode 20 is a pixel electrode, the first electrodes 20 are disposed spaced apart from each other in each of a plurality of pixels, and a partition wall pattern formed along the edge of the first electrode 20 is formed on the base substrate 10, so that layers to be stacked on the first electrode 20, which are disposed on the pixels adjacent to each other, may be isolated from each other. That is, even though not illustrated in the drawings, the light emitting devices 100, 102, and 104 may be used for a display device which displays an image without a backlight.

Furthermore, the light emitting devices 100, 102, and 104 may be used as a lighting device.

As described above, the light emitting devices 100, 102, and 104 exemplified in the present invention may be used for various electronic devices such as the display device or the lighting device.

EXAMPLES

Hereinafter, novel compounds according the present invention will be described in more detail through specific Examples according to the present invention. The Examples to be exemplified below are only provided for the detailed description of the invention, but are not intended to limit the right scope thereby.

Example 1

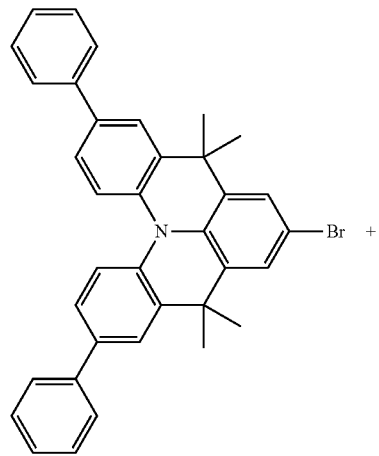

Compound A

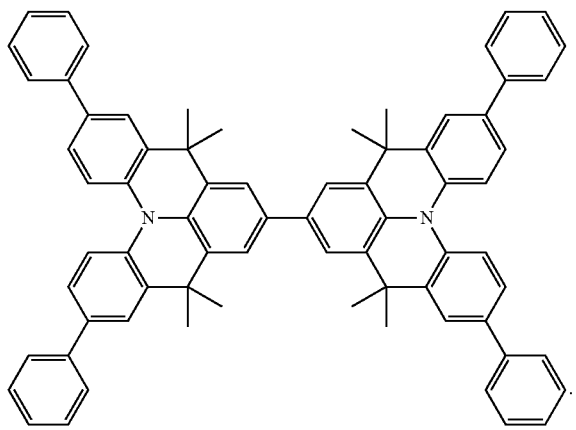

Compound 1

A 500 mL three-neck round-bottom flask was filled with nitrogen, and then Compound A (30.5 mmol, 17.0 g), Compound B (33.6 mmol, 20.3 g), 170 mL of tetrahydrofuran (THF), and 85 mL of ethanol (EtOH) were added thereto, and the resulting mixture was stirred for 30 minutes. Further, potassium carbonate ($K_2CO_3$) (122.2 mmol, 16.9 g) was dissolved in 85 mL of water ($H_2O$), and then the resulting solution was added to the 500 mL three-neck round-bottom flask. Subsequently, tetrakis(triphenylphosphine)palladium ($Pd(PPh_3)_4$) (1.2 mmol, 1.4 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of THF, and the resulting solution was put into 850 mL of methanol and stirred for 20 minutes, and then filtered, thereby obtaining 21.8 g of a pale green solid Compound 1 (yield 75%).

MALDI-TOF: m/z=952.4825 ($C_{72}H_{60}N_2$=952.48)

Example 2

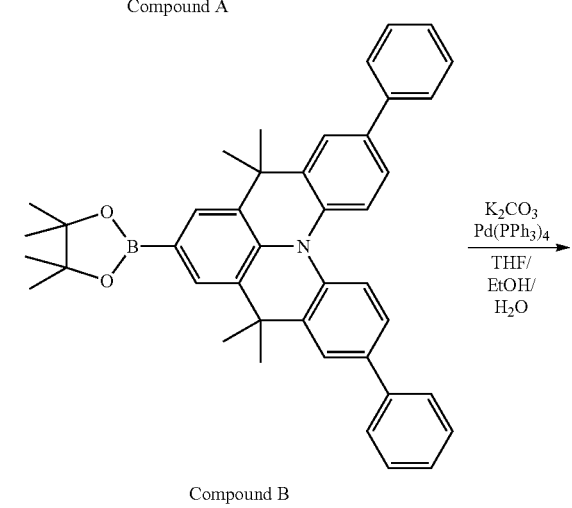

Compound B

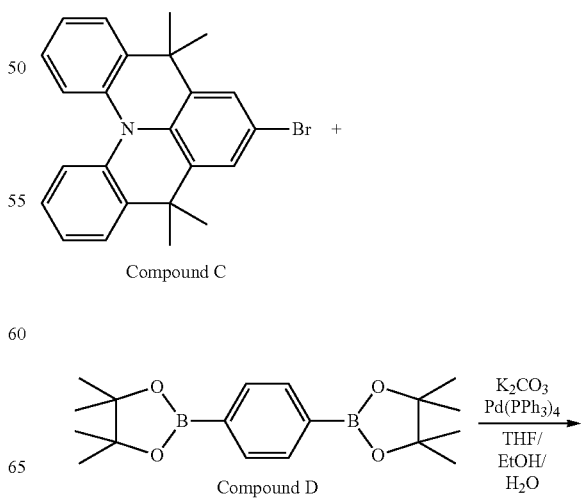

Compound C

Compound D

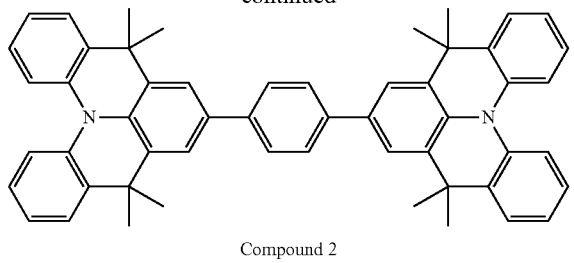

Compound 2

A 500 mL three-neck round-bottom flask was filled with nitrogen, and then Compound C (49.5 mmol, 20.0 g), Compound D (22.5 mmol, 7.4 g), 200 mL of tetrahydrofuran (THF), and 100 mL of ethanol (EtOH) were added thereto, and the resulting mixture was stirred for 30 minutes. Further, potassium carbonate (K$_2$CO$_3$) (179.9 mmol, 24.9 g) was dissolved in 100 mL of water (H$_2$O), and then the resulting solution was added to the 500 mL three-neck round-bottom flask. Subsequently, tetrakis(triphenylphosphine)palladium (Pd(PPh$_3$)$_4$) (1.8 mmol, 2.1 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 100 mL of tetrahydrofuran (THF), and the resulting solution was put into 1,000 mL of methanol and stirred for 20 minutes, and then filtered, thereby obtaining about 12.7 g of a yellow solid Compound 2 (yield 78%).

MALDI-TOF: m/z=724.3829 (C$_{54}$H$_{48}$N$_2$=724.38)

Example 3

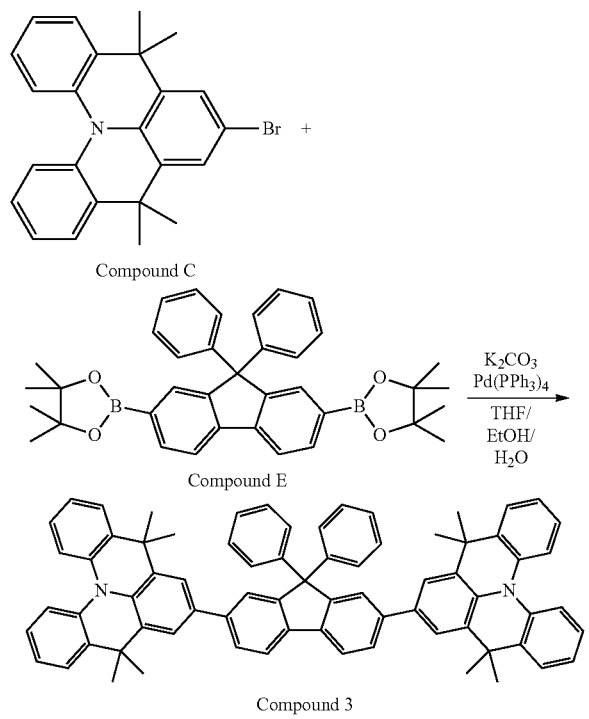

Compound 3

A 500 mL three-neck round-bottom flask was filled with nitrogen, and then Compound C (61.8 mmol, 25.0 g), Compound E (28.1 mmol, 16.0 g), 250 mL of tetrahydrofuran (THF), and 125 mL of ethanol (EtOH) were added thereto, and the resulting mixture was stirred for 30 minutes. Further, potassium carbonate (K$_2$CO$_3$) (224.8 mmol, 31.1 g) was dissolved in 125 mL of water (H$_2$O), and then the resulting solution was added to the 500 mL three-neck round-bottom flask. Subsequently, tetrakis(triphenylphosphine)palladium (Pd(PPh$_3$)$_4$) (2.2 mmol, 2.6 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 125 mL of tetrahydrofuran (THF), the resulting solution was put into 1,250 mL of methanol, stirred for 20 minutes, and then filtered, thereby obtaining about 19.0 g of a white solid Compound 3 (yield 70%).

MALDI-TOF: m/z=964.4845 (C$_{73}$H$_{60}$N$_2$=964.48)

Example 4

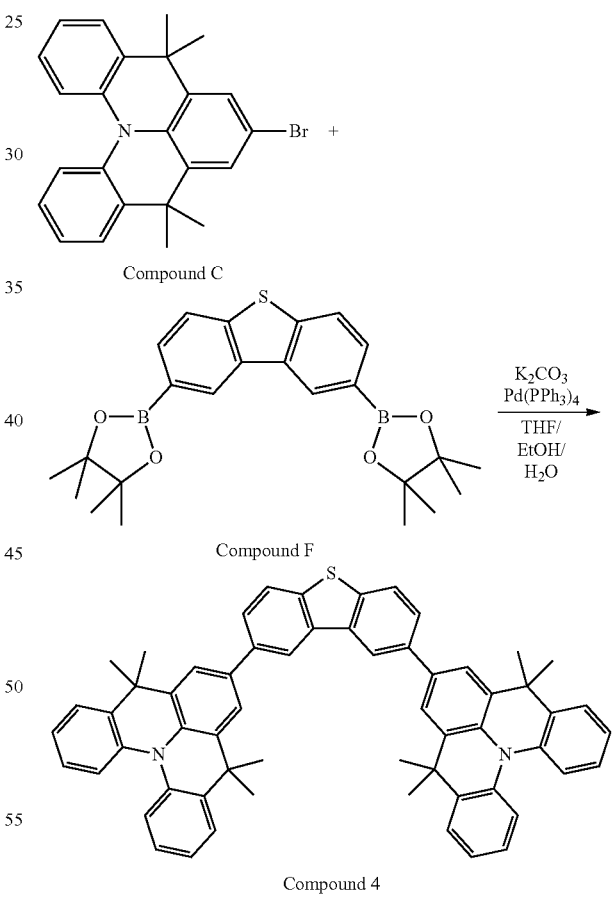

Compound 4

A 500 mL three-neck round-bottom flask was filled with nitrogen, and then Compound C (74.2 mmol, 30.0 g), Compound F (33.7 mmol, 14.7 g), 300 mL of tetrahydrofuran (THF), and 150 mL of ethanol (EtOH) were added thereto, and the resulting mixture was stirred for 30 minutes. Further, potassium carbonate (K$_2$CO$_3$) (269.8 mmol, 37.3 g) was dissolved in 150 mL of water (H$_2$O), and then the resulting solution was added to the 500 mL three-neck round-bottom flask. Subsequently, tetrakis(triphenylphosphine)palladium (Pd(PPh$_3$)$_4$) (2.7 mmol, 3.1 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 150 mL of tetrahydrofuran (THF), and the resulting solution was put into 1,500 mL of methanol and stirred for 20 minutes, and then filtered, thereby obtaining about 22.4 g of a pale green solid Compound 4 (yield 80%).

MALDI-TOF: m/z=830.3746 (C$_{60}$H$_{50}$N$_2$S=830.37)

Example 5

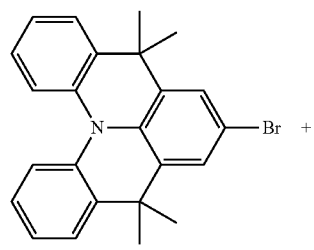

Compound C

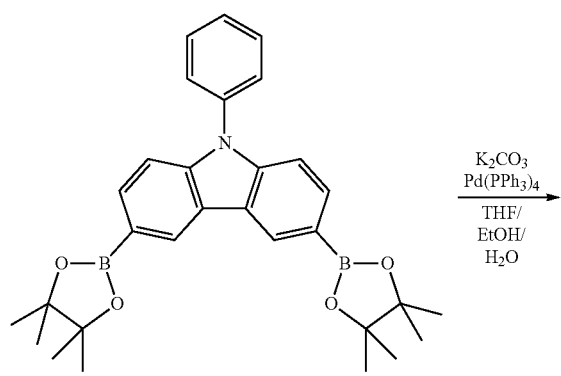

Compound G

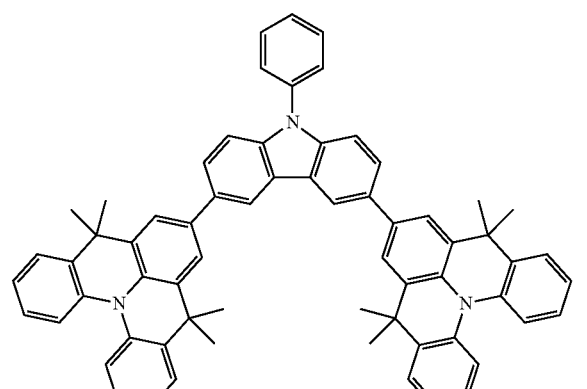

Compound 5

A 500 mL three-neck round-bottom flask was filled with nitrogen, and then Compound C (61.8 mmol, 25.0 g), Compound G (28.1 mmol, 13.9 g), 250 mL of tetrahydrofuran (THF), and 125 mL of ethanol (EtOH) were added thereto, and the resulting mixture was stirred for 30 minutes. Further, potassium carbonate (K$_2$CO$_3$) (224.8 mmol, 31.1 g) was dissolved in 125 mL of water (H$_2$O), and then the resulting solution was added to the 500 mL three-neck round-bottom flask. Subsequently, tetrakis(triphenylphosphine)palladium (Pd(PPh$_3$)$_4$) (2.2 mmol, 2.6 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 125 mL of tetrahydrofuran (THF), and the resulting solution was put into 1,250 mL of methanol and stirred for 20 minutes, and then filtered, thereby obtaining 21.3 g of a pale brown solid Compound 5 (yield 85%).

MALDI-TOF: m/z=889.4431 (C$_{66}$H$_{55}$N$_3$=889.44)

Example 6

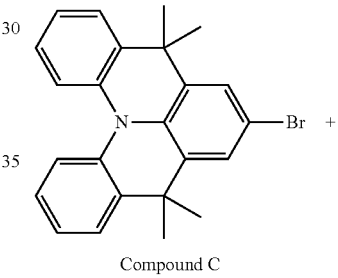

Compound C

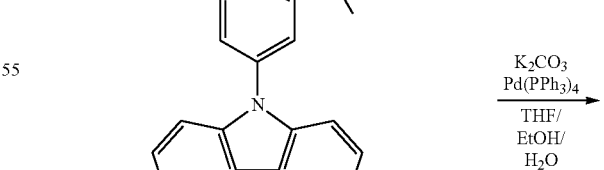

Compound H

-continued

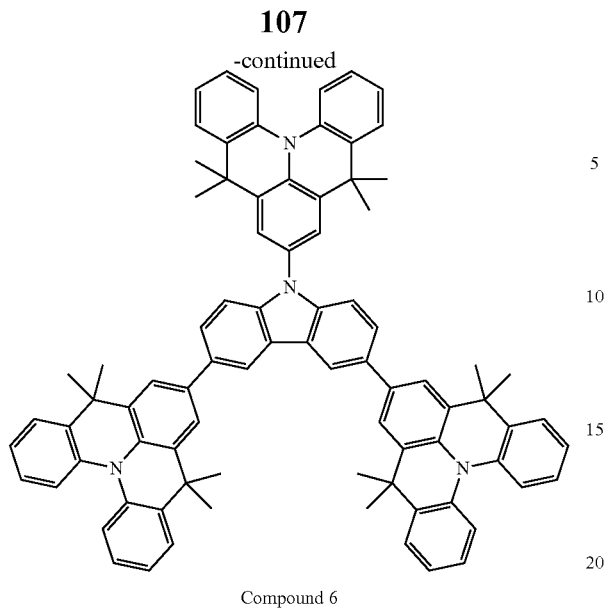

Compound 6

A 500 mL three-neck round-bottom flask was filled with nitrogen, and then Compound C (49.5 mmol, 20.0 g), Compound H (22.5 mmol, 18.3 g), 200 mL of tetrahydrofuran (THF), and 100 mL of ethanol (EtOH) were added thereto, and the resulting mixture was stirred for 30 minutes. Further, potassium carbonate ($K_2CO_3$) (179.9 mmol, 24.9 g) was dissolved in 100 mL of water ($H_2O$), and then the resulting solution was added to the 500 mL three-neck round-bottom flask. Subsequently, tetrakis(triphenylphosphine)palladium ($Pd(PPh_3)_4$) (1.8 mmol, 2.1 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 100 mL of tetrahydrofuran (THF), the resulting solution was put into 1,000 mL of methanol, stirred for 20 minutes, and then filtered, thereby obtaining about 21.5 g of a white solid Compound 6 (yield 84%).

MALDI-TOF: m/z=1136.5843 ($C_{84}H_{72}N_4$=1136.58)

Example 7

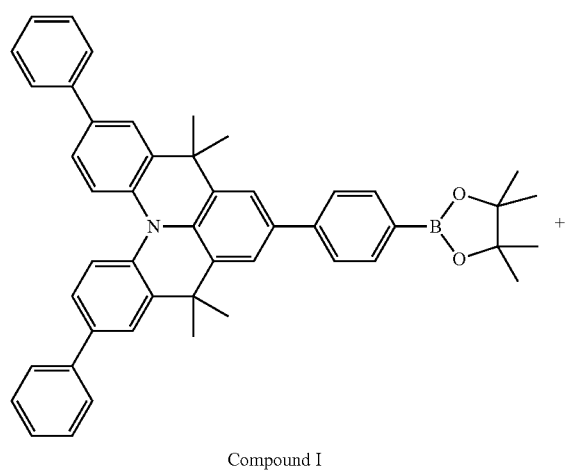

Compound I

-continued

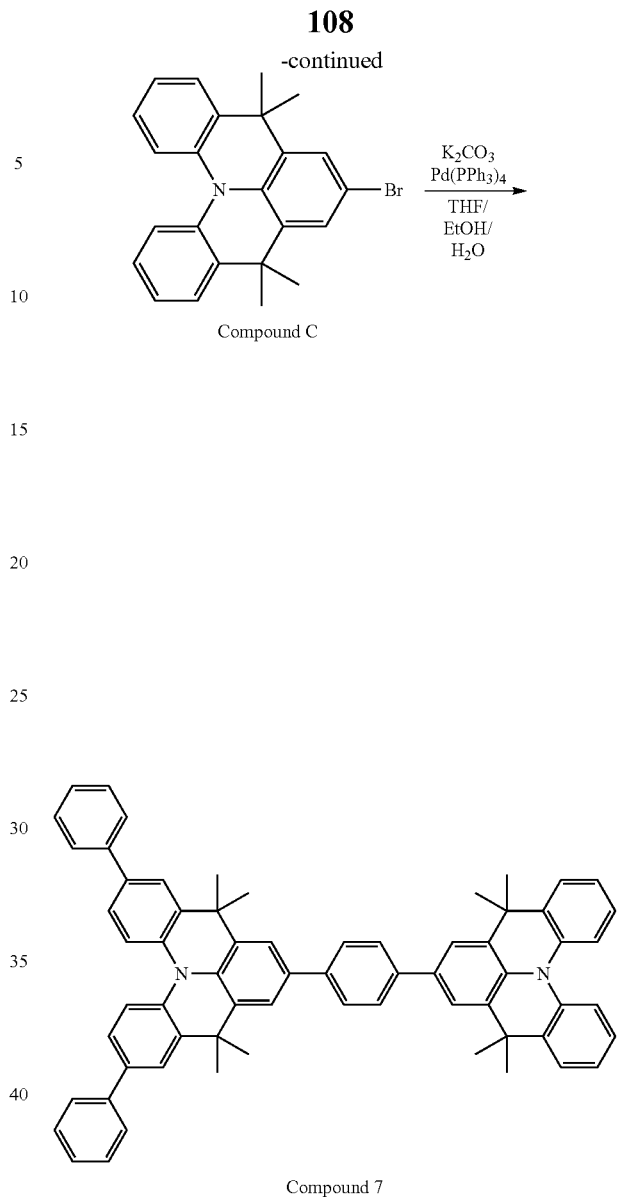

Compound C

Compound 7

A 500 mL three-neck round-bottom flask was filled with nitrogen, and then Compound I (21.1 mmol, 17.0 g), Compound C (23.2 mmol, 9.4 g), 170 mL of tetrahydrofuran (THF), and 85 mL of ethanol (EtOH) were added thereto, and the resulting mixture was stirred for 30 minutes. Further, potassium carbonate ($K_2CO_3$) (84.3 mmol, 11.7 g) was dissolved in 85 mL of water ($H_2O$), and then the resulting solution was added to the 500 mL three-neck round-bottom flask. Subsequently, tetrakis(triphenylphosphine)palladium ($Pd(PPh_3)_4$) (0.8 mmol, 1.0 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 85 mL of tetrahydrofuran (THF), and the resulting solution was put into 850 mL of methanol and stirred for 20 minutes, and then filtered, thereby obtaining about 13.3 g of a pale green solid Compound 7 (yield 72%).

MALDI-TOF: m/z=876.4433 ($C_{66}H_{56}N_2$=876.44)

Example 8

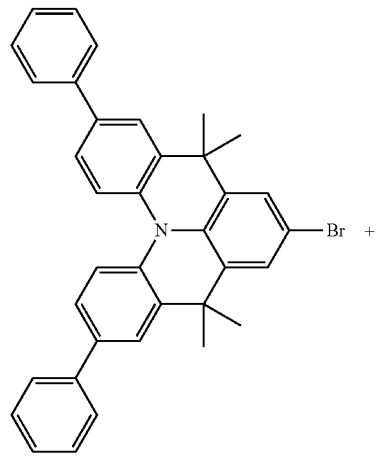

Compound J

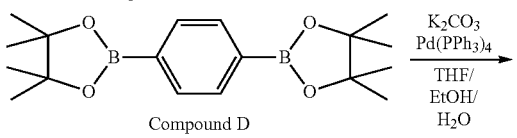

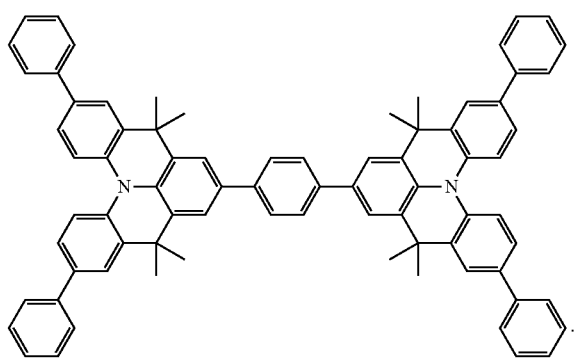

Compound 8

A 500 mL three-neck round-bottom flask was filled with nitrogen, and then Compound J (53.9 mmol, 30.0 g), Compound D (24.5 mmol, 8.1 g), 300 mL of tetrahydrofuran (THF), and 150 mL of ethanol (EtOH) were added thereto, and the resulting mixture was stirred for 30 minutes. Further, potassium carbonate ($K_2CO_3$) (196.0 mmol, 27.1 g) was dissolved in 150 mL of water ($H_2O$), and then the resulting solution was added to the 500 mL three-neck round-bottom flask. Subsequently, tetrakis(triphenylphosphine)palladium ($Pd(PPh_3)_4$) (2.0 mmol, 2.3 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 150 mL of tetrahydrofuran (THF), and the resulting solution was put into 1,500 mL of methanol and stirred for 20 minutes, and then filtered, thereby obtaining about 19.4 g of a pale brown solid Compound 8 (yield 77%).

MALDI-TOF: m/z=1028.5134 ($C_{78}H_{64}N_2$=1028.51)

Example 9

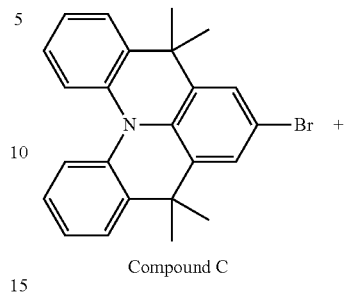

Compound C

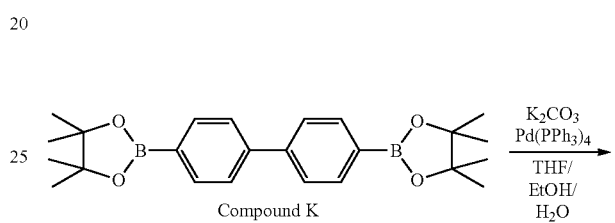

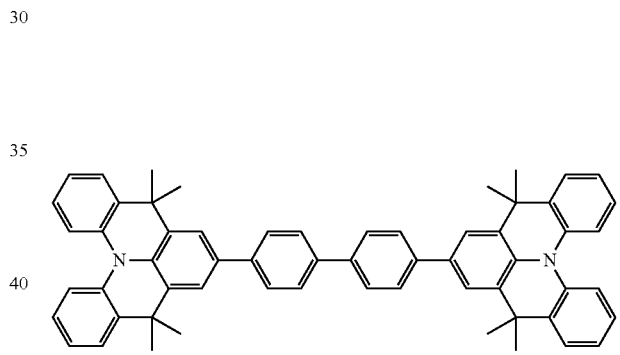

Compound 9

A 500 mL three-neck round-bottom flask was filled with nitrogen, and then Compound C (69.2 mmol, 28.0 g), Compound K (31.5 mmol, 12.8 g), 280 mL of tetrahydrofuran (THF), and 140 mL of ethanol (EtOH) were added thereto, and the resulting mixture was stirred for 30 minutes. Further, potassium carbonate ($K_2CO_3$) (251.8 mmol, 34.8 g) was dissolved in 140 mL of water ($H_2O$), and then the resulting solution was added to the 500 mL three-neck round-bottom flask. Subsequently, tetrakis(triphenylphosphine)palladium ($Pd(PPh_3)_4$) (2.5 mmol, 2.9 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 140 mL of tetrahydrofuran (THF), and the resulting solution was put into 1,400 mL of methanol and stirred for 20 minutes, and then filtered, thereby obtaining about 19.9 g of a pale green solid Compound 9 (yield 79%).

MALDI-TOF: m/z=800.4123 ($C_{60}H_{52}N_2$=800.41)

Example 10

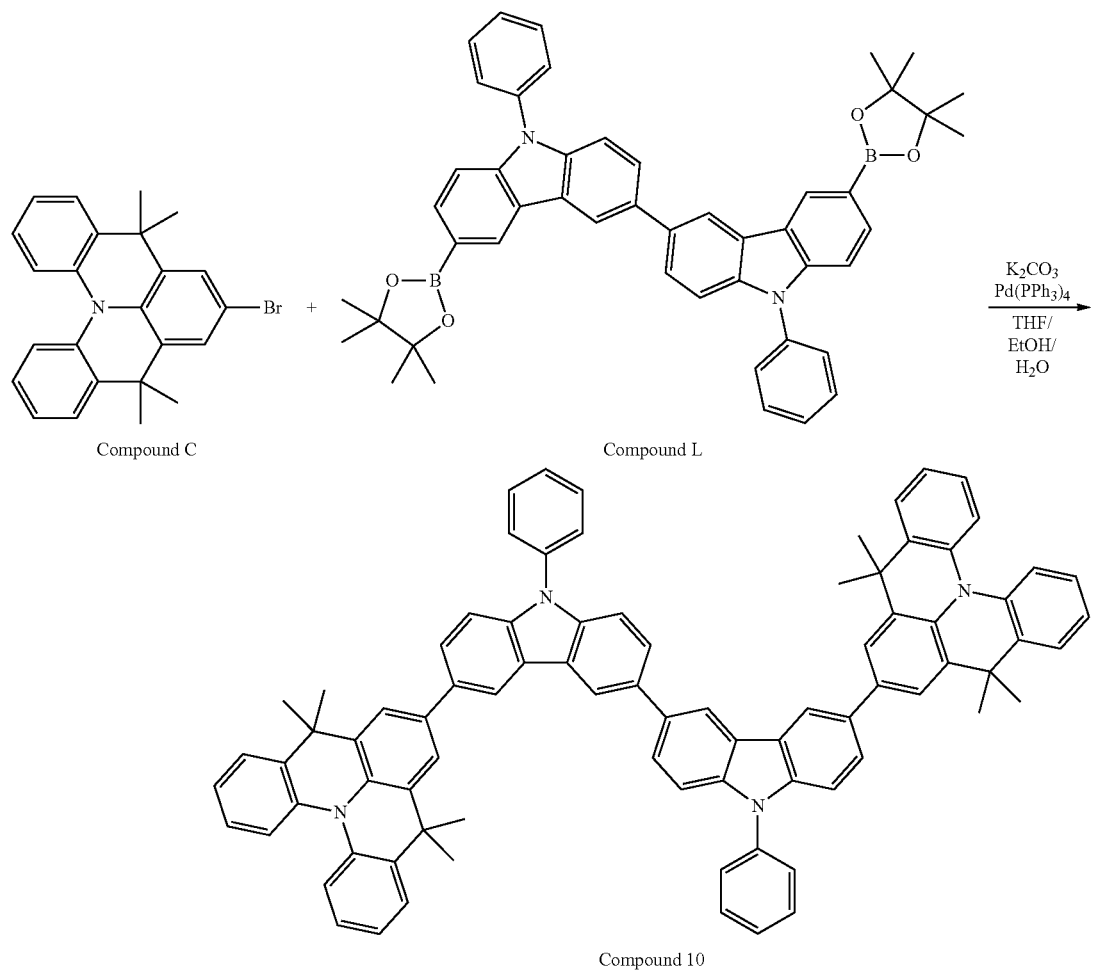

A 500 mL three-neck round-bottom flask was filled with nitrogen, and then Compound C (54.4 mmol, 22.0 g), Compound L (24.7 mmol, 18.2 g), 220 mL of tetrahydrofuran (THF), and 110 mL of ethanol (EtOH) were added thereto, and the resulting mixture was stirred for 30 minutes. Further, potassium carbonate ($K_2CO_3$) (197.9 mmol, 27.3 g) was dissolved in 110 mL of water ($H_2O$), and then the resulting solution was added to the 500 mL three-neck round-bottom flask. Subsequently, tetrakis(triphenylphosphine)palladium ($Pd(PPh_3)_4$) (2.0 mmol, 2.3 g) was added to the 500 mL three-neck round-bottom flask, and then the resulting mixture was refluxed for 6 hours while the light is blocked.

The reaction mixture was cooled, and then extracted by using ethyl acetate (EA) and distilled water and concentrated, the concentrate was dissolved in 110 mL of tetrahydrofuran (THF), and the resulting solution was put into 1,100 mL of methanol and stirred for 20 minutes, and then filtered, thereby obtaining about 21 g of a yellow solid Compound 10 (yield 75%).

MALDI-TOF: m/z=1130.5321 ($C_{84}H_{66}N_4$=1130.53)

Comparative Examples 1 to 3

A compound represented by the following Formula a was commercially purchased, compounds represented by the following Formulae b and c were prepared based on the methods disclosed by Korean Patent Application Laid-Open No. 2011-0017107, and the compounds were used as compounds of Comparative Examples 1 to 3, respectively.

[Formula a]

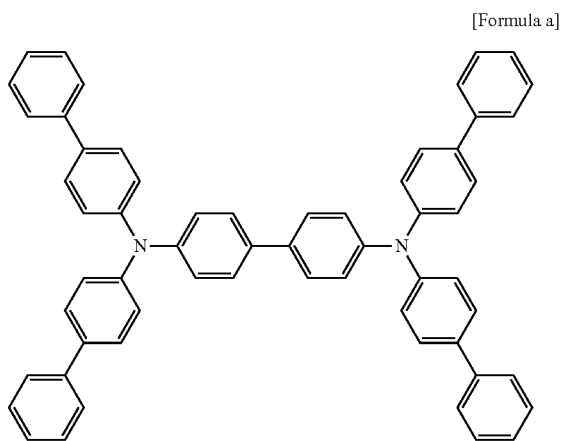

[Formula b]

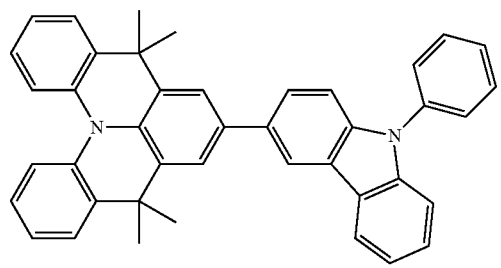

[Formula c]

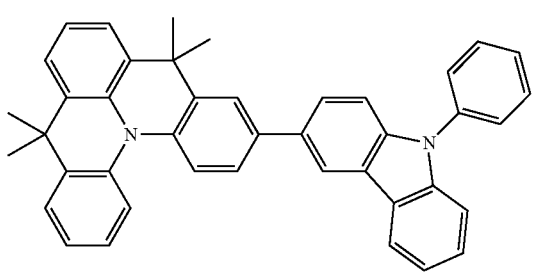

Manufacture of Light Emitting Devices A-1 to A-10

The compound according to Example 1 as a host material for a hole transport layer was deposited at a rate of 1 Å/sec, and simultaneously, a P-type dopant (HAT-CN) represented by the following Formula 9 was co-deposited at a ratio of about 3 parts by weight based on 100 parts by weight of the host material, on a first electrode formed of indium tin oxide (ITO), thereby forming a first layer having a thickness of 100 Å. The compound according to Example 1 was deposited to have a thickness of 300 Å on the first layer, thereby forming a second layer.

mCBP represented by the following Formula 10 and Ir(ppy)$_3$ represented by the following Formula 11 were co-deposited at a weight ratio of 100:9 on the second layer, thereby forming a light emitting layer having a thickness of about 400 Å, and mCBP was deposited again to have a thickness of about 50 Å on the light emitting layer, thereby forming a blocking layer.

And then, a compound represented by the following Formula 12 and Liq represented by the following Formula 13 were co-deposited at a weight ratio of 50:50 on the blocking layer, thereby forming an electron transporting layer having a thickness of about 360 Å. Subsequently, an electron injecting layer was formed on the electron transporting layer by depositing Liq again to have a thickness of 5 Å.

A second electrode using an aluminum thin film having a thickness of 1,000 Å was formed on the electron injecting layer.

[Formula 9]

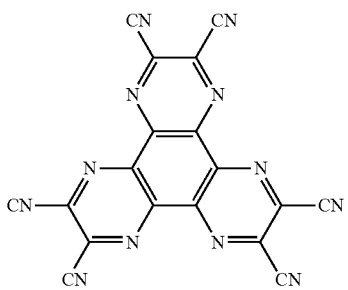

[Formula 10]

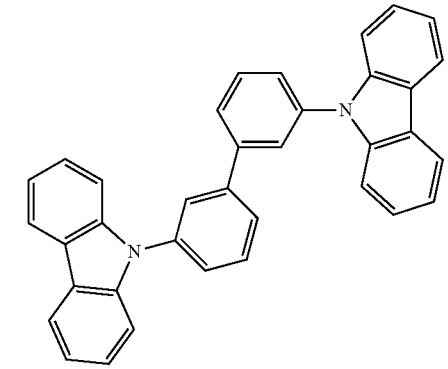

[Formula 11]

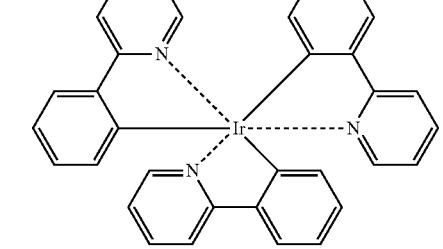

[Formula 12]

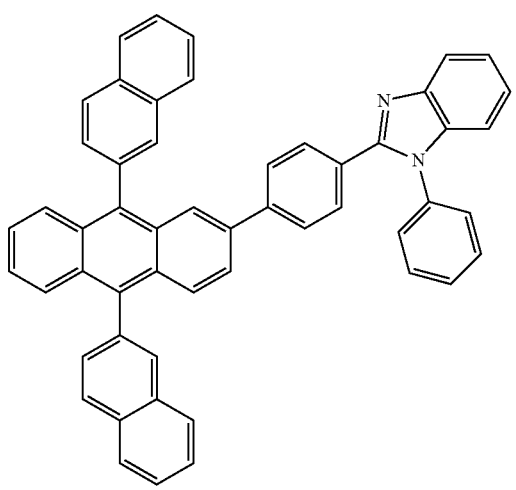

[Formula 13]

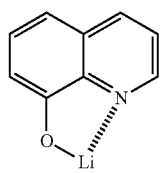

Green Light Emitting Device A-1 including the compound according to Example 1 of the present invention was manufactured by the above method.

In addition, Light Emitting Device A-2 to Light Emitting Device A-10 were manufactured through a process which is substantially the same as the process of manufacturing Light Emitting Device A-1, except that the devices were formed by using each of the compounds according to Examples 2 to 10, instead of the compound according to Example 1, as a host material of the first layer and the second layer.

Manufacture of Comparative Devices 1 to 3

Comparative Devices 1 to 3 were manufactured through a process which is substantially the same as the process of manufacturing Light Emitting Device A-1, except that the devices were formed by using each of the compounds according to Comparative Examples 1 to 3, instead of the compound according to Example 1, as a host material of the first layer and the second layer.

Evaluation-1 of Power Efficiency and Lifespan of Light Emitting Device

For each of Light Emitting Devices A-1 to A-10 and Comparative Devices 1 to 3, a sealant for UV curing was dispensed at the edge of a cover glass, to which a moisture absorbent (Getter) was attached, in a glove box under a nitrogen atmosphere, and then each of the light emitting devices and the comparative devices was cohered to the cover glass, and the sealant was cured by irradiating UV light thereon. For each of Light Emitting Devices A-1 to A-10 and Comparative Devices 1 to 3 thus prepared above, the power efficiency was measured based on the value when the brightness was 1,000 cd/m$^2$. The result is shown in Table 4. Furthermore, the lifespan of each of Light Emitting Devices A-1 to A-10 and Comparative Devices 1 to 3 was measured by using Polaronix M6000S (trade name, McScience Inc., Korea) as a lifetime measurement device. The result is shown in Table 4.

In Table 4, the unit of the result of measuring the power efficiency is lm/W. In addition, in Table 4, $T_{80}$ means a time for brightness of the light emitting device to become 80% as compared to the initial brightness, when the initial brightness of the light emitting device is 10,000 cd/m$^2$. The value for the lifespan may be converted based on the conversion equation publicly known to the person skilled in the art.

TABLE 4

| Device No. | Power efficiency [lm/W] | Lifespan ($T_{80}$[hr]) |
|---|---|---|
| Light Emitting Device A-1 | 18.3 | 97 |
| Light Emitting Device A-2 | 21.9 | 117 |
| Light Emitting Device A-3 | 28.5 | 152 |
| Light Emitting Device A-4 | 33.3 | 177 |
| Light Emitting Device A-5 | 39.9 | 213 |
| Light Emitting Device A-6 | 28.1 | 150 |
| Light Emitting Device A-7 | 28.0 | 149 |
| Light Emitting Device A-8 | 23.5 | 125 |
| Light Emitting Device A-9 | 38.5 | 205 |
| Light Emitting Device A-10 | 36.0 | 192 |
| Comparative Device 1 | 11.3 | 66 |
| Comparative Device 2 | 16.2 | 81 |
| Comparative Device 3 | 16.9 | 84 |

Referring to Table 4, it can be seen that the power efficiencies of Light Emitting Devices A-1 to A-10 are at least about 18.3 lm/W, and the average value of the power efficiencies of Light Emitting Devices A-1 to A-10 is about 30 lm/W. In contrast, it can be seen that since the power efficiencies of Comparative Devices 1 to 3 are about 11.3 lm/W to about 16.9 lm/W, the power efficiencies of the light emitting devices manufactured by using the compounds according to Examples 1 to 10 of the present invention are better than those of Comparative Devices 1 to 3.

Further, the lifespan of each of the light emitting devices manufactured by using the compounds according to the Examples of the present invention is 97 hours or more, and it can be seen that when compared to 84 hours or less of the lifespans of Comparative Devices 1 to 3, the lifespans of the light emitting devices including the compounds according to the Examples of the present invention are longer than those of Comparative Devices 1 to 3.

In particular, it can be seen that Light Emitting Device A-5 has a power efficiency of 39.9 lm/W and a lifespan of 213 hours, and thus, has the best device properties. That is, the power efficiency of Light Emitting Device A-5 has been enhanced by 136% or more compared to those of Comparative Devices 1 to 3, and the lifespan of Light Emitting Device A-5 has been enhanced by 153% or more compared to those of Comparative Devices 1 to 3.

Manufacture of Light Emitting Devices B-1 to B-4

HAT-CN represented by Formula 9 was deposited to have a thickness of about 100 Å on a first electrode formed of indium tin oxide (ITO), thereby forming a first layer, and N,N'-diphenyl-N,N'-bis(1-naphthyl)-1,1'-biphenyl-4,4'-diamine (NPB) was formed to have a thickness of about 300 Å on the first layer, thereby forming a second layer.

The compound according to Example 2 was used to form a first blocking layer having a thickness of about 100 Å on the second layer, and mCBP represented by Formula 10 and Ir(ppy)3 represented by Formula 11 were co-deposited at a weight ratio of 100:9 on the first blocking layer, thereby forming a light emitting layer having a thickness of about 400 Å. mCBP was deposited again to have a thickness of about 50 Å on the light emitting layer, thereby forming a second blocking layer.

Subsequently, the compound represented by Formula 12 and Liq represented by Formula 13 were co-deposited at a weight ratio of 50:50 on the second blocking layer, thereby forming an electron transporting layer having a thickness of about 360 Å. Subsequently, an electron injecting layer was formed on the electron transporting layer by depositing Liq again to have a thickness of 5 Å.

A second electrode was formed on the electron injecting layer by using an aluminum thin film having a thickness of 1,000 Å, thereby manufacturing Light Emitting Device B-1 including the compound according to Example 2 of the present invention.

Light Emitting Devices B-2, B-3, and B-4 were manufactured through a process which is substantially the same as the process of manufacturing Light Emitting Device B-1, except that the first blocking layer was manufactured by using each of the compounds according to Examples 3, 6, and 7 of the present invention instead of the compound according to Example 2 of the present invention.

Manufacture of Comparative Device 4

Comparative Device 4 was manufactured through a process which is substantially the same as the process of manufacturing Light Emitting Device B-1, except for the process of forming the first blocking layer. The first blocking layer of Comparative Device 4 was manufactured by using the compound according to Comparative Example 2, which is represented by Formula b.

Evaluation-2 of Power Efficiency and Lifespan of Light Emitting Device

For each of Light Emitting Devices B-1 to B-4 and Comparative Device 4 thus prepared above, the power efficiency was measured by the method, which is substantially the same as in the experiment of measuring the power efficiency for Light Emitting Devices A-1 to A-10, based on the value when the brightness was 1,000 cd/m².

Further, the lifespan of each of Light Emitting Devices B-1 to B-4 and Comparative Device 4 was measured by the method which is substantially the same as in the experiment of evaluating the lifespan for Light Emitting Devices A-1 to A-10 described above.

The results of the power efficiency and lifespan of each of Light Emitting Devices B-1 to B-4 and Comparative Device 4 are shown in Table 5. In Table 5, the unit of the result of measuring the power efficiency is lm/W. In addition, in Table 5, $T_{80}$ means a time for brightness of the light emitting device to become 80% as compared to the initial brightness, when the initial brightness of the light emitting device is 10,000 cd/m².

TABLE 5

| Device No. | Power efficiency [lm/W] | Lifespan ($T_{80}$[hr]) |
|---|---|---|
| Light Emitting Device B-1 | 30.7 | 164 |
| Light Emitting Device B-2 | 43.0 | 229 |
| Light Emitting Device B-3 | 41.5 | 221 |
| Light Emitting Device B-4 | 38.9 | 207 |
| Comparative Device 4 | 17.9 | 92 |

Referring to Table 5, it can be seen that the power efficiency of Light Emitting Device B-1 is about 30.7 lm/W, the power efficiency of Light Emitting Device B-2 is about 43.0 lm/W, and the power efficiency of each of Light Emitting Devices B-3 and B-4 is about 41.5 lm/W and about 38.9 lm/W. That is, it can be seen that the power efficiency of the light emitting device including the compound according to the present invention is at least about 30.7 lm/W, whereas the power efficiency of Comparative Device 4 is only about 17.9 lm/W. Accordingly, it can be seen that the power efficiencies of the light emitting devices using the compound according to the present invention are better than that of Comparative Device 4.

Furthermore, it can be seen that the lifespan of each of Light Emitting Devices B-1 to B-4 is at least about 165 hours, and the lifespan of Comparative Device 4 is about 92 hours. Accordingly, it can be seen that the lifespans of the light emitting devices using the compound according to the present invention are longer than that of Comparative Device 4.

Manufacture of Light Emitting Devices C-1 to C-4

NPB as a host material for the hole transport layer was deposited at a rate of 1 Å/sec, and simultaneously, the P-type dopant (HAT-CN) represented by Formula 9 was co-deposited at a ratio of about 3 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer. The compound according to Example 3 was used to form a first blocking layer having a thickness of about 100 Å on the second layer, and mCBP represented by Formula 10 and Ir(ppy)₃ represented by Formula 11 were co-deposited at a weight ratio of 100:9 on the first blocking layer, thereby forming a light emitting layer having a thickness of about 400 Å. mCBP was deposited again to have a thickness of about 50 Å on the light emitting layer, thereby forming a second blocking layer.

Subsequently, the compound represented by Formula 12 and Liq represented by Formula 13 were co-deposited at a weight ratio of 50:50 on the second blocking layer, thereby forming an electron transporting layer having a thickness of about 360 Å. Subsequently, an electron injecting layer having a thickness of about 5 Å was formed on the electron transporting layer by using Liq again.

A second electrode was formed on the electron injecting layer by using an aluminum thin film having a thickness of 1,000 Å, thereby manufacturing Light Emitting Device C-1 including the compound according to Example 3 of the present invention.

Light Emitting Devices C-2, C-3, and C-4 were manufactured through a process which is substantially the same as the process of manufacturing Light Emitting Device C-1, except that the first blocking layer was manufactured by using each of the compounds according to Examples 4, 6, and 10 of the present invention instead of the compound according to Example 3.

Manufacture of Comparative Device 5

Comparative Device 5 was manufactured through a process which is substantially the same as the process of manufacturing Light Emitting Device C-1, except that the first blocking layer was manufactured by using the compound according to Comparative Example 2, which is represented by Formula b, instead of the compound according to Example 3.

Evaluation-3 of Power Efficiency and Lifespan of Light Emitting Device

For each of Light Emitting Devices C-1 to C-4 and Comparative Device 5 thus prepared above, the power efficiency was measured by the method, which is substantially the same as in the experiment of measuring the power efficiency for Light Emitting Devices A-1 to A-10, based on the value when the brightness was 1,000 cd/m².

Further, the lifespan of each of Light Emitting Devices C-1 to C-4 and Comparative Device 5 was measured by the method which is substantially the same as in the experiment of evaluating the lifespan for Light Emitting Devices A-1 to A-10 described above.

The results of the power efficiency and lifespan of each of Light Emitting Devices C-1 to C-4 and Comparative Device 5 are shown in Table 6. In Table 6, the unit of the result of measuring the power efficiency is lm/W. In addition, in Table 6, $T_{80}$ means a time for brightness of the light emitting device to become 80% as compared to the initial brightness, when the initial brightness of the light emitting device is 10,000 cd/m².

TABLE 6

| Device No. | Power efficiency [lm/W] | Lifespan ($T_{80}$[hr]) |
|---|---|---|
| Light Emitting Device C-1 | 28.2 | 150 |
| Light Emitting Device C-2 | 46.2 | 246 |
| Light Emitting Device C-3 | 43.3 | 230 |
| Light Emitting Device C-4 | 47.9 | 255 |
| Comparative Device 5 | 19.3 | 99 |

Referring to Table 6, it can be seen that the power efficiency of each of Light Emitting Devices C-1 to C-4 is about 28.2 lm/W, about 46.2 lm/W, about 43.3 lm/W, and about 47.9 lm/W, whereas the power efficiency of Comparative Device 5 is only about 19.3 lm/W. Accordingly, it can be seen that the power efficiencies of the light emitting devices using the compound according to the present invention are better than that of Comparative Device 5.

Furthermore, it can be seen that the lifespan of each of Light Emitting Devices C-1 to C-4 is about 150 hours, about 246 hours, about 230 hours, and about 255 hours, whereas the lifespan of Comparative Device 5 is only about 99 hours. Accordingly, it can be seen that the lifespans of the light emitting devices using the compound according to the present invention are longer than that of Comparative Device 5.

Manufacture of Light Emitting Devices D-1 to D-4

The compound according to Example 1 of the present invention as a host material for the hole transport layer was deposited at a rate of 1 Å/sec, and simultaneously, the P-type dopant (HAT-CN) represented by Formula 9 was co-deposited at a ratio of about 3 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer. mCBP represented by Formula 10 and Ir(ppy)$_3$ represented by Formula 11 were co-deposited at a weight ratio of 100:9 on the second layer, thereby forming a light emitting layer having a thickness of about 400 Å, and mCBP was deposited again to have a thickness of about 50 Å on the light emitting layer, thereby forming a blocking layer.

The compound represented by Formula 12 and Liq represented by Formula 13 were co-deposited at a weight ratio of 50:50 on the second blocking layer, thereby forming an electron transporting layer having a thickness of about 360 Å. Subsequently, an electron injecting layer having a thickness of about 5 Å was formed on the electron transporting layer by using Liq again.

A second electrode was formed on the electron injecting layer by using an aluminum thin film having a thickness of 1,000 Å, thereby manufacturing Light Emitting Device D-1 including the compound according to Example 1 of the present invention.

Light Emitting Devices D-2, D-3, and D-4 were manufactured through a process which is substantially the same as the process of manufacturing Light Emitting Device D-1, except that the devices were manufactured by using each of the compounds according to Examples 5, 8, and 9 of the present invention instead of the compound according to Example 1 as the host material of the first layer.

Manufacture of Comparative Device 6

Comparative Device 6 was manufactured through a process which is substantially the same as the process of manufacturing Light Emitting Device D-1, except that the device was manufactured by using the compound according to Comparative Example 2, which is represented by Formula b as the host material of the first layer.

Evaluation-4 of Power Efficiency and Lifespan of Light Emitting Device

For each of Light Emitting Devices D-1 to D-4 and Comparative Device 6 thus prepared above, the power efficiency was measured by the method, which is substantially the same as in the experiment of measuring the power efficiency for Light Emitting Devices A-1 to A-10, based on the value when the brightness was 1,000 cd/m$^2$.

Further, the lifespan of each of Light Emitting Devices D-1 to D-4 and Comparative Device 6 was measured by the method which is substantially the same as in the experiment of evaluating the lifespan for Light Emitting Devices A-1 to A-10 described above.

The results of the power efficiency and lifespan of each of Light Emitting Devices D-1 to D-4 and Comparative Device 6 are shown in Table 7. In Table 7, the unit of the result of measuring the power efficiency is lm/W. In addition, in Table 7, T$_{80}$ means a time for brightness of the light emitting device to become 80% as compared to the initial brightness, when the initial brightness of the light emitting device is 10,000 cd/m$^2$.

TABLE 7

| Device No. | Power efficiency [lm/W] | Lifespan (T$_{80}$[hr]) |
| --- | --- | --- |
| Light Emitting Device D-1 | 33.1 | 176 |
| Light Emitting Device D-2 | 31.0 | 165 |
| Light Emitting Device D-3 | 24.1 | 126 |
| Light Emitting Device D-4 | 20.2 | 108 |
| Comparative Device 6 | 18.7 | 96 |

Referring to Table 7, it can be seen that the power efficiency of each of Light Emitting Devices D-1 to D-4 is about 33.1 lm/W, about 31.0 lm/W, about 24.1 lm/W, and about 20.2 lm/W, whereas the power efficiency of Comparative Device 6 is only about 18.7 lm/W. Accordingly, it can be seen that the power efficiencies of the light emitting devices using the compound according to the present invention are better than that of Comparative Device 6.

Further, it can be seen that the lifespan of each of Light Emitting Devices D-1 to D-4 is about 176 hours, about 165 hours, about 126 hours, and about 108 hours, whereas lifespan of Comparative Device 6 is only about 96 hours. That is, it can be seen that the lifespans of the light emitting devices using the compound according to the present invention are longer than that of Comparative Device 6.

Manufacture of Light Emitting Devices E-1 to E-4

NPB as a host material for the hole transport layer was deposited at a rate of 1 Å/sec, and simultaneously, the P-type dopant (HAT-CN) represented by Formula 9 was co-deposited at a ratio of about 3 parts by weight based on 100 parts by weight of the host material, on a first electrode formed of indium tin oxide (ITO), thereby forming a first layer having a thickness of 100 Å. The compound according to Example 2 was deposited to have a thickness of 300 Å on the first layer, thereby forming a second layer. mCBP represented by Formula 10 and Ir(ppy)$_3$ represented by Formula 11 were co-deposited at a weight ratio of 100:9 on the second layer, thereby forming a light emitting layer having a thickness of about 400 Å, and mCBP was deposited again to have a thickness of about 50 Å on the light emitting layer, thereby forming a blocking layer.

Subsequently, the compound represented by Formula 12 and Liq represented by Formula 13 were co-deposited at a weight ratio of 50:50 on the blocking layer, thereby forming an electron transporting layer having a thickness of about 360 Å. Subsequently, an electron injecting layer having a thickness of about 5 Å was formed on the electron transporting layer by using Liq again.

A second electrode was formed on the electron injecting layer by using an aluminum thin film having a thickness of 1,000 Å, thereby manufacturing Light Emitting Device E-1 including the compound according to Example 2 of the present invention.

Light Emitting Devices E-2, E-3, and E-4 were manufactured through a process which is substantially the same as the process of manufacturing Light Emitting Device E-1, except that the second layer was manufactured by using each of the compounds according to Examples 4, 6, and 10 of the present invention instead of the compound according to Example 2.

Manufacture of Comparative Device 7

Comparative Device 7 was manufactured through a process which is substantially the same as the process of manufacturing Light Emitting Device E-1, except that the second layer was manufactured by using the compound according to Comparative Example 2, which is represented by Formula b, instead of the compound according to Example 2.

Evaluation-5 of Power Efficiency and Lifespan of Light Emitting Device

For each of Light Emitting Devices E-1 to E-4 and Comparative Device 7 thus prepared above, the power efficiency was measured by the method, which is substantially the same as in the experiment of measuring the power efficiency for Light Emitting Devices A-1 to A-10, based on the value when the brightness was 1,000 cd/m².

Further, the lifespan of each of Light Emitting Devices E-1 to E-4 and Comparative Device 7 was measured by the method which is substantially the same as in the experiment of evaluating the lifespan for Light Emitting Devices A-1 to A-10 described above.

The results of the power efficiency and lifespan of each of Light Emitting Devices E-1 to E-4 and Comparative Device 7 are shown in Table 8. In Table 8, the unit of the result of measuring the power efficiency is lm/W. In addition, in Table 8, $T_{80}$ means a time for brightness of the light emitting device to become 80% as compared to the initial brightness, when the initial brightness of the light emitting device is 10,000 cd/m².

TABLE 8

| Device No. | Power efficiency [lm/W] | Lifespan ($T_{80}$[hr]) |
|---|---|---|
| Light Emitting Device E-1 | 32.9 | 175 |
| Light Emitting Device E-2 | 39.4 | 210 |
| Light Emitting Device E-3 | 35.6 | 190 |
| Light Emitting Device E-4 | 23.2 | 124 |
| Comparative Device 7 | 16.8 | 83 |

Referring to Table 8, it can be seen that the power efficiency of each of Light Emitting Devices E-1 to E-4 is about 32.9 lm/W, about 39.4 lm/W, about 35.6 lm/W, and about 23.2 lm/W, whereas the power efficiency of Comparative Device 7 is only about 16.8 lm/W. Accordingly, it can be seen that the power efficiencies of the light emitting devices using the compound according to the present invention are better than that of Comparative Device 7.

Further, it can be seen that the lifespan of each of Light Emitting Devices E-1 to E-4 is about 175 hours, about 210 hours, about 190 hours, and about 124 hours, whereas the lifespan of Comparative Device 7 is about 83 hours. Accordingly, it can be seen that the lifespan of the light emitting devices including the compound according to the present invention are better than that of Comparative Device 7.

Manufacture of Light Emitting Devices F-1 to F-10

The compound according to Example 1 as a host material for the hole transport layer was deposited at a rate of 1 Å/sec, and simultaneously, the P-type dopant (HAT-CN) represented by Formula 9 was co-deposited at a ratio of about 3 parts by weight based on 100 parts by weight of the host material, on a first electrode formed of indium tin oxide (ITO), thereby forming a first layer having a thickness of 100 Å. The compound according to Example 1 was deposited to have a thickness of 300 Å on the first layer, thereby forming a second layer.

A light emitting host represented by the following Formula 14 and a light emitting dopant represented by the following Formula 15 were co-deposited at a weight ratio of 100:5 on the second layer, thereby forming a light emitting layer having a thickness of about 200 Å. The compound represented by Formula 12 and Liq represented by Formula 13 were co-deposited at a weight ratio of 50:50 on the light emitting layer, thereby forming an electron transporting layer having a thickness of about 360 Å. Subsequently, an electron injecting layer was formed on the electron transporting layer by depositing Liq again to have a thickness of about 5 Å.

A second electrode using an aluminum thin film having a thickness of 1,000 Å was formed on the electron injecting layer.

[Formula 14]

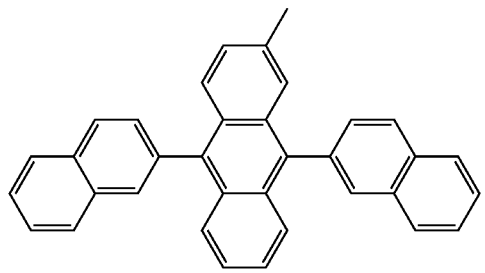

[Formula 15]

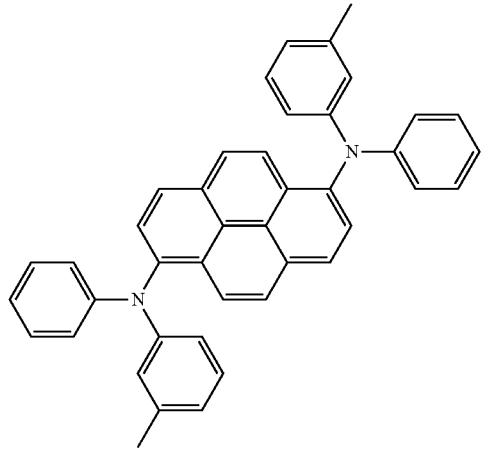

Blue Light Emitting Device F-1 including the compound according to Example 1 of the present invention was manufactured by the method described above.

In addition, Light Emitting Devices F-2 to F-10 were manufactured through a process which is substantially the same as the process of manufacturing Light Emitting Device F-1, except that the devices were formed by using each of the compounds according to Examples 2 to 10, instead of the compound according to Example 1, as a host material for the first layer and the second layer.

Manufacture of Comparative Devices 8 to 10

Comparative Devices 8 to 10 were manufactured through a process which is substantially the same as the process of manufacturing Light Emitting Device F-1, except that the devices were formed by using each of the compounds according to Comparative Examples 1 to 3, instead of the compound according to Example 1, as a host material of the first layer and the second layer.

Evaluation-6 of Power Efficiency and Lifespan of Light Emitting Device

For each of Light Emitting Devices F-1 to F-10 and Comparative Devices 8 to 10, the power efficiency was measured by the method, which is substantially the same as in the experiment of measuring the power efficiencies for Light Emitting Devices A-1 to A-10, based on the value when the brightness was 1,000 cd/m².

Furthermore, the lifespan of each of Light Emitting Devices F-1 to F-10 and Comparative Devices 8 to 10 was measured by performing the method which is the same as in the experiment of evaluating the lifespan for Light Emitting Devices A-1 to A-10 as described above, based on the value of $T_{50}$ when the initial brightness of the light emitting device is 5,000 cd/m².

The results of the power efficiency and lifespan of each of Light Emitting Devices F-1 to F-10 and Comparative Devices 8 to 10 are shown in Table 9. In Table 9, the unit of the result of measuring the power efficiency is lm/W. In addition, in Table 9, $T_{50}$ means a time for brightness of the light emitting device to become 50% as compared to the initial brightness, when the initial brightness of the light emitting device is 5,000 cd/m².

TABLE 9

| Device No. | Power efficiency [lm/W] | Lifespan ($T_{50}$[hr]) |
|---|---|---|
| Light Emitting Device F-1 | 7.0 | 232 |
| Light Emitting Device F-2 | 7.5 | 290 |
| Light Emitting Device F-3 | 7.3 | 264 |
| Light Emitting Device F-4 | 7.7 | 280 |
| Light Emitting Device F-5 | 8.6 | 352 |
| Light Emitting Device F-6 | 7.0 | 247 |
| Light Emitting Device F-7 | 7.1 | 235 |
| Light Emitting Device F-8 | 7.4 | 262 |
| Light Emitting Device F-9 | 8.1 | 331 |
| Light Emitting Device F-10 | 7.9 | 313 |
| Comparative Device 8 | 4.7 | 123 |
| Comparative Device 9 | 5.5 | 171 |
| Comparative Device 10 | 5.9 | 205 |

Referring to Table 9, the power efficiency of each of Blue Light Emitting Devices F-1 to F-10 manufactured by using the compounds according to Examples 1 to 10 of the present invention is at least about 7.0 lm/W. It can be seen that when compared to a power efficiency of about 5.9 lm/W or less in Comparative Devices 8 to 10, the power efficiencies of the light emitting devices including the compound according to the present invention are better than those of Comparative Devices 8 to 10.

It can be seen that Light Emitting Devices F-1 to F-10 are a fluorescent light emitting device which emits light corresponding to the blue wavelength region, and have a lower power efficiency than those of phosphorescent Light Emitting Devices A-1 to A-10 which emit light corresponding to the green wavelength region, but the power efficiencies have been improved by at least about 18.6% compared to those of Comparative Devices 8 to 10. It can be seen that in the case of Light Emitting Device F-5, the power efficiency has been improved by about 82% compared to that of Comparative Device 8.

Further, it can be seen that Light Emitting Devices F-1 to F-10 have a lifespan of at least 232 hours, whereas Comparative Devices 8 to 10 have a lifespan of about 205 hours or less. Accordingly, it can be seen that the lifespans of the light emitting devices including the compound according to the present invention are longer than those of Comparative Devices 8 to 10. It can be seen that the lifespans of Light Emitting Devices F-1 to F-10 have been improved by at least about 13% compared to those of Comparative Devices 8 to 10 It can be seen that in the case of Light Emitting Device F-5, the lifespan has been improved by about 186% compared to that of Comparative Device 8.

In consideration of the technology level in the art that the blue light emitting device using a fluorescent material has generally lower power efficiency or lifespan than that of a green light emitting device using a phosphorescent material, it can be seen that the power efficiencies of Light Emitting Devices F-1 to F-10 using the compound according to the present invention have been significantly improved compared to those of Comparative Devices 8 to 10, particularly, Comparative Device 8. In addition, it can be seen that the lifespans of Light Emitting Devices F-1 to F-10 also have been significantly increased compared to those of Comparative Devices 8 to 10, particularly, Comparative Device 8.

Manufacture of Light Emitting Devices G-1 to G-10

HAT-CN represented by Formula 9 was deposited to have a thickness of about 100 Å on a first electrode formed of indium tin oxide (ITO), thereby forming a first layer, and NPB was formed to have a thickness of about 300 Å on the first layer, thereby forming a second layer.

The compound according to Example 1 was used to form a first blocking layer having a thickness of about 100 Å on the second layer, and the light emitting host represented by Formula 14 and the light emitting dopant represented by Formula 15 were co-deposited at a weight ratio of 100:5 on the first blocking layer, thereby forming a light emitting layer having a thickness of about 200 Å. The compound represented by Formula 12 and Liq represented by Formula 13 were co-deposited at a weight ratio of 50:50 on the light emitting layer, thereby forming an electron transporting layer having a thickness of about 360 Å. Subsequently, an electron injecting layer was formed on the electron transporting layer by depositing Liq again to have a thickness of about 5 Å. A second electrode using an aluminum thin film having a thickness of 1,000 Å was formed on the electron injecting layer.

Through the process as described above, Light Emitting Device G-1 including the compound according to Example 1 of the present invention was manufactured. Light Emitting Devices G-2 to G-10 were manufactured through a process which is substantially the same as the process of manufacturing Light Emitting Device G-1, except that the first blocking layer was manufactured by using each of the compounds according to Examples 2 to 10 of the present invention instead of the compound according to Example 1.

Manufacture of Comparative Devices 11 to 13

Comparative Devices 11 to 13 were manufactured through a process which is substantially the same as the process of manufacturing Light Emitting Device G-1, except for the process of forming the first blocking layer. The first blocking layer of each of Comparative Devices 11, 12, and 13 was manufactured by using each of the compounds according to Comparative Examples 1 to 3.

Evaluation-7 of Power Efficiency and Lifespan of Light Emitting Device

For each of Light Emitting Devices G-1 to G-10 and Comparative Devices 11 to 13 thus prepared above, the power efficiency was measured by the method, which is substantially the same as in the experiment of measuring the power efficiency for Light Emitting Devices F-1 to F-10, based on the value when the brightness was 1,000 cd/m². Furthermore, the lifespans of Light Emitting Devices G-1 to G-10 and Comparative Devices 11 to 13 were measured by the method which is substantially the same as in the experiment of evaluating the lifespan for Light Emitting Devices F-1 to F-10 described above.

The results of the power efficiency and lifespan of each of Light Emitting Devices G-1 to G-10 and Comparative Devices 11 to 13 are shown in Table 10. In Table 10, the unit of the result of measuring the power efficiency is lm/W. In addition, in Table 10, $T_{50}$ means a time for brightness of the light emitting device to become 50% as compared to the initial brightness, when the initial brightness of the light emitting device is 5,000 cd/m$^2$.

TABLE 10

| Device No. | Power efficiency [lm/W] | Lifespan ($T_{50}$[hr]) |
| --- | --- | --- |
| Light Emitting Device G-1 | 6.9 | 211 |
| Light Emitting Device G-2 | 7.2 | 253 |
| Light Emitting Device G-3 | 7.0 | 233 |
| Light Emitting Device G-4 | 7.1 | 241 |
| Light Emitting Device G-5 | 7.9 | 305 |
| Light Emitting Device G-6 | 6.7 | 212 |
| Light Emitting Device G-7 | 6.9 | 235 |
| Light Emitting Device G-8 | 7.2 | 263 |
| Light Emitting Device G-9 | 7.5 | 287 |
| Light Emitting Device G-10 | 7.3 | 271 |
| Comparative Device 11 | 3.9 | 90 |
| Comparative Device 12 | 4.3 | 110 |
| Comparative Device 13 | 5.3 | 176 |

Referring to Table 10, it can be seen that the power efficiency of each of Light Emitting Devices G-1 to G-10 manufactured by using the compounds according to the present invention is 6.7 lm/W or more, whereas the power efficiencies of Comparative Devices 11 to 13 are 5.3 lm/W or less. Accordingly, it can be seen that the power efficiencies of the light emitting devices including the compound according to the present invention are better than those of Comparative Devices 11 to 13. It can be seen that the power efficiencies of Light Emitting Devices G-1 to G-10 have been improved by about 26% or more compared to the power efficiencies of Comparative Devices 11 to 13. It can be seen that in the case of Light Emitting Device G-5, the power efficiency has been improved by about 102.5% compared to that of Comparative Device 11.

Furthermore, it can be seen that the lifespan of each of Light Emitting Devices G-1 to G-10 is at least about 211 hours, whereas the lifespans of Comparative Devices 11 to 13 are 176 hours. According to this, it can be seen that the lifespans of the light emitting devices manufactured by using the compounds according to the present invention are relatively longer than those of Comparative Devices 11 to 13. It can be seen that the lifespans of Light Emitting Devices G-1 to G-10 have been improved by at least about 19% compared to those of Comparative Devices 11 to 13. It can be seen that in the case of Light Emitting Device G-5, the lifespan has been improved by about 238% compared to that of Comparative Device 11.

In consideration of the technology level in the art that the blue light emitting device using a fluorescent material has generally lower power efficiency or lifespan than that of a green light emitting device using a phosphorescent material, it can be seen that the power efficiencies of Light Emitting Devices G-1 to G-10 using the compound according to the present invention have been significantly improved compared to those of Comparative Devices 11 to 13, particularly, Comparative Device 11. In addition, it can be seen that the lifespans of Light Emitting Devices G-1 to G-10 have been significantly increased compared to those of Comparative Devices 11 to 13, particularly, Comparative Device 11.

Manufacture of Light Emitting Devices H-1 to H-10

NPB as a host material for the hole transport layer was deposited at a rate of 1 Å/sec, and simultaneously, the P-type dopant (HAT-CN) represented by Formula 9 was co-deposited at a ratio of about 3 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer.

The compound according to Example 1 was used to form a first blocking layer having a thickness of about 100 Å on the second layer, and the light emitting host represented by Formula 14 and the light emitting dopant represented by Formula 15 were co-deposited at a weight ratio of 100:5, thereby forming a light emitting layer having a thickness of about 200 Å. The compound represented by Formula 12 and Liq represented by Formula 13 were co-deposited at a weight ratio of 50:50 on the light emitting layer, thereby forming an electron transporting layer having a thickness of about 360 Å. Subsequently, an electron injecting layer was formed on the electron transporting layer by depositing Liq again to have a thickness of about 5 Å. A second electrode using an aluminum thin film having a thickness of 1,000 Å was formed on the electron injecting layer.

Through the process as described above, Light Emitting Device H-1 including the compound according to Example 1 of the present invention was manufactured.

Light Emitting Devices H-2 to H-10 were manufactured through a process which is substantially the same as the process of manufacturing Light Emitting Device H-1, except that the first blocking layer was manufactured by using each of the compounds according to Examples 2 to 10 of the present invention instead of the compound according to Example 1.

Manufacture of Comparative Devices 14 to 16

Comparative Devices 14 to 16 were manufactured through a process which is substantially the same as the process of manufacturing Light Emitting Device H-1, except for the process of forming the first blocking layer. The first blocking layer of each of Comparative Devices 14, 15, and 16 was manufactured by using each of the compounds according to Comparative Examples 1 to 3.

Evaluation-8 of Power Efficiency and Lifespan of Light Emitting Device

For each of Light Emitting Devices H-1 to H-10 and Comparative Devices 14 to 16 thus prepared above, the power efficiency was measured by the method, which is substantially the same as in the experiment of measuring the power efficiency for Light Emitting Devices F-1 to F-10, based on the value when the brightness was 1,000 cd/m$^2$.

Furthermore, the lifespans of Light Emitting Devices H-1 to H-10 and Comparative Devices 14 to 16 were measured by the method which is substantially the same as in the experiment of evaluating the lifespan for Light Emitting Devices F-1 to F-10 described above.

The results of the power efficiency and lifespan of each of Light Emitting Devices H-1 to H-10 and Comparative Devices 14 to 16 are shown in Table 11. In Table 11, the unit of the result of measuring the power efficiency is lm/W. In addition, in Table 11, $T_{50}$ means a time for brightness of the light emitting device to become 50% as compared to the initial brightness, when the initial brightness of the light emitting device is 5,000 cd/m$^2$.

TABLE 11

| Device No. | Power efficiency [lm/W] | Lifespan ($T_{50}$[hr]) |
| --- | --- | --- |
| Light Emitting Device H-1 | 6.5 | 220 |
| Light Emitting Device H-2 | 6.8 | 209 |
| Light Emitting Device H-3 | 6.4 | 213 |
| Light Emitting Device H-4 | 7.0 | 249 |
| Light Emitting Device H-5 | 7.7 | 270 |
| Light Emitting Device H-6 | 6.3 | 191 |
| Light Emitting Device H-7 | 6.8 | 206 |
| Light Emitting Device H-8 | 6.7 | 202 |
| Light Emitting Device H-9 | 7.3 | 250 |
| Light Emitting Device H-10 | 7.2 | 257 |
| Comparative Device 14 | 4.1 | 103 |
| Comparative Device 15 | 4.9 | 152 |
| Comparative Device 16 | 5.1 | 161 |

Referring to Table 11, it can be seen that the power efficiency of each of Light Emitting Devices H-1 to H-10 manufactured by using the compounds according to Examples 1 to 10 of the present invention is at least 6.3 lm/W or more, and as compared to the power efficiency of about 5.1 lm/W or less of Comparative Devices 14 to 16, the power efficiencies of the light emitting devices including the compound according to the present invention are better than those of Comparative Device 14 to 16. It can be seen that the power efficiencies of Light Emitting Devices H-1 to H-10 have been improved by at least 23% compared to those of Comparative Devices 14 to 16. It can be seen that in the case of Light Emitting Device H-5, the power efficiency has been improved by about 87% compared to Comparative Device 14.

Further, it can be seen that Light Emitting Devices H-1 to H-10 have a lifespan of at least about 191 hours, whereas Comparative Devices 14 to 16 have a lifespan of about 161 hours or less. Accordingly, it can be seen that the lifespans of the light emitting devices including the compound according to the present invention are longer than those of Comparative Devices 14 to 16. It can be seen that the lifespans of Light Emitting Devices H-1 to H-10 have been improved by at least about 25% compared to those of Comparative Devices 14 to 16. It can be seen that in the case of Light Emitting Device H-5, the lifespan has been improved by about 162% compared to that of Comparative Device 14.

In consideration of the technology level in the art that the blue light emitting device using a fluorescent material has generally lower power efficiency or lifespan than that of a green light emitting device using a phosphorescent material, it can be seen that the power efficiencies of Light Emitting Devices H-1 to H-10 using the compound according to the present invention have been significantly improved compared to those of Comparative Devices 14 to 16, particularly, Comparative Device 14. In addition, it can be seen that the lifespans of Light Emitting Devices H-1 to H-10 have been significantly increased compared to those of Comparative Devices 14 to 16, particularly, Comparative Device 14.

| EXPLANATION OF CODES | |
| --- | --- |
| 100, 102, 104: light emitting device | 10: base substrate |
| 20: first electrode | 30, 32, 34: hole transport layer |
| 33a: first layer | 33b: second layer |
| 40: light emitting layer | 50: second electrode |

What is claimed is:
1. A compound represented by the following Formula 3:

[Formula 3]

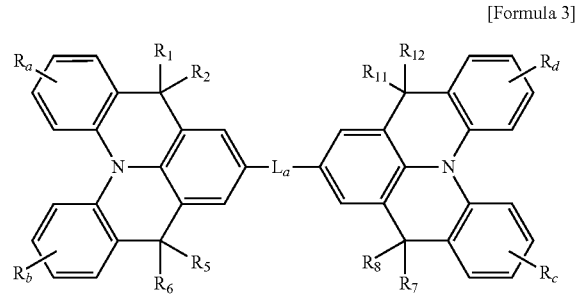

in Formula 3,
La represents a single bond, an arylene group having 6 to 30 carbon atoms, or a heteroarylene group having 2 to 30 carbon atoms,
Ra and Rb each independently represent an aryl group having 6 to 30 carbon atoms,
Rc, and Rd each independently represent hydrogen,
R1, R2, R5, R6, R7, R8, R11, and R12 each independently represent an alkyl group having 1 to 6 carbon atoms.
2. A compound selected from the following Structures 55, 60 to 66, and 90 to 98:

<Structure 55>

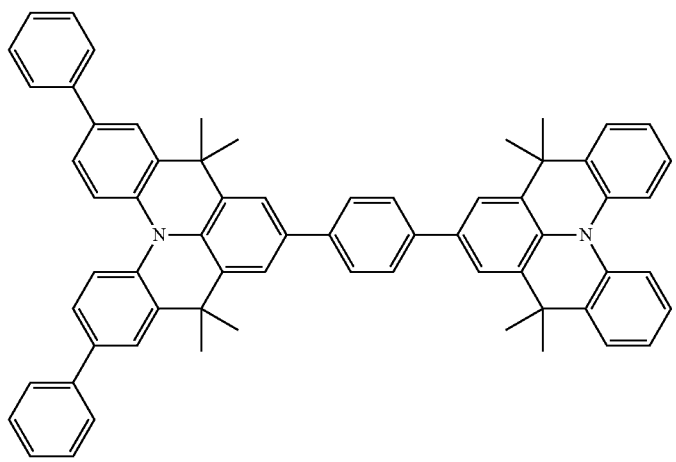

<Structure 60>
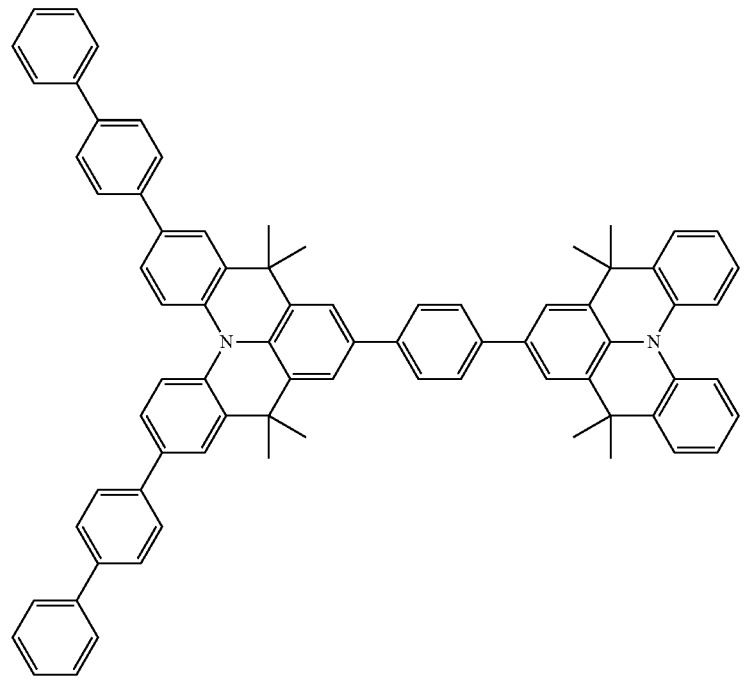
<Structure 61>
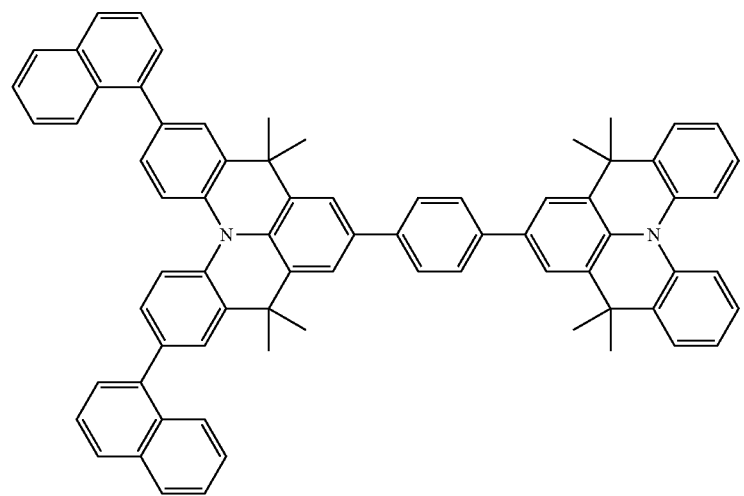

-continued
<Structure 62>
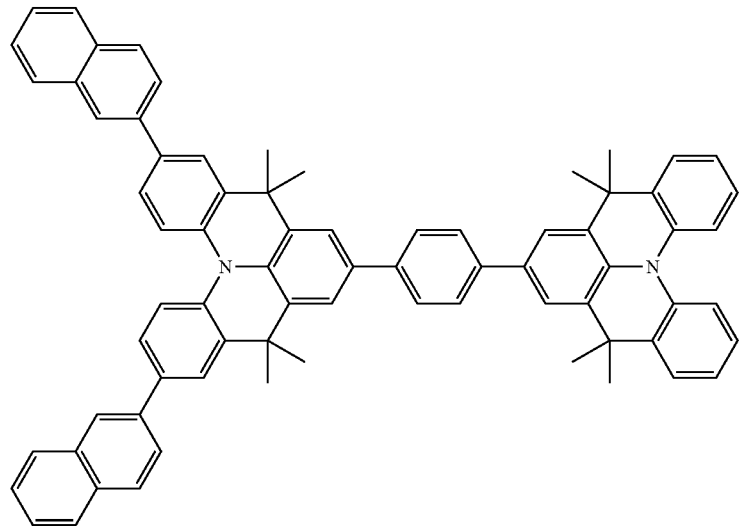
<Structure 63>
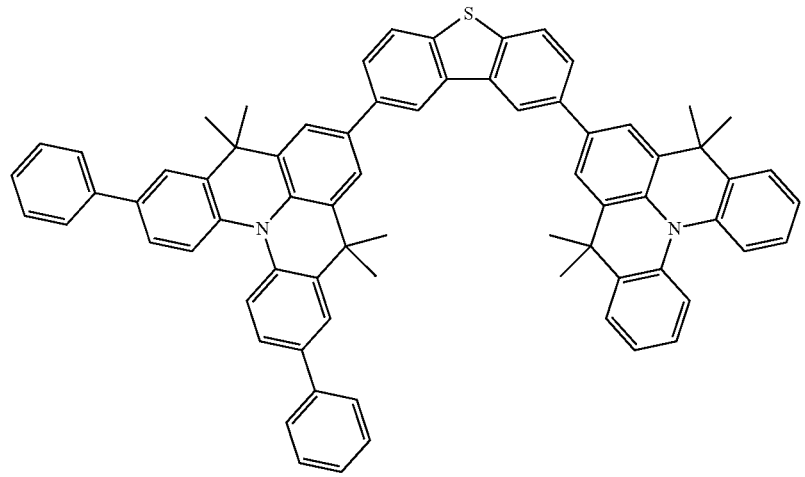
<Structure 64>
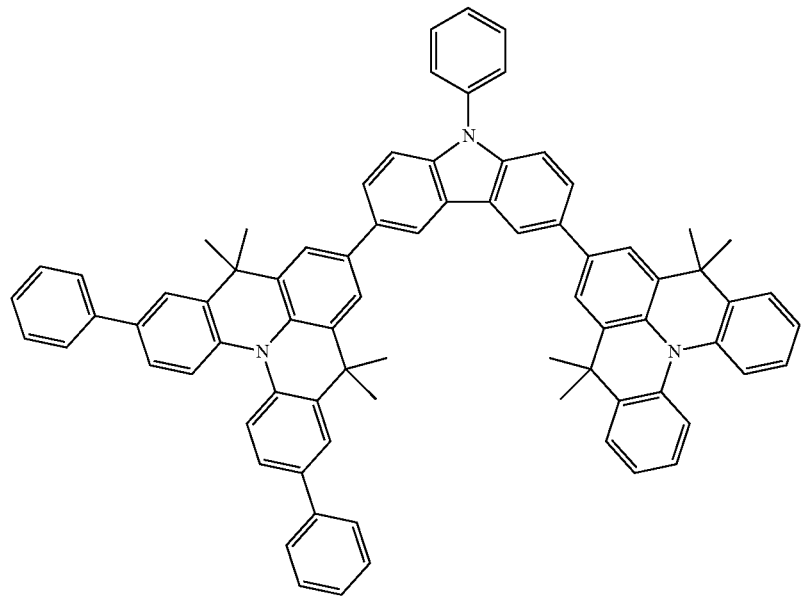

<Structure 65>
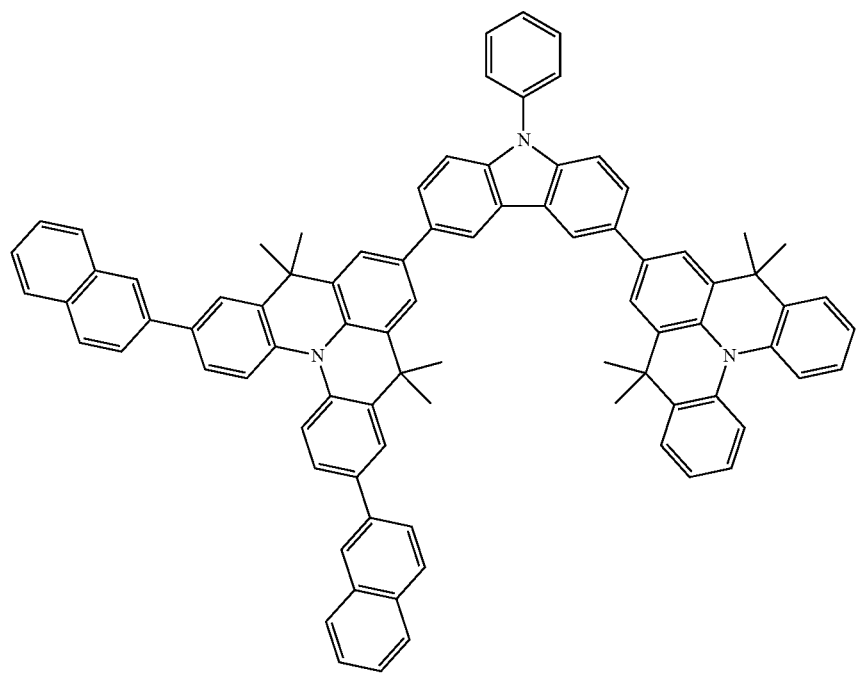
<Structure 66>
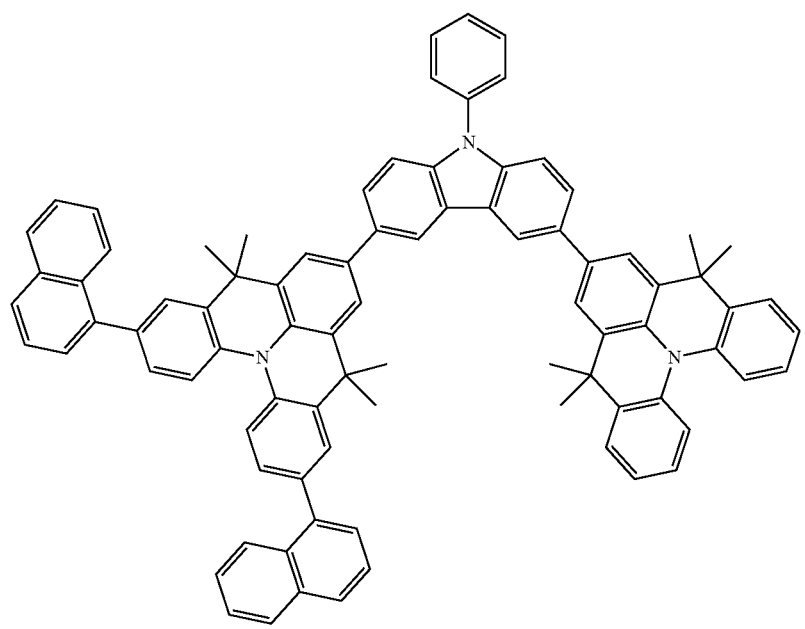

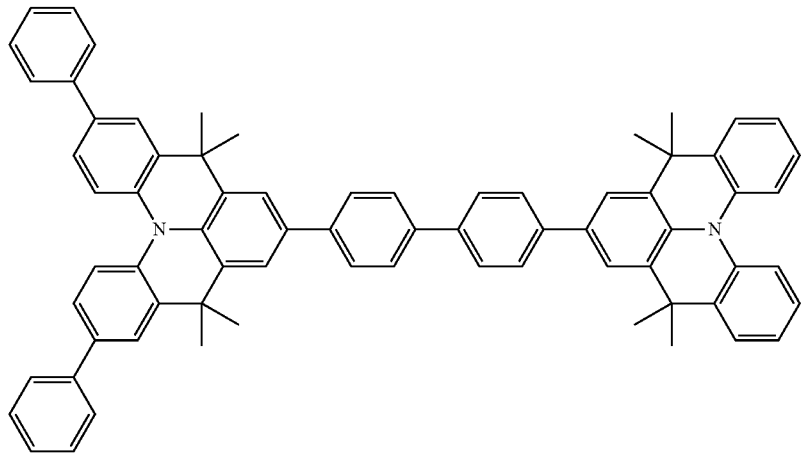
<Structure 90>
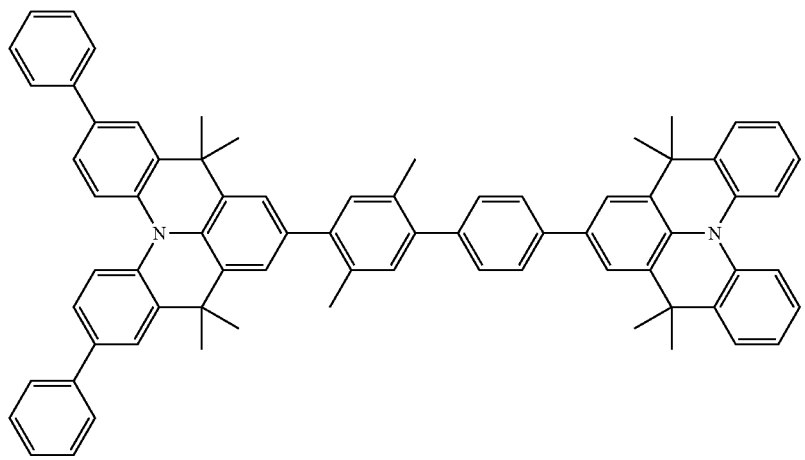
<Structure 91>
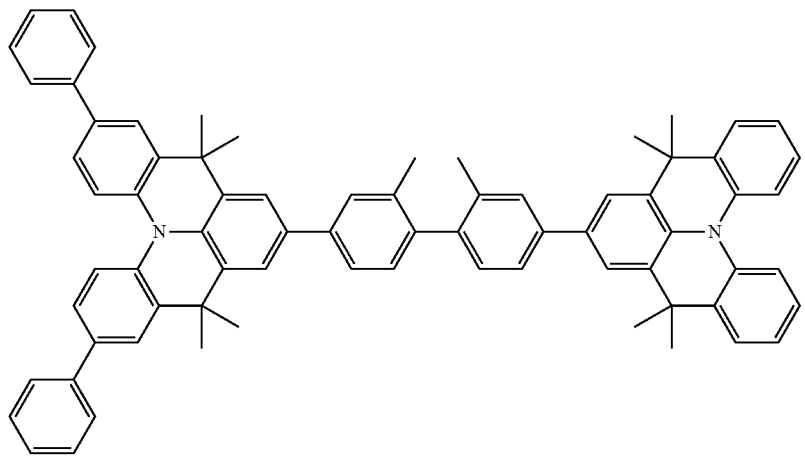
<Structure 92>

<Structure 93>
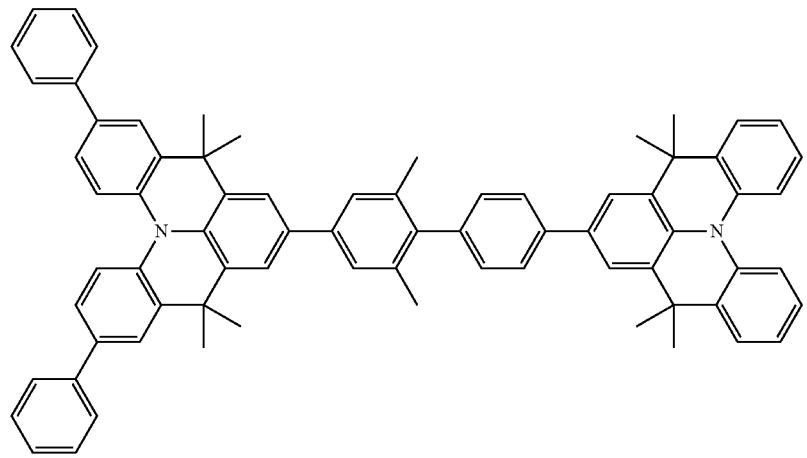
<Structure 94>
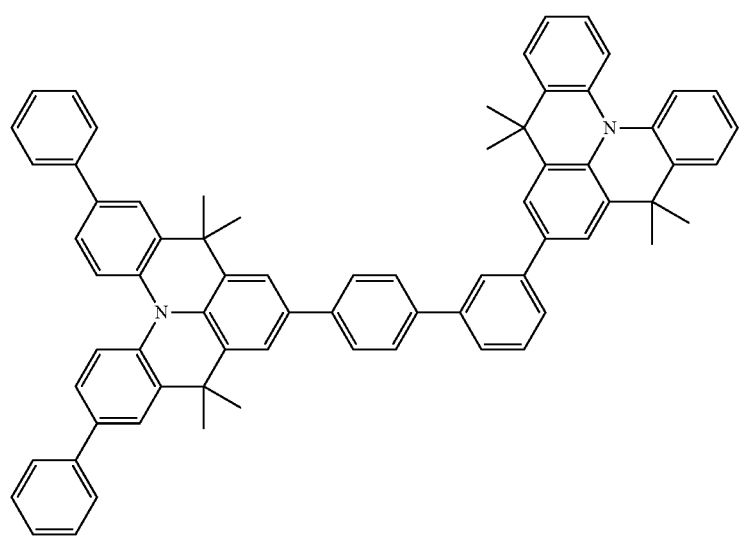
<Structure 95>
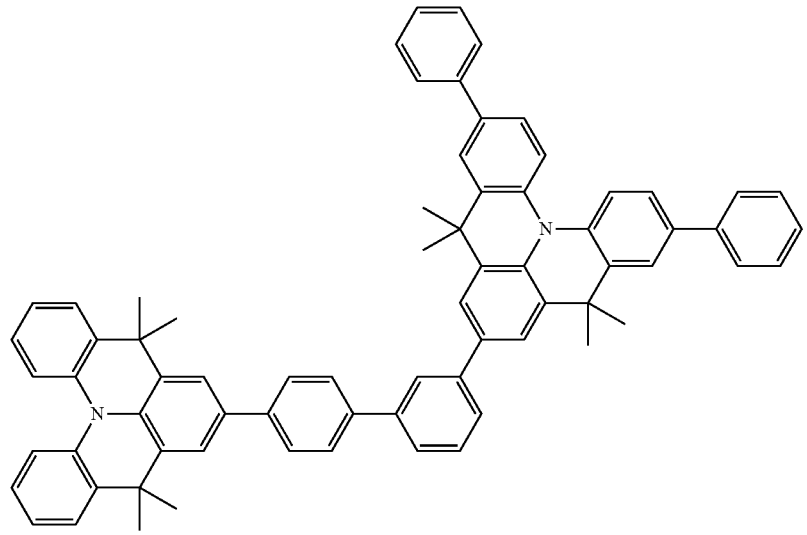

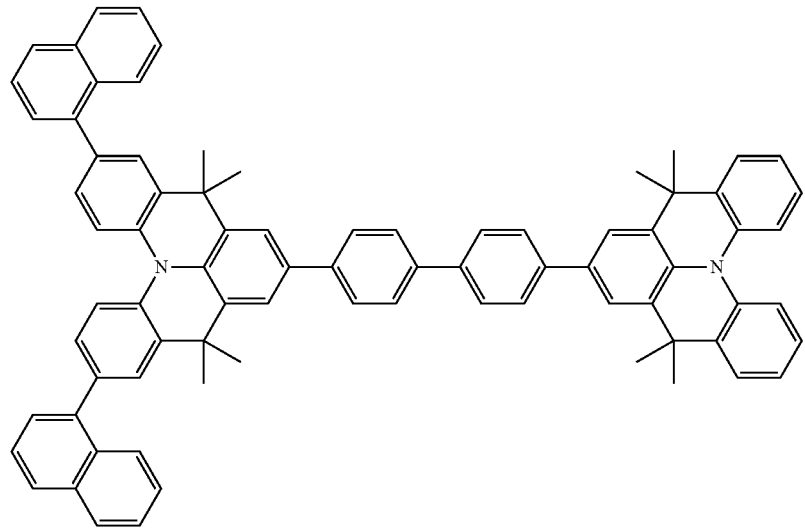
<Structure 96>
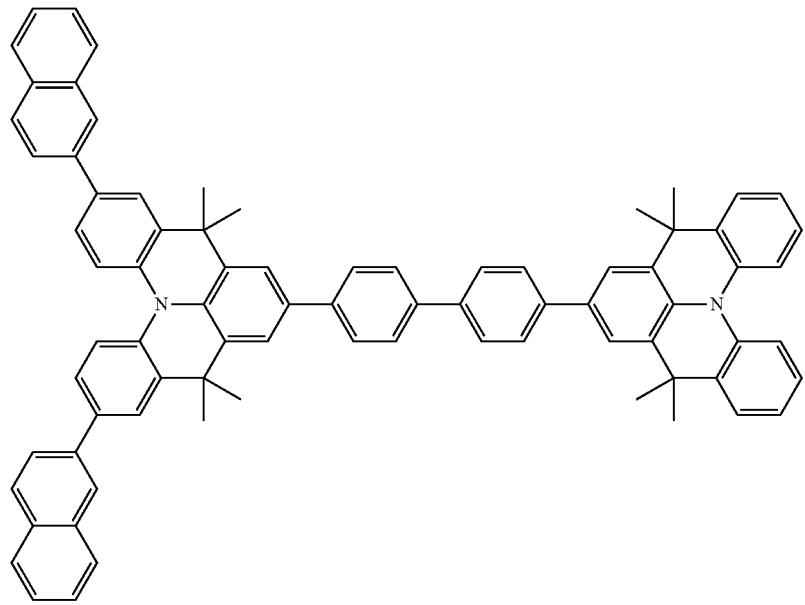
<Structure 97>
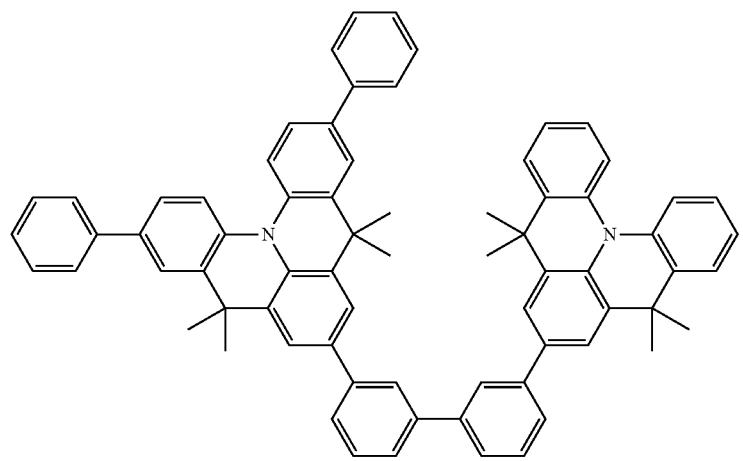
<Structure 98>

3. A light emitting device comprising:
a first electrode;
a second electrode;
a light emitting layer disposed between the first electrode and the second electrode; and
an organic layer disposed between the first electrode and the light emitting layer, the organic layer comprising the compound of claim 1.

4. The light emitting device of claim 3, wherein the organic layer is a hole transport layer further comprising a P-type dopant.

5. The light emitting device of claim 3, wherein the organic layer is a hole transport layer comprising:
a first layer comprising the compound and a P-type dopant; and
a second layer comprising the compound.

6. The light emitting device of claim 3, further comprising:
a blocking layer disposed between the organic layer and the light emitting layer,
wherein the organic layer is a hole transport layer.

7. The light emitting device of claim 3, further comprising:
a hole transport layer disposed between the organic layer and the first electrode,
wherein the organic layer is a blocking layer.

8. An electronic device comprising the light emitting device of claim 3.

9. The electronic device of claim 8, wherein the electronic device is a display device or a lighting device.

* * * * *